US008444958B2

(12) United States Patent
Kamasaka et al.

(10) Patent No.: US 8,444,958 B2
(45) Date of Patent: May 21, 2013

(54) COMPOSITIONS HAVING ANTI-DENTAL CARIES FUNCTION

(75) Inventors: Hiroshi Kamasaka, Osaka (JP); Takahisa Nishimura, Nara (JP); Kenji Too, Osaka (JP); Takashi Kuriki, Osaka (JP); Shigetaka Okada, Nara (JP); Reiichiro Sakamoto, Ibaraki (JP); Toshiyuki Kimura, Chiba (JP); Nobuo Uotsu, Chiba (JP)

(73) Assignee: Ezaki Glico Co., Ltd., Osaka (JP)

( * ) Notice: Subject to any disclaimer, the term of this patent is extended or adjusted under 35 U.S.C. 154(b) by 742 days.

(21) Appl. No.: 10/469,478

(22) PCT Filed: Feb. 28, 2002

(86) PCT No.: PCT/JP02/01888
§ 371 (c)(1),
(2), (4) Date: Dec. 10, 2003

(87) PCT Pub. No.: WO02/067871
PCT Pub. Date: Sep. 6, 2002

(65) Prior Publication Data
US 2004/0105823 A1   Jun. 3, 2004

(30) Foreign Application Priority Data

Feb. 28, 2001   (JP) .................................. 2001-56010
Feb. 28, 2001   (JP) .................................. 2001-56011

(51) Int. Cl.
*A61K 8/00* (2006.01)
(52) U.S. Cl.
USPC ............................................. 424/49; 514/54

(58) Field of Classification Search
USPC .................................................... 424/49, 440
See application file for complete search history.

(56) References Cited

U.S. PATENT DOCUMENTS

| 4,177,258 | A | * | 12/1979 | Gaffar et al. .................... 424/52 |
| 4,855,128 | A | | 8/1989 | Lynch et al. |
| 5,215,740 | A | | 6/1993 | Domke et al. .................. 424/52 |
| 5,711,938 | A | | 1/1998 | Larm ............................... 424/49 |
| 5,895,641 | A | | 4/1999 | Usen et al. ....................... 424/52 |
| 5,952,308 | A | | 9/1999 | Nakanishi et al. .............. 514/25 |

(Continued)

FOREIGN PATENT DOCUMENTS

| CN | 1192124 A | 9/1998 |
| EP | 0 241 818 A2 | 10/1987 |

(Continued)

OTHER PUBLICATIONS

Inaba et al.; "A Computer-Assisted Videodensitometric Method to Visualize Mineral Distributions in in vitro and in vivo Formed Root Caries Lesions"; European Journal of Oral Sciences; Sep. 1997.

(Continued)

*Primary Examiner* — Brian Gulledge
*Assistant Examiner* — Snigdha Maewall
(74) *Attorney, Agent, or Firm* — Renner, Otto, Boisselle & Sklar, LLP

(57) ABSTRACT

The present invention relates to dietary compositions and oral compositions having an anti-dental caries function. The present invention provides dietary compositions and oral compositions having an anti-dental caries function which contain a buffering agent having a pH buffering action in the oral cavity.

5 Claims, 30 Drawing Sheets

U.S. PATENT DOCUMENTS

| | | | |
|---|---|---|---|
| 6,013,274 A | 1/2000 | Chaykin | 424/440 |
| 6,203,827 B1 | 3/2001 | Katsukura | |
| 6,951,463 B2 * | 10/2005 | Masuhara et al. | 433/216 |

FOREIGN PATENT DOCUMENTS

| | | |
|---|---|---|
| EP | 0 396 232 A2 | 11/1990 |
| EP | 0719783 A2 | 7/1996 |
| JP | 04-099712 | 3/1992 |
| JP | EP 0 719 783 A2 * | 3/1996 |
| JP | 08-104696 | 4/1996 |
| JP | 9168384 | 6/1997 |
| JP | 11-158197 | 6/1999 |
| JP | 2000-154127 | 6/2000 |
| JP | 2000-191486 | 7/2000 |
| JP | 2000-247852 | 9/2000 |
| RU | 1796179 | 2/1993 |
| WO | 98/13012 | 4/1998 |
| WO | 00/56375 | 9/2000 |

OTHER PUBLICATIONS

Inaba et al.; "Computerized Measurements of Microradiographic Mineral Parameters of De- and Remineralized Dental Hard Tissues"; Journal of Dental Health; 1997; pp. 67-73.

Imai et al.; "Inhibitory Effect of Phosphoryl Oligosaccharides against Enamel Demineralization by Mutans Streptococci." Date of disclosure: Nov. 27, 2001; Place of disclosure: http://iadr.confex.com/iadr/2002SanDiego/techprogram/abstract_15492.htm.

Kamasaka et al.; "Enhanced Remineralization of Enamel by Saliva Stimulated by a Sugar-free Gum Containing Phosphoryl-Oligosaccharides (Pos)." Date of disclosure: Nov. 27, 2001; Place of disclosure: http://iadr.confex.com/iadr/2002SanDiego/techprogram/abstract_7806.htm.

Inaba et al.; "Enhanced Remineralization of Enamel by a Chewing Gum Containing Phosphoryl-Oligosaccharides (Pos) in situ." Date of disclosure: Nov. 27, 2001; Place of disclosure: http://iadr.confex.com/iadr/2002SanDiego/techprogram/abstract_16561.htm.

Chinese Office Action for corresponding Application No. 02805648.5 dated Nov. 12, 2004.

Japanese Office Action corresponding to Application No. 2002-055096 dated May 26, 2006.

Japanese Office Action corresponding to Application No. 2002-055110 dated May 26, 2006.

Japanese Translation of Chinese Office Action, Application No. 200510082015.8, dated Aug. 1, 2008.

Margolis et al.; "Effect of Fluoride on Crystal Growth of Calcium apatites in the Presence of a Salivary Inhibitor"; Calcified Tissue International; 1982.

Japanese Office Action, Application No. 2006-202636, dated Sep. 25, 2008.

2005100820158; Chinese Office Action dated Sep. 4, 2009.

* cited by examiner

Comparison of the lesion depth (A; ld) and mineral loss (B; ΔZ) values by types of gums (+POs and -POs).

Vertical bar = SD. * $p<0.001$, n=12

Remineralization rate (ld reduction %age with respect to the initial ld value after demineralization) by durations of intraoral experiments.
Suc.= sucrose group, Xyl = xylitol group, POs = POs group.

Structure of phosphorylated oligosaccharides (POs)

Symbols: P-3, P-6 phosphate group linked to position 3 or 6 of a glucose residue; ○ glucose residue; ◐ reducing terminal glucose residue; ● glucose residue which may be deleted

COMPOSITIONS HAVING ANTI-DENTAL CARIES FUNCTION

TECHNICAL FIELD

The present invention relates to dietary compositions and oral compositions having an anti-dental caries function. More particularly, the present invention relates to dietary compositions and oral compositions having an anti-dental caries function, such as remineralization of teeth to reduce the development of dental caries.

BACKGROUND ART

Dental caries is a demineralization of the tooth surface caused by oral bacteria present thereon. Specifically, organic acid produced by the oral bacteria is prevented from being diffused by some obstructions and the teeth are exposed to a high concentration of the organic acid, so that the tooth surface is demineralized. In this definition, any oral bacteria having the ability to ferment sugar to produce organic acid by metabolism can cause dental caries. Substrates suitable for organic acid production are saccharides, including monosaccharides and oligosaccharides (e.g., glucose and sucrose), and polysaccharides (e.g., starch) which are polymers of monosaccharides.

The dispersion of organic acid is prevented roughly due to (1) retention of starch taken from diet at the neck and root of tooth, and (2) adhesion of insoluble glucan to tooth, which is produced by bacteria using easily degradable sugars, such as sucrose (i.e., fermentative sugars) as substrates.

As to factor (1), any oral bacteria having the ability to ferment sugar, such as lactobacillus, is considered to be responsible for dental caries. In this case, it is known that the progression of dental caries is generally slow. The development of an environment in which a high concentration of organic acid is produced depends on passive factors.

Factor (2) is a major factor for dental caries today when sucrose-containing foods are widely available. In this case, *Streptococcus mutans* and *Streptococcus sobrinus* are believed to be causative. Both bacteria are a type of *Streptococcus* which occurs in chains, each cell having a diameter of about 0.6 μm in a round form. Both bacteria vigorously produce water-insoluble α-glucan in the presence of sucrose. This glucan has a property to adhere very well to the tooth surface. The bacteria rapidly metabolize sucrose, exerting the ability to produce acid. The bacteria per se have strong acid resistance and can survive in an acid environment in which other bacteria cannot grow. The adhesiveness of the water-insoluble glucan allows the bacteria to be firmly adhered to the tooth surface and the like. The water-insoluble glucan adsorbed to the tooth surface prevents the dispersion of organic acid produced by the bacteria, resulting in an environment in which the tooth surface is exposed to a high concentration of organic acid. It is considered that as compared to factor (1), the creation of the environment in which a high concentration of organic acid is produced depends on an active factor of the bacteria. In this case, the progression of dental caries is faster than that caused by factor (1).

There is a new approach to prevent dental caries by considering the health of teeth at microscopic levels, i.e., demineralization and remineralization of dentin (Yoichi Iijima, Takashi Kumagaya; Kariesu Kontororu Dakkai-to Saisekkaika-no-Mekanizumu [Caries Control—Mechanism of Demineralization and Remineralization], Ishiyaku Shuppan K.K.; 21-51, 1999). The surface of a tooth is made of calcium and hydroxyapatite [$Ca_{10}(PO_4)_6(OH)_2$] which is a crystal of phosphate, and is called enamel. Enamel is the hardest part of a tooth, and prevents important calcium or phosphate from being dissolved from underneath the enamel (demineralization) due to organic acid produced by bacteria in dental plaque, acid contained in foods, etc.

The organic acid permeates enamel through gaps between enamel rods which are filled with water, and dissolves hydroxyapatite by a process called demineralization. A loss of calcium and phosphate from enamel tissues leads to the development of initial dental caries under the surface layer of enamel. As described below, according to the present invention, dental caries in the above-described stage can be repaired. Calcium and phosphate ions permeate the dental caries portion under the enamel surface and lost apatite can be restored by a process called remineralization.

Each time that the diet containing fermentative carbohydrates is taken in, the pH of plaque becomes acidic and exceeds a critical pH at which demineralization begins. This results from the action of acid-producing bacteria in the plaque. When the plaque is buffered by saliva, the pH of the plaque is returned to neutral, and calcium and phosphate ions in saliva are reincorporated into dentin through the plaque (this process is called remineralization).

Therefore, means for preventing and treating tooth decay should not be a nutrient for oral bacteria which cause dental caries to allow the bacteria to produce organic acid; should not be a nutrient for mutans bacteria which cause dental caries to allow the bacteria to produce water-insoluble glucan and organic acid; should prevent pH reduction due to the organic acid from going below the pH at which demineralization begins (e.g., should have a buffering ability so as to prevent the pH reduction); should promote remineralization; and the like.

To date various anti-dental caries agents have been known.

Dental caries begin when mutans bacteria produce water-insoluble glucan using sucrose as a nutrient and glycosyl-transferase as an enzyme. This glucan covers the tooth surface, resulting in dental plaque. When the mutans bacteria undergo acid fermentation within the dental plaque, the teeth is dissolved away and tooth decay is formed.

As anti-dental caries saccharides, some oligosaccharides which are not a nutrient for mutans bacteria have already been proposed (S. Hamada et al., J. Jpn. Soc. Starch Sci., Vol. 31, pp. 83-91, 1984). One example of these anti-dental caries saccharides is palatinit (Japanese Laid-Open Publication No. 2000-281550). When palatinit is combined with fluorine or zinc, the remineralization of teeth is promoted (Japanese Laid-Open Publication No. 2000-247852). However, palatinit has poor sweetness and is not preferable for foods. Further, a concentration of as high as about 1 to 20 wt % is required for the remineralization effect of palatinit.

Sugaralcohol (particularly, xylitol) is also known as an anti-dental caries agent (e.g., Japanese Laid-Open Publication No. 2000-128752 and Japanese Laid-Open Publication No. 2000-53549). Japanese Laid-Open Publication No. 11-12143 discloses an oral composition comprising one or more sugar alcohols selected from xylitol, mannitol, galactitol, and inositol. Japanese Laid-Open Publication No. 11-12143 describes that these sugar alcohols can promote the remineralization of teeth, but do not inhibit the growth of the bacteria. Although sugar alcohol is effective only at high concentrations, it is known that the intake of the sugar alcohol in a large amount causes loose stool. As described in the Examples below, the effect of xylitol was not substantially confirmed.

Further, polyphenol which is a component of tea has been reported and utilized as an anti-dental caries agent (S.

Sakanaka et al., Fragrance Journal, Vol. 11, pp. 42-49, 1990). However, use of polyphenol also causes a problem with taste and is therefore limited.

At present, fluorine is said to be most effective for the remineralization effect. Fluorine can exert sufficient efficacy at about 2 ppm. In regard to the efficacy of fluorine, the following two points have been clarified: (1) promotion of remineralization; and (2) fluorine is incorporated into a hydroxyapatite crystal which is in turn converted to a hard crystal structure which resist demineralization (fluorine is used in expectation of effect (2) rather than (1)). Fluorine having such properties has been recently added to various oral compositions. For example, Japanese Laid-Open Publication No. 11-130643 discloses an oral composition containing calcium carbonate and a soluble fluoride compound. It is known that a combination of fluoride ions with sugar alcohol enhances the ability of fluorine to remineralize teeth (For example, Japanese Laid-Open Publication No. 11-21217, Japanese Laid-Open Publication No. 2000-72638, and Japanese Laid-Open Publication No. 2000-154127). Japanese Laid-Open Publication No. 8-12541 discloses a composition containing mutanase and a fluoride compound, which enhances dentin and promotes remineralization to effectively prevent dental caries.

It is known in the art that supply of calcium phosphate promotes the remineralization of teeth (e.g., Japanese Laid-Open Publication No. 11-228369 and Japanese Laid-Open Publication No. 10-310513).

Japanese Laid-Open Publication No. 11-29454 discloses an oral composition containing calcium carbonate and alginate. This composition enhances the ability of calcium carbonate to adhere and remain on teeth so that satisfactory naturalization of pH and promotion of remineralization are obtained, resulting in an excellent dental caries-preventing effect.

Japanese Laid-Open Publication No. 8-104696 describes that phosphorylated oligosaccharides disclosed therein suppress calcium and phosporus from being deposited and crystallized (i.e., calcification), that the phosphorylated oligosaccharides are not a nutrient for mutans bacteria which cause dental caries so that water-insoluble glucan is not produced, and that the phosphorylated oligosaccharides have a buffering ability and have the effect of preventing pH reduction. The above-described properties prevent the development of dental calculus and dental plaque, and the acid fermentation by mutans bacteria. It is also disclosed that phosphorylated oligosaccharides contained in a dietary composition or an oral composition have the effect of preventing pH reduction due to lactic acid, which is a product of fermentation within dental plaque, without an influence on flavor. However, Japanese Laid-Open Publication No. 8-104696 does not suggest that the above-described phosphorylated oligosaccharides can have the remineralization effect at a low concentration as described herein.

DISCLOSURE OF THE INVENTION

Therefore, the present invention relates to materials having an anti-dental caries function. Particularly, the objective of the present invention is to provide dietary compositions and oral compositions which reduce the development of dental caries by the remineralization of teeth or the like.

The inventors have rigorously studied a technique for preventing dental caries by using various substances. As a result, the inventors found a buffering agent having a remineralization effect on teeth, and completed the present invention.

According to one aspect of the present invention, a dietary composition has an anti-dental caries function. The composition comprises a buffering agent having a pH buffering action in the oral cavity.

In one embodiment of this invention, the buffering agent is a phosphorylated oligosaccharide or sugar alcohol thereof.

In one embodiment of this invention, the buffering agent is selected from the group consisting of: phosphorylated oligosaccharides or sugar alcohol thereof, in which the phosphorylated oligosaccharides are glucan consisting of 3 to 5 glucoses with α-1,4 linkages, one phosphate group being linked to the glucan, or glucan consisting of 2 to 8 glucoses with α-1,4 linkages, two phosphate groups being linked to the glucan; chondroitin sulfate; chondroitin sulfate oligosaccharides; glucose-6-phosphate; oligogalacturonic acid; and tartaric acid.

In one embodiment of this invention, the buffering agent is a phosphorylated oligosaccharide or sugar alcohol thereof. The phosphorylated oligosaccharides are glucan consisting of 3 to 5 glucoses with α-1,4 linkages, one phosphate group being linked to the glucan, or glucan consisting of 2 to 8 glucoses with α-1,4 linkages, two phosphate groups being linked to the glucan.

In one embodiment of this invention, the buffering agent is in the form of an alkaline metal salt, an alkaline earth metal salt, or an iron salt.

In one embodiment of this invention, the buffering agent is in the form of a sodium salt or a calcium salt.

In one embodiment of this invention, the dietary composition further comprises an effective amount of fluorine or a fluorine containing substance for anti-dental caries.

According to another aspect of the present invention, a dietary composition has an anti-dental caries function. The composition comprises a buffering agent having a pH buffering action in the oral cavity, a phosphorus-calcium compensating agent, a phosphorus preparation, and/or a calcium preparation.

In one embodiment of this invention, the buffering agent is a phosphorylated oligosaccharide or sugar alcohol thereof.

In one embodiment of this invention, the buffering agent is selected from the group consisting of: phosphorylated oligosaccharides or sugar alcohol thereof, in which the phosphorylated oligosaccharides are glucan consisting of 3 to 5 glucoses with α-1,4 linkages, one phosphate group being linked to the glucan, or glucan consisting of 2 to 8 glucoses with α-1,4 linkages, two phosphate groups being linked to the glucan; chondroitin sulfate; chondroitin sulfate oligosaccharides; glucose-6-phosphate; oligogalacturonic acid; and tartaric acid.

In one embodiment of this invention, the buffering agent is a phosphorylated oligosaccharide or sugar alcohol thereof. The phosphorylated oligosaccharides are glucan consisting of 3 to 5 glucoses with α-1,4 linkages, one phosphate group being linked to the glucan, or glucan consisting of 2 to 8 glucoses with α-1,4 linkages, two phosphate groups being linked to the glucan.

In one embodiment of this invention, the buffering agent is in the form of an alkaline metal salt, an alkaline earth metal salt, or an iron salt.

In one embodiment of this invention, the buffering agent is in the form of a sodium salt or a calcium salt.

In one embodiment of this invention, the dietary composition further comprises an effective amount of fluorine or a fluorine containing substance for anti-dental caries.

According to another aspect of the present invention, an oral composition has an anti-dental caries function. The composition comprises a buffering agent having a pH buffering action in the oral cavity.

In one embodiment of this invention, the buffering agent is a phosphorylated oligosaccharide or sugar alcohol thereof.

In one embodiment of this invention, the buffering agent is selected from the group consisting of: phosphorylated oligosaccharides or sugar alcohol thereof, in which the phosphorylated oligosaccharides are glucan consisting of 3 to 5 glucoses with α-1,4 linkages, one phosphate group being linked to the glucan, or glucan consisting of 2 to 8 glucoses with α-1,4 linkages, two phosphate groups being linked to the glucan: chondroitin sulfate; chondroitin sulfate oligosaccharides; glucose-6-phosphate; oligogalacturonic acid; and tartaric acid.

In one embodiment of this invention, the buffering agent is a phosphorylated oligosaccharide or sugar alcohol thereof. The phosphorylated oligosaccharides are glucan consisting of 3 to 5 glucoses with α-1,4 linkages, one phosphate group being linked to the glucan, or glucan consisting of 2 to 8 glucoses with α-1,4 linkages, two phosphate groups being linked to the glucan.

In one embodiment of this invention, the buffering agent is in the form of an alkaline metal salt, an alkaline earth metal salt, a zinc salt, or an iron salt.

In one embodiment of this invention, the buffering agent is in the form of a sodium salt, a calcium salt, or a zinc salt.

In one embodiment of this invention, the oral composition further comprises an effective amount of fluorine or a fluorine containing substance for anti-dental caries.

According to another aspect of the present invention, an oral composition has an anti-dental caries function. The composition comprises a buffering agent having a pH buffering action in the oral cavity, a phosphorus-calcium compensating agent, a phosphorus preparation, and/or a calcium preparation.

In one embodiment of this invention, the buffering agent is a phosphorylated oligosaccharide or sugar alcohol thereof.

In one embodiment of this invention, the buffering agent is selected from the group consisting of: phosphorylated oligosaccharides or sugar alcohol thereof, in which the phosphorylated oligosaccharides are glucan consisting of 3 to 5 glucoses with α-1,4 linkages, one phosphate group being linked to the glucan, or glucan consisting of 2 to 8 glucoses with α-1,4 linkages, two phosphate groups being linked to the glucan; chondroitin sulfate; chondroitin sulfate oligosaccharides; glucose-6-phosphate; oligogalacturonic acid; and tartaric acid.

In one embodiment of this invention, the buffering agent is a phosphorylated oligosaccharide or sugar alcohol thereof. The phosphorylated oligosaccharides are glucan consisting of 3 to 5 glucoses with α-1,4 linkages, one phosphate group being linked to the glucan, or glucan consisting of 2 to 8 glucoses with α-1,4 linkages, two phosphate groups being linked to the glucan.

In one embodiment of this invention, the buffering agent is in the form of an alkaline metal salt, an alkaline earth metal salt, a zinc salt, or an iron salt.

In one embodiment of this invention, the buffering agent is in the form of a sodium salt, a calcium salt, or a zinc salt.

In one embodiment of this invention, the oral composition further comprises an effective amount of fluorine or a fluorine containing substance for anti-dental caries.

According to another aspect of the present invention, a method for investigating a remineralization effect of a sample expected to have an anti-dental caries action on a tooth, comprises the steps of: (A) subjecting a solution containing phosphorus, calcium, and tooth components in the presence of the sample to a calcium precipitation reaction: (B) measuring the concentration of calcium in the solution or the amount of precipitated calcium after the precipitation reaction; (C) subjecting the solution in the absence of the sample to a calcium precipitation reaction; (D) measuring the concentration of calcium in the solution or the amount of precipitated calcium after the precipitation reaction; and (E) comparing the concentration of calcium in the solution or the amount of precipitated calcium in the steps (B) and (D).

In one embodiment of this invention, the solution comprises hydroxyapatite, buffer solution, $KH_2PO_4$ and $CaCl_2$.

BEST MODE FOR CARRYING OUT THE INVENTION

Figure 1:
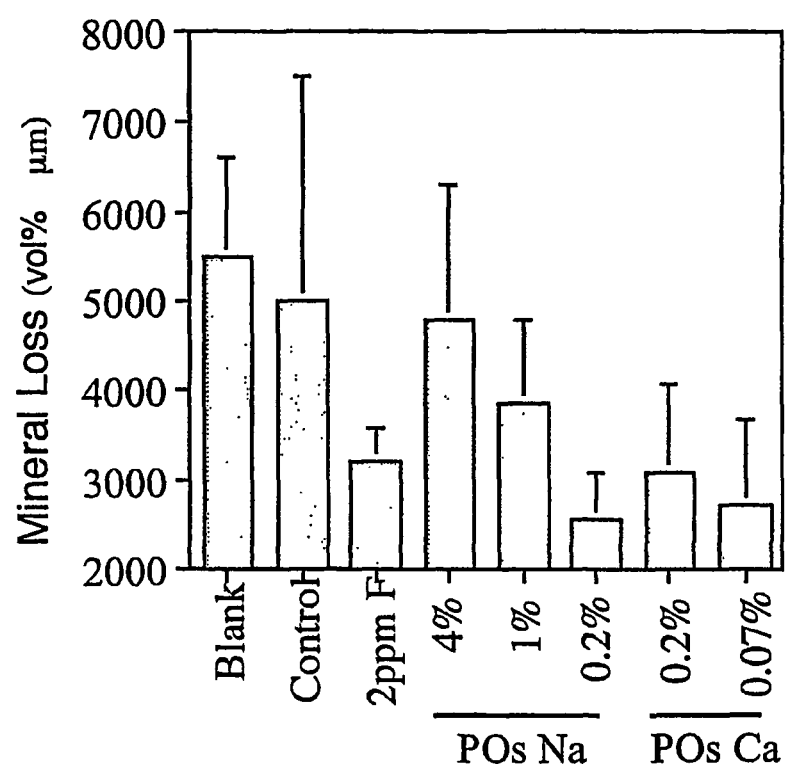
FIG. 1 is a graph showing mineral loss values due to dental caries in a remineralization test system employing bovine teeth sections.

Hereinafter, the present invention will be described in more detail.

The term "anti-caries function" as used herein refers to both functions of preventing dental caries and treating dental caries. The function of treating dental caries means a function of repairing a portion of a tooth which is once lost due to dental caries. The term "anti-dental caries function" as used herein refers to one or more of the following properties: (1) a pH buffering ability to prevent pH reduction due to acids produced by oral bacteria; (2) an ability to prevent oral bacteria from producing insoluble glucan; and (3) an ability to promote remineralization of teeth in early dental caries. Preferably, the anti-caries function has two of the above-described properties, and most preferably all of the above-described properties.

The composition of the present invention can stably provide phosphate and calcium to decayed teeth. The teeth supplied with phosphate and calcium are remineralized, so that a portion of a tooth lost due to dental caries can be repaired.

According to the present invention, a buffering agent is added to the oral cavity, so that phosphate and calcium present in saliva or the like in the oral cavity are stably used in the remineralization of teeth. Therefore, the repair of teeth which are conventionally considered to be difficult or impossible can be realized.

A demineralized lesion can be repaired into a sound state, if calcium or phosphate is supplied to a demineralized enamel portion (remineralization) under appropriate conditions. To maintain the sound state of teeth, minerals need to be supplied to a demineralized lesion by saliva so that demineralization and remineralization are balanced at microscopic levels. Generally, the pH in dental plaque tends to be lowered after eating or drinking, and the balance between demineralization and remineralization is altered. When demineralization>remineralization, the lesion proceeds. Conversely, when remineralization>demineralization, the demineralized lesion is restored due to the remineralization of the tooth. The balance between demineralization and remineralization depends largely on oral environments (particularly, the pHs in saliva and dental plaque, and concentrations of calcium and phosphate). The present invention can provide an oral environment in which remineralization is likely to occur, thereby preventing dental caries and treating demineralized lesions (the early stage of dental caries) to obtain healthy and robust teeth.

The term "buffering agent" as used herein refers to an agent which exhibits a pH buffering action in the oral cavity. Specifically, the buffering agent is a water-soluble salt obtained from the anion or cation of the buffering agent, for example. The presence of the buffering agent in the oral cavity can stabilize the pH in the oral cavity. The buffering agent stabilizes phosphate ions and calcium ions in saliva. Therefore, particularly, an agent which has a good pH buffering action in the presence of phosphate ions and calcium ions is preferable. More preferably, when the buffering agent is added to an aqueous solution containing phosphate ions and calcium ions, the stability of the phosphate ions and calcium ions is not inhibited by the buffering agent. In otherwords, a buffering agent which is likely to react with phosphate ions and calcium ions and form precipitates is not preferable.

Further, in the present invention, the pH buffering effect is preferably obtained in dental plaque. If the pH buffering action is exhibited in saliva, the pH buffering action is typically exhibited in dental plaque. Therefore, a buffering agent which exhibits the pH buffering action in saliva can be used to exhibit the pH buffering action in dental plaque. A hydrogen ion sensitive field effect transistor electrode (PH-6010: manufactured by Nihon Kohden Corporation) may be placed on an enamel section and incorporated into a tooth gap portion of a partial denture for the lower jaw. Thereafter, the pH in dental plaque formed on the sensitive portion of the electrode may be measured in accordance with a method described in Yoshizumi Tamasawa et al. (Journal of the Japan Prosthodontic Society, Vol. 40 special issue, P147, 1996), Kazuhiko Abe (DENTAL OUTLOOK, 90(3), 650-654, 1997), Takahashi-Abbe, S et al (Oral Microbiol. Immunol., 16, P94-99, 2001). The pH in dental plaque is preferably 6 or more, more preferably 7 or more. When the pH of plaque is caused by the buffering action to return to neutral, phosphate ions and calcium ions present in saliva in the oral cavity are supplied to the surface of teeth, resulting in remineralization of dentin. The upper limit of the pH of plaque is not particularly limited, but a high alkaline condition is not intended for an actual organism. The pH of plaque is preferably 10 or less, more preferably 8 or less.

The buffering agent is typically used in the form of a salt, and may be optionally used in the form of a free acid. Even if the buffering agent is provided in the oral cavity in the form of a free acid, since an alkaline metal and the like which can form a salt together with a free acid are present in the oral cavity, it can be substantially said that a salt of the free acid is provided to the oral cavity.

A preferable buffering agent which can be used in the present invention can be easily selected by a simple experiment. Specifically, various known pH buffering agents are added to a neutral aqueous solution (e.g., an aqueous solution of pH 6-8) containing phosphate ions and calcium ions. The presence or absence of precipitation is observed. A pH buffering agent which does not form precipitate in such an experiment can be satisfactorily used as the buffering agent that is added to the anti-caries composition of the present invention.

When a buffering agent is not present, the oral cavity may be acidified due to the effect of organic acids produced by oral bacteria (i.e., saliva or dental plaque becomes acidic). When saliva or dental plaque is acidified, calcium and phosphor of teeth are eluted as Ca and P ions, resulting in the development of dental caries. In this case, if a buffering agent is present, the pH of saliva and dental plaque in the oral cavity becomes stable around neutral pH, whereby formation of dental caries is unlikely to proceed.

The pH of saliva is generally around neutral. Therefore, a buffering agent which has a good buffering act ion at pH around neutral is preferable.

Preferably, the buffering agent is an agent which does not react with phosphate in saliva to form precipitate.

Preferably, the buffering agent is an agent which does not react with calcium in saliva to form precipitate.

Preferably, the buffering agent has an acidic functional group(s).

Preferably, the buffering agent has any of a phosphate group, a carboxy group, and a sulfate group.

Preferably, the buffering agent has three or less acidic functional groups in its molecule, more preferably two or less acidic function groups. When a excessive number of acidic functional groups are present in the molecule, its ability to provide phosphor and calcium to hydroxyapatite is likely to be reduced. For example, phosphorylated oligosaccharides having one or two phosphate group in their molecules have an improved caries treating function over phytic acid having 6 phosphate groups in its molecule. Therefore, buffering agents other than a substance, such as phytic acid, are preferably used.

A buffering agent having an excellent ability to provide phosphor and calcium to hydroxyapatite is preferable. The ability of the buffering agent to provide phosphor and calcium to hydroxyapatite may be easily tested by a simple remineralization test system method as described below.

Examples of the buffering agent include phosphorylated oligosaccharides and sugar alcohols thereof. The term "phosphorylated oligosaccharide" as used herein refers to an oligosaccharide which has at least one phosphate group in its molecule, preferably three or less phosphate groups, and more preferably two or less phosphate groups. The term "neutral oligosaccharide" as used herein refers to an oligosaccharide without a phosphate group linked thereto. For example, the phosphorylated oligosaccharide may be a glucan consisting of 3 to 5 glucoses coupled by α-1,4 linkages where one phosphate group is linked to the glucan. Alternatively, the phosphorylated oligosaccharide may be a glucan consisting of 2 to 8 glucoses with α-1,4 linkages where two phosphate groups are linked to the glucan. Examples of the buffering agent include, but are not limited to, acidic saccharides and sugar alcohols thereof (e.g., oligogalacturonic acid, chondroitin sulfate, chondroitin sulfate oligosaccharides, glucose-6-phosphate), organic acids (e.g., tartaric acid, citric acid, malic acid, lactic acid, fumaric acid, and maleic acid), nucleic acids (e.g., phosphate esters of various nucleosides or nucleotides), amino acids, and the sugar alcohols of the above-described phosphorylated oligosaccharides.

The above-described buffering agents may be in the form of a salt, such as a metal salt, in order to cause the buffering agents to be effective. Examples of a metal which is used for the formation of such a metal salt include alkaline metal, alkaline earth metal, zinc, iron, chromium, and lead. For example, potassium, sodium, calcium, and magnesium are included. As a metal salt of a buffering agent contained in the dietary composition of the present invention, a calcium salt and a sodium salt are preferable. As a metal salt of a buffering salt contained in the oral composition of the present invention, a calcium salt, a sodium salt and a zinc salt are preferable. Although zinc salts are not used for foods and drinks, it is known that zinc salts have the effects of preventing halitosis and treating periodontal disease. Therefore, zinc salts are preferable as metal salts contained for oral compositions. Further, the buffering agent may be in the form of an ammonium salt or a quaternary amine salt.

Chondroitin sulfate typically contains one sulfate group every two sugars. A sulfate group is linked to the 4-position of N-acetyl-D-galactosamine in chondroitin sulfate A, and the 6-position of N-acetyl-D-galactosamine in chondroitin sulfate C. Chondroitin sulfate B (currently called dermatan sulfate) has a repetition structure of disaccharide units of N-acetyl-D-galactosamine-4-sulfate and L-iduronic acid. Chondroitin sulfate can be degraded by chondroitinase up to disaccharides of oligosaccharides having an unsaturated hexuronic acid at a nonreducing terminal. For example, chondroitin sulfate can be degraded up to unsaturated disaccharides having hexosamine at their reducing terminals by chondroitinase ABC (derived from *Proteus vulgaris*), chondroitinase ACI (derived from *Flavobacterium heparinum*), or chondroitinase ACII (derived from *Arthrobacter aurescens*) (the latter two enzymes do not act on dermatan sulfate). Chondroitin sulfate, and unsaturated oligosaccharides (preferably, disaccharide and tetrasaccharide) obtained by degrading chondroitin sulfate with such enzymes have the remineralization effect.

Oligogalacturonic acid is an oligosaccharide of polymerized galacturonic acids which is known as a constituent saccharide of pectin. Oligogalacturonic acid preferably comprises 2 or more saccharides, more preferably 3 or more, even more preferably 4 or more, and preferably 10 or less, more preferably 8 or less, and even more preferably 6 or less.

The term "sugar alcohol" as used herein refers to a sugar whose reducing terminal is reduced. For example, the sugar alcohol of phosphorylated oligosaccharide may be produced by adding hydrogen to the reducing terminal of the phosphorylated oligosaccharide. The addition of hydrogen can be conducted with any method known to those skilled in the art. For example, oligosaccharide can be reduced by preparing a weak alkaline solution of 1 N aqueous sodium hydroxide solution, pH 8, adding 30 ml of 3% sodium boron hydroxide solution to 100 ml of the weak alkaline solution, and allowing the mixture to stand at 40° C. for one hour. The sugar alcohol may be industrially produced by a typical method using a nickel catalyst known to those skilled in the art.

As the buffering agent contained in the dietary composition and the oral composition of the present invention, phosphorylated oligosaccharides which are glucans consisting of 3 to 5 glucoses coupled by α-1,4 linkages where one phosphate group is linked to the glucans, or phosphorylated oligosaccharides which are glucans consisting of 2 to 8 glucoses with α-1,4 linkages where two phosphate groups are linked to the glucans, are preferable.

Such phosphorylated oligosaccharides can be prepared from general crude plant starch, and preferably starch having a number of phosphate groups. Examples of starting plants for starch which is used to produce phosphorylated oligosaccharides include potato, sweet potato, cassava, maize, wheat, rice, waxy rice, waxy maize, waxy wheat, waxy potato, kudzu, yam, lily, and chestnut. Among these things, the underground stems, rice, wheat, etc. contain much linked phosphate groups and are suitable for materials for phosphorylated oligosaccharides. For example, in potato starch, a phosphate group is relatively often bound by an ester linkage to the 3-position or 6-position of glucose as a constituent of the starch. A phosphate group is mainly present in amylopectin. As starch used to produce phosphorylated oligosaccharides, chemically modified starch may also be preferably used. Chemically modified starch is obtained by linking phosphorus to native starch as described above. For example, starch from maize, waxy maize, or the like is chemically coupled with phosphor to prepare phosphorylated oligosaccharides.

The above-described phosphorylated oligosaccharides which are contained in the dietary compositions and oral compositions of the present invention may be produced as follows.

In order to enzymatically degrade starch or the like, at least one selected from the group consisting of amylolytic enzymes such as α-amylase (EC 3.2.1.1), β-amylase (EC 3.2.1.2), glucoamylase (EC 3.2.1.3), isoamylase (EC 3.2.1.68), pullulanase (EC 3.2.1.41), and neopullulanase (Kuriki et al., Journal of Bacteriology, vol. 170, pp. 1554-1559, 1988); and glycosyltransferase such as cyclodextrin glucanotransferase (EC 2.4.1.19; hereinafter, referred to as CGTase) is allowed to act on the starch. Alternatively, at least one of those enzymes is used in combination with α-glucosidase (EC 3.2.1.20).

Phosphorylated saccharide having no branch structure can be obtained by degrading starch with isoamylase or pullulanase to cleave the α-1,6 branch structure in the starch. If isoamylase or pullulanase is not used, phosphorylated saccharide having an α-1,6 branch structure can be obtained. By degrading phosphorylated saccharide with glucoamylase, non-phosphorylated glucoses which are linked to nonreducing terminals of the phosphorylated saccharide can be successively liberated. With such an enzyme treatment, the number of phosphate groups per unit molecular weight of purified phosphorylated saccharide can be either increased or decreased.

Degradation by a plurality of kinds of enzymes can be concurrently performed by allowing the enzymes to simultaneously react with starch. Briefly, starch as raw material is dissolved in water or a buffer with pH which is adjusted so that the enzymes can act on starch. Liquefying α-amylase, pullulanase, glucoamylase, etc. are simultaneously added to a reaction solution, and the resulting solution is allowed to react while heating. With this method, while starch is being gelatinized, neutral saccharide can be liberated, non-phosphorylated glucose which is bound to a nonreducing terminal of phosphorylated saccharide can be liberated, or α-1,6 branch structure derived from a material in phosphorylated saccharide structure can be cleaved. This method makes it possible to obtain phosphorylated saccharide with an increased phosphate content by a one-step reaction, rather than a two-step reaction.

In the case where an enzyme reaction including two or more steps is conducted by allowing a plurality of kinds of enzymes to separately act on starch in respective steps, the sequence of application of the enzymes is not limited to a particular order. However, if the concentration of the starch is high, it is preferable that the starch is first treated by enzymes including liquefying amylase. If isoamylase or pullulanase is allowed to act on the starch, the amylose content increases. Amylose is likely to age and precipitate as compared to amylopectin and, therefore, the starch ages and precipitates. As a result, the other enzymes no longer act on the starch.

There is no particular limit to the origins of starch degrading enzymes, glycosyltransferase, and α-glucosidase to be used. For example, α-amylase is preferably a starch degrading enzyme preparation derived from bacteria of the genus Bacillus or Aspergillus. The reaction conditions for the enzymes are any temperature and pH at which the enzymes can function. For example, a temperature in the range of 25° C. to 70° C., and pH in the range of 4 to 8 are preferably used.

First, starch as a raw material is dissolved in water or a buffer with pH which is adjusted so that the enzymes can act on the starch. Liquefying α-amylase is added to the resulting solution and allowed to react while heating, whereby the starch is liquefied while being gelatinized. Thereafter, the liquefied starch is held at a temperature of 20 to 80° C. for an appropriate period of time. Any amount of the liquefying α-amylase can be used as long as it can liquefy the starch. A preferable amount of the liquefying α-amylase is 20 to 50,000 U. This holding time is not limited as long as the starch is liquefied to a degree that the starch will not age during the subsequent steps. Preferably, the holding time is 30 minutes at a temperature of 20 to 80° C.

After completion of the liquefaction, inactivation of the enzyme is not particularly required, but the enzyme may be inactivated by a commonly used method, i.e., by being held at 100° C. for 10 minutes. Further, insoluble substances may be separated and removed using a commonly used method, such as centrifugation or film filtration. Thereafter, phosphorylated saccharide can be fractionated. When phosphorylated saccharide with an increased phosphate content is desired, the additional steps described below are conducted.

Briefly, after the material is liquefied, glucoamylase, isoamylase, pullulanase, and α-glucosidase are added to the liquefied material simultaneously or in an appropriate order so as to saccharify the material. The saccharified material is allowed to react at a temperature of 40 to 60° C. for 30 minutes to 40 hours, for example, whereby neutral saccharide and non-phosphorylated glucose which is linked to a non-reducing terminal of phosphorylated saccharide can be liberated from the material, and α-1,6 branch structure in the phosphorylated saccharide structure derived from the material can be cleaved. When glucoamylase, isoamylase, and pullulanase are used in combination, the combination and the sequence of addition thereof are not limited. The amount of additive enzymes and the holding time can be determined depending on the required phosphate content of phosphorylated saccharide. Preferably, 50 to 700 U of glucoamylase, 2 to 100 U of isoamylase, 2 to 100 U of pullulanase, and 50 to 700 U of α-glucosidase can be added. Immobilized enzymes can be preferably used.

After completion of the reaction with each enzyme, inactivation of the enzyme is not particularly required, but it may be inactivated by a commonly used method, i.e., by being held at 100° C. for 10 minutes. Further, insoluble substances may be separated and removed using a commonly used method, such as centrifugation or membrane filtration.

In order to purify phosphorylated oligosaccharides from a saccharide mixture containing phosphorylated oligosaccharides, an anion exchange resin can be used since the phosphorylated saccharides are ionic substances unlike neutral saccharide. There is no particular limit to the type of the resin. Preferable examples of the resin include Chitopearl BCW 2500 type (produced by Fuji Spinning Co., Ltd.), Anberlite IRA type (produced by Japan Organo Co., Ltd.), DEAE-cellulose (produced by Whatman), DEAE-Sephadex and QAE-Sephadex (produced by Pharmacia), and QAE-CELLULOSE (produced by Bio Rad). The resin is equilibrated by using a buffer whose pH has been appropriately adjusted. For example, an about 10 to 50 mM acetate buffer (pH 4-5) is preferably used. The equilibrated resin is packed into a column and a saccharide mixture containing phosphorylated oligosaccharides is loaded thereto. Neutral saccharides are removed by washing, and then phosphorylated oligosaccharides adsorbed to the column is eluted with an alkaline solution or a salt solution.

In the case where phosphorylated oligosaccharides are eluted by increasing the ionic strength of an eluent, there is no particular limit to the kind of a salt to be used. Preferable examples of the salt include sodium chloride, ammonium bicarbonate, potassium chloride, sodium sulfate, and ammonium sulfate.

In the case where phosphorylated oligosaccharides are eluted by changing the pH of an eluent into alkaline, there is no particular limit to the kind of an alkaline reagent to be used. For example, ammonia, sodium carbonate, or sodium hydroxide may be used. However, under a strong alkaline condition, phosphate groups are liberated from saccharide or the reducing terminal of the saccharide is oxidized. Therefore, phosphorylated oligosaccharides are eluted preferably in the pH range of weakly acidic to weakly alkaline, and more preferably in the pH range of 3 to 8.

In the above case, by eluting phosphorylated saccharide by increasing the salt concentration or pH of the eluent gradually or in a stepwise manner, the phosphorylated saccharides can be fractionated depending upon the number of phosphate groups bound to one phosphorylated saccharide molecule.

Activated charcoal can also be used instead of an anionic exchange resin to purify phosphorylated oligosaccharides from a saccharide mixture containing phosphorylated oligosaccharides. There is no particular limit to the kind of activated charcoal to be used, but granular activated charcoal capable of being packed into a column is preferably used. Activated charcoal is prepared using a buffer, an acid, an alkali, a salt solution, and distilled water so that an ability to adserb neutral saccharides excluding glucose is obtained. For example, degassed activated charcoal having a uniform grain size which has been packed into the column and washed with distilled water may be preferably used. Phosphorylated oligosaccharides can be obtained as a passed fraction by applying a sample to the column and allowing neutral saccharides to be adsorbed into the column.

Alternatively, phosphorylated oligosaccharides is precipitated by addition of alcohol having 1 to 3 carbon atoms to purify phosphorylated oligosaccharides from a saccharide mixture containing phosphorylated oligosaccharides. Briefly, alcohol is added to a sample solution to allow only phosphorylated oligosaccharides to be precipitated. It is desired that if the sample solution has a saccharide concentration of 10% or more, 3 or more parts by volume of alcohol are added to one part by volume of the sample solution.

Phosphorylated oligosaccharides form phosphorylated saccharide metal salts and are likely to precipitate, in the presence of a metal salt, preferably a calcium salt or an iron salt in addition to alcohol. For this reason, in the presence of a metal salt, phosphorylated oligosaccharides are recovered more easily using even a small amount of alcohol, as compared with the case of using alcohol alone. Preferably, the phosphorylated saccharide is precipitated under an alkaline condition. There is no particular limit to the kind of the salt to be used. For example, calcium chloride, magnesium chloride, or ferrous chloride can be preferably used because of their satisfactory solubility. The collection of a precipitate generated by the addition of alcohol is conducted by a commonly used method, such as decantation, filtration, and centrifugation.

Phosphorylated oligosaccharide may be produced by removing the metal salt from the phosphorylated oligosaccharide metal salt which is precipitated by the addition of the metal salt. The removal of the metal salt (desalting) can be conducted by a commonly used method., The desalting can be easily conducted using, for example, table-top desalting microacilyzer G3 (manufactured by Asahi Chemical Industry Co., Ltd.).

The resultant phosphorylated saccharide solution, phosphorylated saccharide, or phosphorylated saccharide derivative can be condensed or powdered using a commonly used drying method, such as hot-air drying, fluidized-bed drying, and vacuum drying. By removing alcohol, if required, phosphorylated'saccharide which can be used in dietary or oral applications can be obtained.

Figure 26:
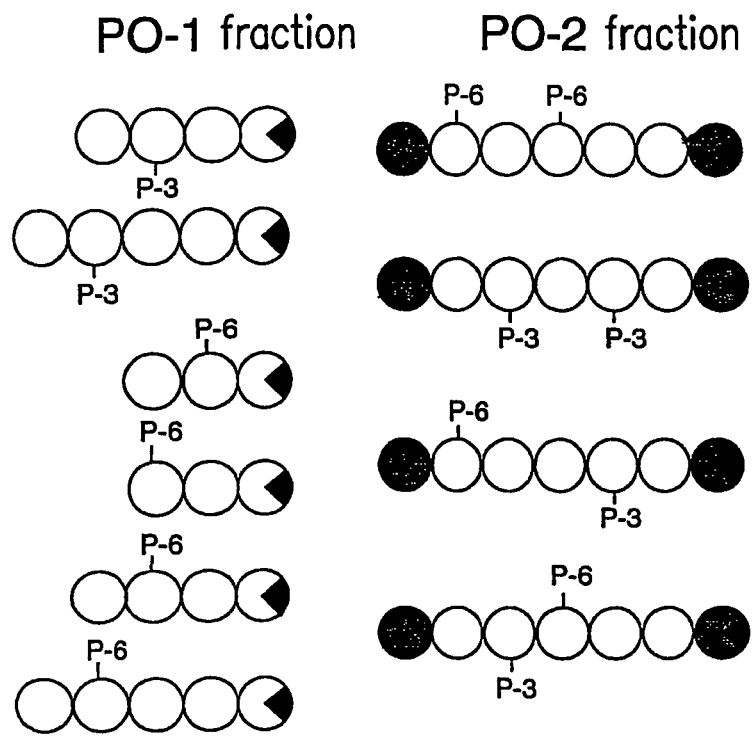
FIG. 26 is a diagram showing the chemical structural formulas of representative phosphorylated oligosaccharides.

In potato starch, a phosphate group is relatively often linked by an ester linkage to the 3-position or 6-position of glucose as a constituent of the starch. Therefore, phosphorylated oligosaccharide prepared from potato starch using various amylases may be an oligosaccharide in which a phosphate group is mainly bound to the 3-position or 6-position of glucose. For example, if a phosphate group is bound to the 6-position of glucose in the phosphorylated oligosaccharide obtained by allowing glucoamylase to act on potato starch, the starch can be cleaved immediately before (at the nonreducing terminal side) the glucose having a phosphate group at its 6-position. Thus, the phosphorylated oligosaccharide is oligosaccharide having glucose with its 6-position bond with a phosphate group at a nonreducing end or has a structure in which the at least second glucose from the nonreducing terminal has its 6-position bond with a phosphate group. If a phosphate group is bound to the 3-position of glucose in the phosphorylated oligosaccharide, the second glucose from the nonreducing terminal has its 3-position bond with a phosphate group. A representative example of phosphorylated oligosaccharide obtained by hydrolyzing potato starch using various amylase is shown in FIG. 26. Of course, phosphorylated oligosaccharide having the above-described structure is not limited to ones that are produced by hydrolyzing potato starch by various amylase. Phosphorylated oligosaccharides having like structure have like anti-dental caries functions.

The term "sugar alcohol of phosphorylated oligosaccharide" as used herein refers to a compound obtained by reducing the reducing terminal of the phosphorylated oligosaccharide. The sugar alcohol of the above-described phosphorylated oligosaccharide may be produced by adding hydrogen to the reducing terminal of the phosphorylated oligosaccharide. The hydrogen addition may be conducted by any method known to those skilled in the art. For example, oligosaccharide can be reduced by preparing a weak alkaline solution of 1 N aqueous sodium hydroxide solution, pH 8, adding 30 ml of 3% sodium boron hydroxide solution, and allowing the mixture to stand at 40° C. for one hour. The sugar alcohol may be industrially produced by a typical method using a nickel catalyst known to those skilled in the art.

The above-described phosphorylated oligosaccharides or sugar alcohols thereof may be in the form of a salt, such as a metal salt. Examples of a metal which is used for the formation of such a metal salt include alkaline metal, alkaline earth metal, zinc, iron, chromium, and lead. For example, potassium, sodium, calcium, and magnesium are included. As metal salts of phosphorylated oligosaccharides contained in the dietary composition of the present invention, a calcium salt and a sodium salt are preferable. As metal salts of phosphorylated oligosaccharides contained in the oral composition of the present invention, a calcium salt, a sodium salt and a zinc salt are preferable. Although zinc salts are not used for foods and drinks, it is known that zinc salts have the effects of preventing halitosis and treating periodontal disease. Therefore, zinc salts are preferable as metal salts contained for oral compositions. Further, the phosphorylated oligosaccharides may be in the form of an ammonium salt or a quaternary amine salt.

Such a metal salt can be produced as follows. A phosphorylated oligosaccharide salt which is a compound of phosphorylated oligosaccharide and a metal salt can be precipitated by alcohol precipitation as described above. If necessary, recovered precipitation may be redissolved in water or an appropriate solution, followed by addition of alcohol. This operation may be repeated. With this operation, impurities such as neutral sugar and excessive salts can be removed. An ultra filtration film may be used to remove impurities such as a salt.

It is known that the above-described phosphorylated oligosaccharide has the following properties: (1) not to be utilized by dental caries pathogenic bacteria (e.g., mutans streptococci and sobrinus streptococci); (2) to suppress a reduction in pH due to sucrose utilization by these bacteria in a concentration-dependent manner; and (3) this suppression relies on the buffering ability of the phosphorylated oligosaccharide (see Japanese Laid-Open Publication No. 8-104696). According to the present invention, it was further found that the salt-form phosphorylated oligosaccharide and the sugar alcohol thereof have the effect of promoting remineralization of teeth at a very low concentration. By utilizing such properties of phosphorylated oligosaccharide, dietary compositions and oral compositions having an anti-dental caries function can be obtained. In particular, the fact that the remineralization effect is sufficiently obtained at a low concentration is very preferable for addition to foods.

The dietary compositions and oral compositions of the present invention contain a buffering agent in an amount such that the buffering agent effectively exhibits an anti-dental caries function in the oral cavity. For example, in the case of a phosphorylated oligosaccharide sodium salt, the amount may be such that the concentration of the salt in the oral cavity is 0.01 to 20%, and preferably 0.03 to 1%. For example, in the case of a phosphorylated oligosaccharide calcium salt, the amount may be such that the concentration of the salt in the oral cavity is 0.01 to 20%, and preferably 0.03 to 1%. For example, in the case of a phosphorylated oligosaccharide zinc salt, the amount may be such that the concentration of the salt in the oral cavity is 0.01 to 20%, and preferably 0.03 to 1%. For all the phosphorylated oligosaccharide sodium salt, the phosphorylated oligosaccharide calcium salt, and the phosphorylated oligosaccharide zinc salt, and most preferably, their concentrations in the oral cavity are about 0.2% where the inorganic calcium and phosphorus concentrations are about 1.5 mM and 0.9 mM in the oral cavity.

The amounts of these additives may be determined by taking into consideration the holding times in the oral cavity of the dietary compositions and oral compositions of the present invention. An will be given for the case of the dietary compositions which require mastication behaviors. For example, in the case of a chewing gum containing about 20% phosphorylated oligosaccharide, phosphorylated oligosaccharide is eluted from the dietary composition and a relatively high concentration (about 1% to about 5%) of the phosphorylated oligosaccharide can be present for about 10 minutes after mastication. After about 20 minutes to 30 minutes, only 0.25% or less phosphorylated oligosaccharide is present in the oral cavity. Therefore, the concentration of phosphorylated oligosaccharide in the oral cavity is diluted to one fourth or less of the concentration in the food. Therefore, in the case of such a food, a buffering agent may be added to a food at a concentration which is four times or less the intended concentration in the oral cavity (e.g., one to four times). On the other hand, in the case of compositions which do not require mastication behaviors (e.g., drinks), the holding time in the oral cavity is within one minute. Such compositions are not substantially diluted in the oral cavity. Therefore, phosphorylated oligosaccharide is incorporated into a composition at a concentration which is substantially equal to the intended concentration in the oral cavity (e.g., 0.1% to 5.0%). The dietary compositions and oral compositions of the present invention can contain the above-described buffering agents alone or in combination so that the above-described amount of the agents in the oral cavity can be held.

In another aspect, the dietary compositions and oral compositions of the present invention further contain any one of a phosphorus-calcium compensating agent, a phosphorus preparation, and a calcium preparation, or alternatively a combination of one or more thereof in addition to the above-described buffering agent. In particular, when the composition contains a calcium salt, an extra amount of calcium is released from the calcium salt, so that the ratio of calcium to phosphorus in the composition is changed. Further, the buffering agent added may have an influence on elution of calcium from teeth. In this case, if the ratio of phosphorus to calcium concentrations in saliva of the oral cavity which is changed by the buffering agent is compensated, remineralization of teeth can be more effective. In the case of a normal human, the mole ratio of phosphorus to calcium in saliva (hereinafter referred to as "Ca/P") is generally 0.25 to 0.67 (P/Ca=1.45 to 3.9) and, thus, phosphorus is present more than calcium (i.e., nearly 3 mole phosphorus to 2 mole calcium to 3.9 mole phosphorus to 1 mole calcium). Hydroxyapatite which is a component of teeth (represented by $Ca_{10}(PO_4)_6(OH)_2$) has a Ca/P of 1.67 (P/Ca=0.6). A composition constituting the enamel of teeth has a Ca/P of 1.0 to 1.67 (P/Ca=0.6 to 1.0). Therefore, by supplying phosphorus and/or calcium along with the buffering agent to bring the Ca/P close to 1.0 to 1.67 (P/Ca=0.6 to 1.0), and preferably 1.67 (P/Ca=0.6), it is possible to promote crystallization of these substances into the hydroxyapatite.

An agent which can compensate for Ca/P is herein called a "phosphorus-calcium compensating agent". Examples of such a phosphorus-calcium compensating agent include calcium phosphate monobasic {calcium bis (dihydrogenphosphate)monohydrate}, calcium phosphate dibasic (calcium hydrogenphosphate dihydrate), calcium phosphate tribasic, calcium pyrophosphate, hydroxyapatite powder, amorphous calcium phosphate, bovine bone calcium, eggshell calcium, coral calcium, pearl calcium, fish and shell fish calcium, and α-tribasic calcium phosphate. To compensate for Ca/P herein means to maintain Ca/P within a range which can be substantially approximated to 1.0 to 1.67 (P/Ca=0.6 to 1.0). In this case, Ca/P need not be strictly 1.0 to 1.67 (P/Ca=0.6 to 1.0). Ca/P may fall outside the range of 1.0 to 1.67(P/Ca=0.6 to 1.0) as long as Ca/P can be substantially approximated to be approximately 1.0 to 1.67 (P/Ca=0.6 to 1.0). The amount of a compensating agent required for compensation varies depending on the kinds of a buffering agent and a compensating agent, but the range of such an amount can be determined by those skilled in the art conducting a simple experiment if necessary. In the case of a phosphorus-calcium compensating agent, its appropriate amount is 1/20 parts to 20 parts by mole with respect to one parts of a buffering agent added, and preferably 1/2 parts to 2 parts.

Since phosphorus is excessive in saliva, a calcium preparation may be used to adjust Ca/P to 1.0 to 1.67 (P/Ca=0.6 to 1.0). In human saliva, the phosphorus concentration is 3 to 3.5 mM and the calcium concentration is 0.9 to 2 mM. Therefore, calcium is preferably added at about 4 to 5 mM to increase the calcium concentration. Therefore, a calcium salt (buffering agent) can be used as a phosphorus-calcium compensating agent. In the case of phosphorylated oligosaccharide containing 3% calcium, addition of about 0.7% phosphorylated oligosaccharide calcium is appropriate. Preferable examples of the calcium preparation include, but are not limited to, calcium carbonate, calcium chloride, calcium lactate, calcium gluconate, whey calcium, organic acid calcium, colloidal calcium carbonate, casein phosphopeptide calcium, and calcium fluoride.

The dietary compositions and oral compositions of the present invention may further contain a phosphorus preparation. The term "phosphorus preparation" as used herein refers to a phosphate compound. Examples of the phosphate compound include sodium phosphate, sodium hydrogenphosphate, potassium phosphate, and potassium hydrogenphosphate.

The above-described phosphorus-calcium compensating agent, phosphorus preparation, or calcium preparation may be added alone or in combination to the dietary compositions and oral compositions of the present invention so as to bring Ca/P close to 1.0 to 1.67 (P/Ca=0.6 to 1.0), and preferably 1.67 (P/Ca=0.6).

The term "dietary composition" as used herein is a generic name for human foods, feeds for animals or fish breeding, and pet foods. Specifically, the dietary compositions of the present invention include liquid and powdered drinks such as coffee, tea, green tea, oolong tea, juice, processed milk, and sports drinks; baked foods such as bread, pizza, and pie; baked confectionery such as cookies, crackers, biscuits, and cake; pastas such as spaghetti and macaroni; noodles such as wheat noodles, buckwheat noodles, and Chinese noodles; sweets such as candy, soft candy, chewing gum, and chocolate; snacks such as rice crackers, and potato chips; frozen confectionery such as ice cream and sherbet; dairy products such as cream, cheese, powdered milk, condensed milk, and milk beverage; Western unbaked confectionery such as jelly, pudding, mousse, and yogurt; Japanese confectionery such as a sweet bun, uirou (square-cut rice cake obtained by adding saccharide to the powder, followed by steaming), rice cake, and ohagi (rice dumpling covered with bean jam or the like); seasonings such as soy sauce, sauce for dipping, soup for noodles, Worcestershire sauce, broth stock, stew stock, soup stock, mixed seasonings, curry powder, mayonnaise, and ketchup; canned or retort foods such as curry, stew, soup, and rice dishes; frozen and refrigerated foods such as ham, hamburg, meat balls, croquette, Chinese-style dumpling, fried rice, and rice ball; marine processed products such as tikuwa (tubular fish paste) and kamaboko (fish paste cake); and rice products such as rice for a picnic lunch and sushi. Furthermore, the dietary compositions of the present invention include formulas, weaning foods, baby foods, pet foods, feeds for animals, sports foods, nutrition auxiliary foods, and health foods, because of its ability to allow calcium to be readily absorbed.

In a preferred embodiment, the foods and drinks are ones that are much masticated in eating, such as gum. In the case of the foods and drinks which are much masticated, a buffering agent is easily diffused in the oral cavity, resulting in a satisfactory effect of anti-dental caries. In the case of the foods and drinks which are much masticated, a buffering agent can be added to the diet preferably at a proportion of 0.1 to 50% by weight, more preferably 0.5 to 20% by weight, even more preferably 0.5 to 10% by weight, and particularly preferably 0.5 to 5% by weight. Specifically, for example, such a food is a gum containing 0.1 to 50% by weight of a buffering agent, or a tablet confectionary, candy, gummy candy, etc. containing 0.1 to 50% by weight of a buffering agent.

In another preferred embodiment, the foods and drinks are ones that do not require mastication in eating, such as drinks (e.g., juice or fresh water). In the case of the foods and drinks that do not require mastication in eating, a buffering agent can be mixed to the diet preferably at a proportion of 0.1 to 70% by weight, more preferably 0.1 to 50% by weight, and even more preferably 0.2 to 5% by weight. Specifically, for example, the diet is juice containing 1 to 30% by weight of a buffering agent. Preferably, the diet is vegetable juice, natural juice, milk beverage, milk, soybean milk, sports drinks, near water drinks, nutritional drinks, coffee beverage, or cocoa which contain 0.1 to 10% by weight of a buffering agent.

In still another preferred embodiment, the foods and drinks are ones that are masticated as much as ordinary staple foods in eating. The foods and drinks are preferably staple foods and drinks. For example, such diet is rice. In the case of the staple foods, since the diet is eaten in an abundant amount, even a small concentration of a buffering agent added advantageously provides the significant and long-term effect of preventing dental caries. In the case of the diet that is masticated as much as ordinary staple foods, a buffering agent can be added to the diet at a proportion of preferably 0.01 to 20% by weight, more preferably 0.02 to 10% by weight, even more preferably 0.03 to 5% by weight, and particularly preferably 0.05 to 3% by weight. Specifically, the diet is, for example, rice containing 0.02 to 10% by weight of a buffering agent, bread containing 0.01 to 20% by weight of phosphorylated oligosaccharide, etc.

Of course, the present invention may be applied to foods and drinks other than those of the above-described preferred embodiments. Specifically, the present invention may be applied to, for example, Chinese noodles containing 0.1 to 20% by weight of a buffering agent, wheat noodles containing 0.1 to 20% by weight of a buffering agent, rice cake containing 0.1 to 20% by weight of a buffering agent, pretzel containing 0.1 to 20% by weight of a buffering agent, agar containing 0.1 to 20% by weight of a buffering agent, jelly containing 0.1 to 20% by weight of a buffering agent, yogurt containing 0.1 to 20% by weight of a buffering agent, cookies containing 0.1 to 20% by weight of a buffering agent, tablet confectionary containing 0.1 to 20% by weight of a buffering agent, tofu containing 0.1 to 20% by weight of a buffering agent, chocolate containing 0.1 to 20% by weight of a buffering agent, rice confectionary containing 0.1 to 20% by weight of a buffering agent, Chinese dumpling containing 0.1 to 20% by weight of a buffering agent, and ham containing 0.1 to 20% by weight of a buffering agent.

The term "oral composition" as used herein refers to any composition, which can be introduced into the oral cavity and can be in contact with teeth, other than foods and drinks. The oral compositions may be drugs or quasi-drugs or other compounds. For example, the "oral compositions" further include cosmetics (more particularly, dentifrices which have the effects of preventing tooth decay, whitening teeth, removing dental plaque, cleansing the oral cavity, preventing halitosis, removing tar, preventing deposition of dental calculus, etc. (which may be acknowledged as cosmetics under the Japanese Pharmaceutical Affairs Law (revised in 2001)). Specifically, the oral compositions of the present invention include, for example, dentifrices, mouthwashes, troches, gargles, gum massage creams, lozenges, artificial saliva, etc.

In one preferred embodiment, the oral compositions of the present invention are dentifrices containing preferably 0.01 to 20% by weight of a buffering agent, more preferably 0.02 to 10% by weight, even more preferably 0.03 to 5% by weight, and particularly preferably 0.05 to 3% by weight.

In one preferred embodiment, the oral compositions of the present invention are mouthwashes containing preferably 0.01 to 20% by weight of a buffering agent, more preferably 0.02 to 10% by weight, even more preferably 0.03 to 5% by weight, and particularly preferably 0.05 to 3% by weight.

In one preferred embodiment, the oral compositions of the present invention are oral ointments containing preferably 0.01 to 20% by weight of a buffering agent, more preferably 0.02 to 10% by weight, even more preferably 0.03 to 5% by weight, and particularly preferably 0.05 to 3% by weight.

Preferably, the oral compositions of the present invention are dentifrices, mouthwashes, troches, gargles, artificial saliva, etc. containing 0.1 to 20% by weight of a buffering agent.

The artificial saliva has been used to improve xerostomia. The artificial saliva contains substantially the same components, such as minerals, as human saliva. The artificial saliva containing the above-described buffering agent not only can wet the tongue and the laryngeal mucosa to allow the tongue and the laryngeal mucosa to move smoothly, but also can prevent and treat dental caries.

The dietary compositions and oral compositions of the present invention further optionally contain fluorine. The dietary compositions and oral compositions of the present invention contain within the range of 1000 ppm or less, preferably 0.1 to 500 ppm and more preferably 0.1 to 300 ppm. A buffering agent is suitable for drugs, quasi-drugs, and cosmetics in order to increase the effectiveness of fluorine of 100 ppm or more. The dietary compositions and oral compositions of the present invention can have a higher level of remineralization effect for teeth by further containing fluorine. Here, "fluorine" includes fluorine ion. The term "fluorine containing substance" refers to any material which provides fluorine ion, preferably fluorine ion containing compounds (e.g., sodium monofluorophosphate, sodium fluoride, potassium fluoride, ammonium fluoride, amine salt fluoride, and stannous fluoride). Use of sodium monofluorophosphate and sodium fluoride are preferable.

Use of only fluorine or a fluorine containing substance results in a low level of remineralization of teeth. Particularly, fluorine and a fluorine containing substance are likely to be insoluble at a high concentration of 100 ppm or more, resulting in a significant reduction in the effectiveness. However, in the present invention, it was found that use of a buffering agent along with fluorine or a fluorine containing substance leads to an increase of the effectiveness. As to foods, tea containing a high amount of fluorine (200 to 300 ppm) and the like are preferable. Fluorine or a fluorine containing substance is incorporated into the crystal of teeth to produce the strong crystal resistant to acids. Therefore, the dietary compositions and oral compositions of the present invention are involved in the production of the strong crystal of teeth as well as the remineralization of teeth, thereby reducing the development of dental caries.

The dietary compositions and oral compositions of the present invention may further contain other substances which it is known to those skilled in the art that have an anti-dental caries function. Examples of such a substance include various oligosaccharides (panose ($6^2$-glucosyl-maltose), isomaltooligosaccharides, palatinose (6-O-α-D-Glucopyranosyl-D-Fructofuranose), trehalose (O-α-D-Glucopyranosyl(1-1)-α-D-Glucopyranoside), maltooligosaccharides, Lactosucrose™ ($4^G$-β-D-Galactosylsucrose), fructooligosaccharides, coupling sugars, xylosylfructoside, cyclodextrin, etc.); sugar alcohols (xylitol, erythritol, palatinit, sorbitol, maltitol, mannitol, etc.); tea extracts (fluorine, polyphenol, catechin, etc.); herbs (e.g., mint, peppermint oil, camomile, sage, ginger, rosemary, etc., see Shibuyaetal., FRAGRANCE JOURNAL SPECIAL ISSUE, 12, P150-155, 1992); enzymes (e.g., dextranase,mutase, etc.); andvaccines (e.g., secreted immunogloblin A against mutans streptococci). Sugar alcohols are preferable. Xylitol is more preferable. The dietary compositions and oral compositions of the present invention can have the increased effect of preventing dental caries by containing the above-described substances.

The remineralization effect of a buffering agent may be examined by a known method, such as a remineralization test system using bovine tooth sections which is described in Inaba. D et al., Eur. J. Sci. 105:74-80, 1997; Inaba. D et al., J. Dent. Health. 47:67-74, 1997; and Iijima. Y et al., Dental Caries Research. 33:206-213, 1999.

To examine the remineralization effect of a buffering agent contained in the dietary compositions and oral compositions of the present invention, the inventors of the present invention have developed a simpler test system compared to the above-described remineralization test system. Conditions under which remineralization easily occurs are, for example, the following: quick supply of calcium and phosphorus to the contact surface of the tooth surface (hydroxyapatite) and incorporation of them into a component of teeth (hydroxyapatite); maintenance of higher calcium or phosphorus concentration in a system including the tooth surface; and no deposition or loss of calcium and phosphorus at a place other than the tooth surface. These conditions for easy remineralization are simplified as follows: in a system including hydroxyapatite, calcium and phosphorus are supplied for crystallization and soluble calcium is reduced; and in a system including no hydroxyapatite, phosphorus and calcium are not deposited and the high solubility thereof is maintained. Therefore, the magnitudes of the solubility of calcium in the two systems were compared to examine the remineralization effect. These simple test systems will be described below. TMR (Transversal microradiography) method has been used in a number of researches on demineralization and remineralization as a standard method for measuring the distribution of dentin mineral concentration in a quantitative manner. For this method, there are the following constraints: a long time required for evaluation; a high-level experimental technique required; etc. Therefore, there is a demand for a simple evaluation system capable of quickly capturing changes in dentin mineral concentrations. Remineralization in an early dental caries lesion in the enamel of teeth is considered to develop via the following two processes:

(i) calcium (Ca) ions and phosphor (P) ions which are constituents of enamel are supplied to a demineralized portion; and (ii) the supplied Ca ions and P ions are used in the crystal growth of enamel in the demineralized portion.

Considering the above-described two processes, a substance having the effect of promoting remineralization is considered to be one that inhibits insolubilization and precipitation of Ca and P but does not inhibit the crystal growth of hydroxyapatite under neutral pH.

These test systems have a correlation with the above-described conventional system using bovine teeth, and constitute a simple and excellent method.

In one aspect of the present invention, the present invention relates to a method for investigating the remineralization effect on teeth of a sample which is expected to have an anti-dental caries action. This method comprises the steps of: (A) precipitating calcium in a solution containing phosphorus, calcium, and tooth components in the presence of the sample; (B) measuring a calcium concentration in the solution or the amount of the precipitated calcium after the precipitation; (C) precipitating calcium in the solution in the absence of the sample; (D) measuring a calcium concentration in the solution or the amount of the precipitated calcium after the precipitation; and (E) comparing calcium concentrations or the amounts of the precipitated calcium in steps (B) and (D). In a preferred embodiment, the above-described solution may contain hydroxyapatite, a buffer, $KH_2PO_4$ and $CaCl_2$. The "tooth component" to be contained in the above-described solution is any material that precipitates phosphorus and calcium to produce hydroxyapatite due to remineralization. Use of hydroxyapatite is preferable. Alternatively, teeth of mammals such as a bovine, and sections or fractions thereof may be used. When the solution for calcium precipitation is prepared, the sequence of addition of the above-described phosphorus, calcium, and the other tooth components is not limited. Preferably, first the sample, then, phosphorus, calcium chloride solution, and the tooth component suspension or deionized water are added in this order to prepare the solution. The pH of the solution is preferably adjusted after the addition of $KH_2PO_4$. Calcium precipitation typically occurs by incubation at room temperature for ten and several hours to several days (preferably 10 hours to 7 days, more preferably 18 hours to 42 hours). The calcium solubility of the solution can be measured by any procedure known to those skilled in the art. The calcium solubility of the solution may be measured by OCPC method (using calcium C test Wako manufactured by Wako Pure Chemicals). Alternatively, the amount of precipitated calcium in the solution can be measured. The amount of precipitated calcium in the solution may be measured by any procedure known to those skilled in the art. The calcium solubility of the solution may be measured by any procedure known to those skilled in the art. Examples of such a method include the ICP method (Inductive Coupled Plasma method), atomic absorption analysis and an ion electrode method.

In order to examine an anti-dental caries function, an artificial oral device is used to obtain demineralized enamel which is as real as possible (see Jpn. J. Oral Biol. 20:288-291, 1984, for example). For example, this device may comprise an electrode, an enamel section attached around the electrode, and a mutans streptococci cell suspension, a culture solution, and a means for dropping a sugar solution. With this device, mutans streptococci bacteria which synthesize water-insoluble glucan are attached to the electrode surface to form an artificial plaque, thereby creating low pH. Moreover, an artificial plaque is similarly formed on the enamel piece, resulting in a significant reduction of the hardness of the enamel.

EXAMPLES

Hereinafter, the present invention will be described in detail by way of examples. These examples are not intended to limit the present invention. Materials, reagents, etc. used in the examples are commercially available unless otherwise mentioned.

Example 1

Example 1 shows a method for producing phosphorylated oligosaccharide for use in the compositions of the present invention.

First, a 1% solution of potato starch was rapidly heated to 100° C. while being dissolved in 5 ml of a solution containing 6 mM sodium chloride and 2 mM calcium chloride so as to be gelatinized. Thereafter, 35 U of α-amylase (Fukutamirase,) produced by Hankyu Bioindustry Ltd.) was allowed to act on the gelatinized mixture and held at 50° C. for 30 minutes. A small amount of the reaction solution was taken to prepare 0.2% saccharide solution. 1/10 parts of 0.01 M iodine-potassium iodide solution was added to one parts of the saccharide solution. The resulting mixture was confirmed to be negative in iodometry. Thereafter, 2 U of pullulanase (produced by Hayashibara Biochemical Lab.) and 6 U of glucoamylase (produced by Toyobo Co., Ltd.) were allowed to act on the mixture at 40° C. for 20 hours simultaneously. The reaction was terminated, followed by centrifugation. The supernatant was applied to an anion exchange resin column (Chitopearl BCW 2501; produced by Fuji Spinning Co., Ltd.) equilibrated with 20 mM acetate buffer (pH 4.5). The column was thoroughly washed with the acetate buffer to remove neutral saccharide, followed by elution with the acetate buffer containing 0.5 M sodium chloride. Each eluted fraction was condensed using an evaporator, desalted, and lyophilized, thereby obtaining phosphorylated oligosaccharide.

The thus-obtained phosphorylated oligosaccharide was applied again to the anion exchange resin column (Chitopearl BCW 2501) equilibrated with 20 mM acetate buffer (pH 4.5). The column was thoroughly washed with the acetate buffer to remove neutral saccharide. The column was subjected to elution with the acetate buffer containing 0.15 M sodium chloride and then with the acetate buffer containing 0.5 M sodium chloride. The collected fractions were desalted and lyophilized. The analysis of these fractions in accordance with the above-mentioned method for determining the structure indicated that in phosphorylated saccharides obtained from the 0.15 M sodium chloride-eluted fraction (PO-1 fraction), one phosphate group was bound to glucan having 3 to 5 glucoses with α-1,4 linkages; and in phosphorylated saccharide obtained from the 0.5 M sodium chloride-eluted fraction (PO-2 fraction), two or more phosphate groups were bound to glucan having 2 to 8 glucoses with α-1,4 linkages.

The above-described structural analysis of phosphorylated oligosaccharide was conducted as follows.

First, phosphate groups were removed from phosphorylated oligosaccharides. 100 μl of 3% phosphorylated oligosaccharide solution was mixed with 100 μl of 60 mM sodium carbonate buffer (pH 9.4) containing 10 mM magnesium chloride, 0.3 mM zinc chloride, and 0.05% sodium azide. 100 μl of 30 U/ml alkaline phosphatase (EC. 3.1.3.1; derived from *E. coli*; manufactured by SIGMA) was added to the mixture which was then allowed to react at 40° C. for 18 hours. The reaction was terminated by removing the alkaline phosphatase using an ultra filtration membrane, thereby obtaining a reaction liquid (hereinafter referred to as reaction liquid A) containing saccharides from which phosphate groups had been removed (hereinafter referred to as dephosphorylated saccharides).

To 10 μl of the resultant reaction liquid A, 5000 U/ml of β-amylase (derived from sweet potato; manufactured by SIGMA) dissolved in 10 μl of 200 mM acetate buffer (pH 4.8) was added, and the resultant mixture was held at 37° C. for 2 hours (the resultant liquid is referred to as reaction liquid B). Similarly, 300 U/ml of glycoamylase (derived from Rhizopus; manufactured by Toyobo Co., Ltd.) dissolved in 10 μl of 60 mM acetate buffer (pH 4.5) was added to 10 μl of reaction liquid A, and the resultant mixture was held at 35° C. for 18 hours (hereinafter the resultant liquid is referred to as reaction liquid C).

Reaction liquids A to C were analyzed to confirm products therein. The products of these reaction liquids were confirmed by analyzing these liquids by high-performance liquid chromatography using an anion exchange resin column, CarboPac PA-100 (φ4×250 mm, manufactured by Dionex Corp.) or thin layer chromatography using silica gel, and comparing the analyzed results with those of standard maltooligosaccharides having various degrees of polymerization. The elution of dephosphorylated saccharides using high-performance liquid chromatography was conducted by increasing the concentration of 1 M sodium acetate, using 100 mM sodium hydroxide as a basic solution. The detection of the dephosphorylated saccharides was conducted by pulsed amperometric detector (produced by Dionex Corp.). The analysis of the dephosphorylated saccharides by thin layer chromatography can be conducted by multi-developing the dephosphorylated saccharides with acetonitrile/water (80/20), spraying a solution of sulfuric acid/methanol (=1/1), and holding at 130° C. for 3 minutes.

Reaction liquid A was analyzed so that the chain length of the phosphorylated oligosaccharides was confirmed. When reaction liquid B was analyzed, only maltose, or maltose and maltotriose (and a slight amount of glucose) were detected. Therefore, the dephosphorylated saccharide was confirmed to be glucan in which glucoses are linked to each other by α-1,4 linkages. Further, when reaction liquid C was analyzed, only glucose was detected. Therefore, the dephosphorylated saccharides were confirmed to be made of α-linked glucoses.

The average chain length of saccharides (hereinafter, represented by DP, using glucose as one unit) was obtained from the saccharide content of the dephosphorylated saccharides having various degrees of polymerization. The total saccharide content of the entire phosphorylated saccharide was determined by the phenol-sulfuric acid method. The number of linked phosphate groups was determined as inorganic phosphate obtained by subjecting the dephosphorylated saccharide to wet incineration (Starch-related saccharide experimental method, Biochemistry experimental method 19, M. Nakamura et al., p. 31, 1986, JSSP Tokyo). The number of bound phosphate groups per molecule was calculated using the amount of inorganic phosphate determined after the wet incineration of the dephosphorylated saccharide and DP in accordance with the following formula:

$$\text{(The average number of bound phosphate groups per molecule)} = \frac{[\text{Inorganic phosphate quantified after wet incineration}]}{[\text{Total sugar amout in entire phosphorylated saccharides (g)}]/[\text{Average molecular weight of dephosphorylated saccharide calculated from } DP]}$$

Example 2

10 g of each of a PO-1 fraction containing phosphorylated oligosaccharides having one phosphate group per molecule and a PO-2 fraction containing phosphorylated oligosaccharides having two phosphate groups was dissolved in 100 ml of distilled water. These aqueous solutions were desalted using an electrodialyzer (Micro acilyzer) G3, AC210-400 membrane: manufactured by Asahi Kasei Co., Ltd), and were then subjected to ion exchange using strong cation exchange resin (Dowex 50w 20-50 MESH, H-Form: manufactured by Nisshin Kasei), thereby obtaining a saccharide soluton of pH 2.7. The resultant solution was neutralized with 1 N sodium hydroxide solution or calcium hydroxide solution, followed by lyophilization, thereby preparing a phosphorylated oligosaccharide sodium or calcium salt.

Phosphorylated saccharides (in the form of a sodium salt or a calcium salt) used in the following examples were phosphorylated saccharide mixture containing 80% or more of the above-described PO-1 fraction phosphorylated saccharides and the remainder of the PO-2 fraction phosphorylated saccharides.

Example 3

In Example 3, a system using bovine tooth pieces was used to clarify the effect of phosphorylated oligosaccharides on remineralization of early dental caries.

This experiment was conducted basically in accordance with Inaba. D et al., Eur. J. Sci. 105:74-80, 1997; Inaba. D et al., J. Dent. Helth. 47:67-74, 1997; and Iijima. Y et al., Caries Research. 33:206-213, 1999.

Tooth pieces used in the experiment were prepared as follows: cubic bovine tooth pieces 3 mm per side were placed so that the enamel surfaces thereof are up. The pieces were covered with composite resin except for the enamel surfaces. The enamel was treated with wet abrasive sandpaper. Demineralization was conducted as follows: the tooth pieces were immersed in 1% lactate gel (pH 5.0) containing 6% carboxymethylcellulose gel at 37° C. for 3 weeks. Remineralization was conducted as follows: the tooth pieces subjected to demineralization were immersed in 20 mM 2-[4-(2-hydroxyethyl)]-1-piperidinylethane sulfonate (HEPES) buffer (pH 7.0) containing 1.5 mM $CaCl_2$ and 0.9 mM $KH_2PO_4$ at 37° C. for one week.

The following eight test groups were prepared: (1) only demineralization (blank; "blank" in FIGS. 1 and 2); (2) only remineralization (negative control; "control" in FIGS. 1 and 2); (3) a remineralization solution+2 ppm fluorine (F) (positive control; "2 ppm F" in FIGS. 1 and 2); (4) a remineralization solution+4.0% phosphorylated oligosaccharide sodium salt ("POs Na 4%" in FIGS. 1 and 2); (5) a remineralization solution+1.0% phosphorylated oligosaccharide sodium salt ("POs Na 1%" in FIGS. 1 and 2); (6) a remineralization solution+0.2% phosphorylated oligosaccharide sodium salt ("POs Na 0.2%" in FIGS. 1 and 2); (7) a remineralization solution+0.2% phosphorylated oligosaccharide calcium salt ("POs Ca 0.2%" in FIGS. 1 and 2); and (8) a remineralization solution+0.07% phosphorylated oligosaccharide calcium salt ("POs Ca 0.07%" in FIGS. 1 and 2).

Figure 2:
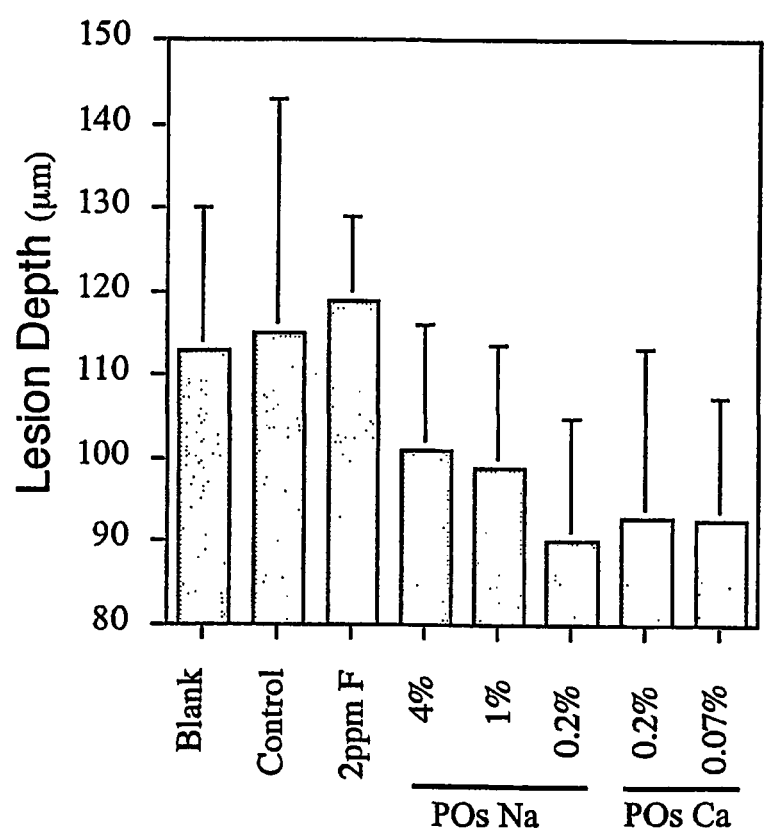
FIG. 2 is a graph showing lesion depth in a remineralization test system employing bovine teeth sections.

After each treatment, a 200 μm-thick section was prepared from each treated tooth piece, and the mineral concentration distribution thereof was analyzed from the microradiographic images (not shown). When the tooth pieces were subjected to demineralization, minerals were eluted and lost from the tooth pieces in which cavities were in turn produced (the onset of dental caries). FIG. 1 shows the graph of the mineral loss value in accordance with this mineral concentration analysis (the vertical axis indicates the mineral loss value). FIG. 2 shows the depth of demineralization (the vertical axis indicates the lesion depth (μm)). According to FIG. 1, in the case of both phosphorylated oligosaccharide sodium and phosphorylated oligosaccharide calcium, the mineral loss was minimum at the lowest concentration of the tested concentrations. This mineral loss was less than that of (2) positive control. In the case of phosphorylated oligosaccharide sodium and phosphorylated oligosaccharide calcium, low lesion depth was obtained (FIG. 2). This indicates that the cavities were filled by remineralization. Interestingly, in the case of (2) positive control with fluorine, the lesion depth was unchanged.

After each treatment, the calcium and phosphorus concentrations of the post-remineralization solution were also analyzed. The solution was centrifuged at 10,000 g for two minutes, and the supernatant was analyzed. The phosphorus concentration was determined by molybdic acid method ("Shin-ban Bunseki Kagaku Jikken [New Edition Analyical Chemistry Experiment] (1st ed.), pp. 313-314, published by Kagaku Dojin K.K."), and the calcium concentration was determined by OCPC method (manufactured by Wako Pure Chemicals: measured by a "calcium C test Wako" kit). The results are shown in Table 1.

TABLE 1

|  |  | Pi (mM) | Ca (mM) |
|---|---|---|---|
| Control |  | 0.34 | 0.68 |
| 2 ppm F |  | 0.41 | 0.73 |
| POs Na | 4% | 1.4 | 3.86 |
|  | 1% | 1.2 | 1.86 |
|  | 0.2% | 1.1 | 1.63 |
| POs Ca | 0.2% | 1.2 | 2.66 |
|  | 0.07% | 1.2 | 1.80 |

According to Table 1, it was found that by the addition of phosphorylated oligosaccharides, the concentrations of calcium and phosphorus dissolved in the solution remained high.

Therefore, this experiment suggests that by addition of phosphorylated oligosaccharides, the concentrations of calcium and phosphorus dissolved in the solution remains high, and as a result, these solubilized phosphorus and calcium may be supplied to dental caries portions and utilized for remineralization. Such a phenomenon is considered to occur in the human oral cavity.

Example 4

In Example 4, a remineralization simple test system was used to clarify an effect of phosphorylated oligosaccharides on remineralization for early dental caries.

(Procedure of Remineralization Test System)

In order to examine the remineralization phenomenon in a more simple manner, conditions under which remineralization occurs more easily were simplified. In a system including hydroxyapatite, calcium and phosphorus are supplied for crystallization and soluble calcium is reduced. In contrast, in a system including no hydroxyapatite, calcium and phosphorus are not precipitated so that the solubility thereof is held at a high level. Based on these facts, the following test system was designed.

500 μl of solution is prepared by mixing the following materials in the following order: (1) 50 μl of 200 mM HEPES buffer (pH 7.0); (2) 200 μl of deionized water or a sample; (3) 50 μl of 18 mM $KH_2PO_4$ solution; (4) 50 μl of 30 mM calcium chloride solution; and (5) hydroxyapatite suspension (5 mg/ml) or deionized water. After the addition of (3), 0.1 N potassium hydroxide solution is used to adjust the pH of the solution. The resultant solution is stirred and incubated at 37° C. for 1 to 7 days. Thereafter, the solution is centrifuged at 12,000 rpm for 3 minutes. The calcium concentration of the resultant supernatant was measured by OCPC method (as above). To this end, absorbance is measured at 570-nm using calcium C test Wako (Code; 272-21801). The percentage of soluble calcium is obtained by dividing the calcium concentration of the supernatant by the concentration of added calcium multiplied by 100. The percentage of remineralization is obtained by calculating the difference between the value obtained by the deionized water and the value obtained at the time of the addition the hydroxyapatite at (5).

(Effects of Phosphorylated Oligosaccharides Having Various Concentrations on Remineralization)

Figure 3:
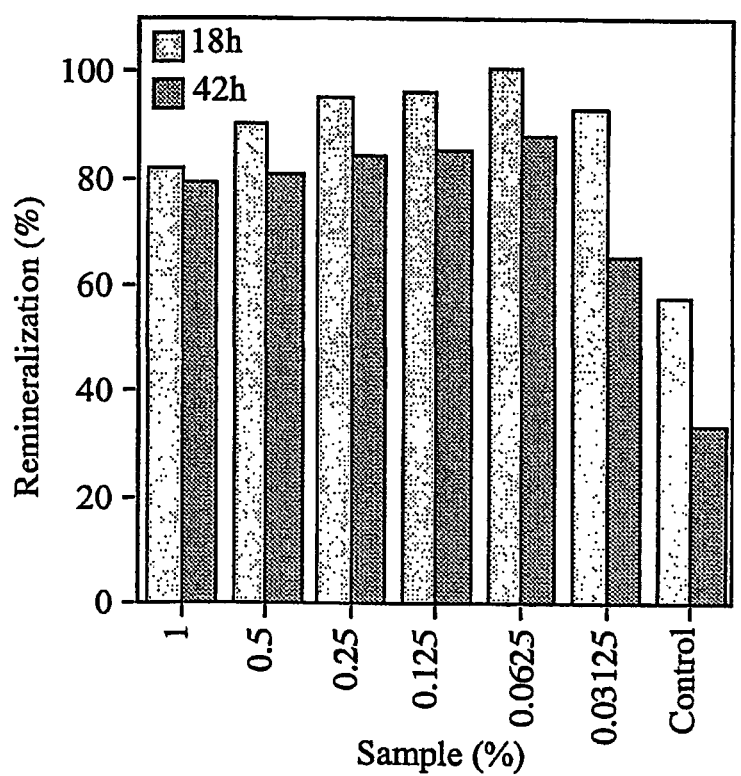
FIG. 3 is a graph showing the results of remineralization in a simple test system of Example 4 employing a phosphorylated oligosaccharide sodium salt.
Figure 4:
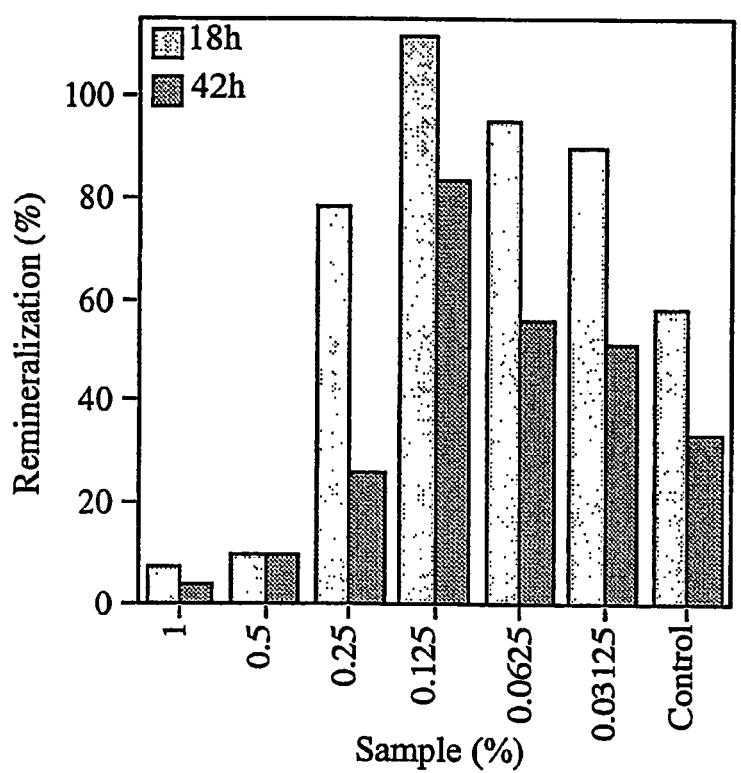
FIG. 4 is a graph showing the results of remineralization in a simple test system of Example 4 employing a phosphorylated oligosaccharide calcium salt.

The above-described simple test system was used to incubate a phosphorylated oligosaccharide sodium salt and a phosphorylated oligosaccharide calcium salt having various concentrations at 37° C. for 18 or 42 hours. The results of remineralization in the case of the phosphorylated oligosaccharide sodium salt and the phosphorylated oligosaccharide calcium salt are shown in FIGS. 3 and 4, respectively (in FIGS. 3 and 4, the vertical axis indicates the remineralization rate (%), and the horizontal axis indicates the sample (%), and control indicates no addition of the samples; for each sample concentration, a bar to the left indicates the 18 hour treatment and a bar to the right indicates the 42 hour treatment). The phosphorylated oligosaccharide sodium salt even at low concentration improved the ability to solubilize the added calcium (FIG. 3). The phosphorylated oligosaccharide calcium salt had a low ability to solubilize the exogenously added calcium salt, and rather released extra calcium to change the ratio of calcium to phosphorus in the solution so that calcium is more easily precipitated and therefore the high calcium concentration cannot be maintained (FIG. 4).

Therefore, the phosphorylated oligosaccharide sodium salt could exhibit the solubilizing action without changing the ratio of calcium to phosphorus concentrations in the system. In the case of the phosphorylated oligosaccharide calcium salt, it was considered that phosphorus (phosphate, a phosphorus compound, etc.) needs to be concurrently supplied to maintain the Ca/P ratio at 1.67 (P/Ca ratio=0.6). Alternatively, the concentration of the added phosphorylated oligosaccharide calcium salt need have little influence on the ratio.

(Effects of Phosphorylated Oligosaccharides at Ca/P Concentration Ratio=1.67 (P/Ca Concentration Ratio=0.6) on the Remineralization Effect)

The ratio of calcium to phosphorus concentrations was set to be 1.67 (P/Ca concentration ratio=0.6) when phosphorylated oligosaccharide calcium salt was used, the concentrations were set so that the calcium was derived from the phosphorylated oligosaccharides. The sodium salt was set to match the phosphorylated oligosaccharide concentration. The concentration settings are shown in Table 2 below.

TABLE 2

| Control | | |
|---|---|---|
| No. | P (mM) | Ca (mM) |
| −HAp | | |
| 1 | 0.9 | 1.5 |
| 2 | 1.8 | 3.0 |
| 3 | 2.7 | 4.5 |
| 4 | 3.6 | 6.0 |
| 5 | 4.5 | 7.5 |
| +HAp | | |
| 6 | 0.9 | 1.5 |
| 7 | 1.8 | 3.0 |
| 8 | 2.7 | 4.5 |
| 9 | 3.6 | 6.0 |
| 10 | 4.5 | 7.5 |
| POs Na | | |
| No. | P (mM) | Ca (mM) | 試料 (%) |

TABLE 2-continued

| | −HAp | | |
|---|---|---|---|
| 11 | 0.9 | 1.5 | 0.25 |
| 12 | 1.8 | 3.0 | 0.50 |
| 13 | 2.7 | 4.5 | 0.75 |
| 14 | 3.6 | 6.0 | 1.00 |
| 15 | 4.5 | 7.5 | 1.25 |
| | +HAp | | |
| 16 | 0.9 | 1.5 | 0.25 |
| 17 | 1.8 | 3.0 | 0.50 |
| 18 | 2.7 | 4.5 | 0.75 |
| 19 | 3.6 | 6.0 | 1.00 |
| 20 | 4.5 | 7.5 | 1.25 |

POs Ca

| No. | P (mM) | Ca (mM) | 試料 (%) |
|---|---|---|---|
| | −HAp | | |
| 21 | 0.9 | 1.5 | 0.25 |
| 22 | 1.8 | 3.0 | 0.50 |
| 23 | 2.7 | 4.5 | 0.75 |
| 24 | 3.6 | 6.0 | 1.00 |
| 25 | 4.5 | 7.5 | 1.25 |
| | +HAp | | |
| 26 | 0.9 | 1.5 | 0.25 |
| 27 | 1.8 | 3.0 | 0.50 |
| 28 | 2.7 | 4.5 | 0.75 |
| 29 | 3.6 | 6.0 | 1.00 |
| 30 | 4.5 | 7.5 | 1.25 |

Figure 5:
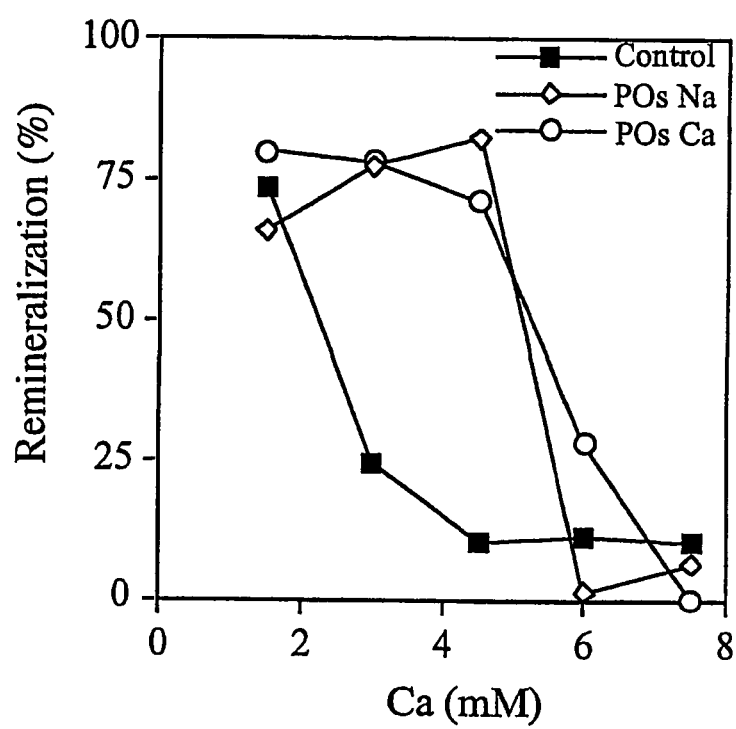
FIG. 5 is a graph showing the effect of phosphorylated oligosaccharides on remineralization where P/Ca is 0.6.

Incubation at 37° C. for 15 hours was conducted in the above-described simple test system. The results are shown in FIG. 5 (the vertical axis indicates the remineralization rate (%), the horizontal axis indicates the Ca concentration (mM), filled squares represent a control without a phosphorylated oligosaccharide salt, diamonds represent a phosphorylated oligosaccharide sodium salt (POsNa), circles represent a phosphorylated oligosaccharide calcium salt (POs Ca)). As shown in FIG. 5, when the Ca/P concentration ratio=1.67 (P/Ca concentration ratio=0.6) was constant and the concentration of added calcium was increased, similar results were obtained between the phosphorylated oligosaccharide sodium salt and the phosphorylated oligosaccharide calcium salt. When the added calcium salt was 6 mM or more, the effect of the addition of phosphorylated oligosaccharides was reduced.

(Effects of Phosphorylated Oligosaccharides at Various Ca/P on the Remineralization Effect)

The above-described simple test system was incubated at 37° C. for 17.5 hours or 1 week while The ratio of calcium to phosphorus concentrations was changed as shown in Table 3 (Table 3 uses P/Ca).

TABLE 3

| No. | X (P) | Y (Ca) | *1 | *2 |
|---|---|---|---|---|
| 1 | 9 | 15 | CaCl$^2$ | D.W. |
| 2 | 18 | 15 | CaCl$^2$ | D.W. |
| 3 | 27 | 15 | CaCl$^2$ | D.W. |
| 4 | 36 | 15 | CaCl$^2$ | D.W. |
| 5 | 45 | 15 | CaCl$^2$ | D.W. |
| 6 | 9 | 15 | CaCl$^2$ | 2.4% POs-Na |
| 7 | 18 | 15 | CaCl$^2$ | 2.4% POs-Na |
| 8 | 27 | 15 | CaCl$^2$ | 2.4% POs-Na |
| 9 | 36 | 15 | CaCl$^2$ | 2.4% POs-Na |
| 10 | 45 | 15 | CaCl$^2$ | 2.4% POs-Na |
| 11 | 9 | 15 | 2.4% POs-Ca | D.W. |
| 12 | 18 | 15 | 2.4% POs-Ca | D.W. |
| 13 | 27 | 15 | 2.4% POs-Ca | D.W. |
| 14 | 36 | 15 | 2.4% POs-Ca | D.W. |
| 15 | 45 | 15 | 2.4% POs-Ca | D.W. |

Figure 6A:
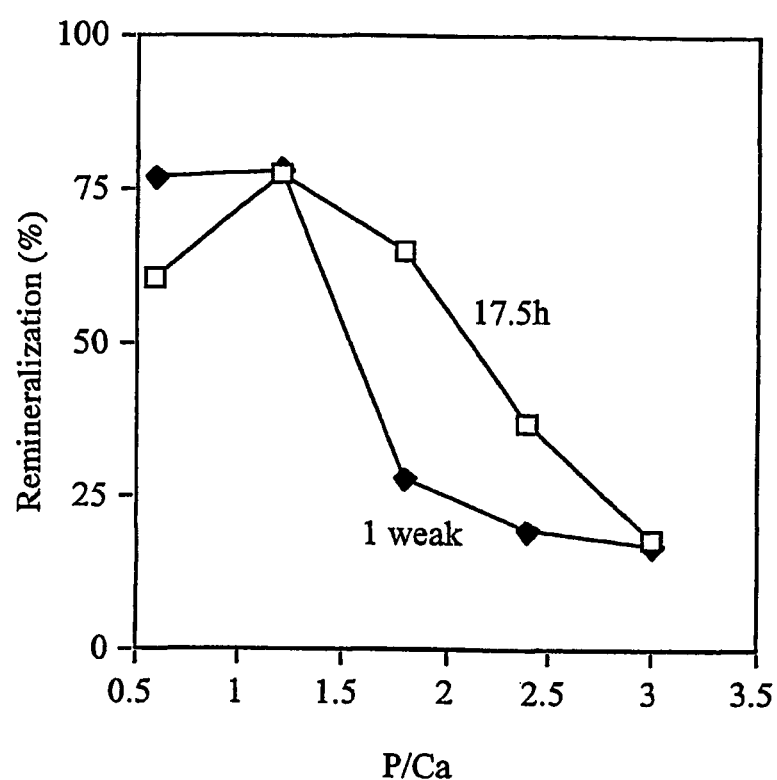
FIG. 6A is a graph showing the effect of changes in P/Ca concentration ratio on remineralization in the absence of phosphorylated oligosaccharides.
Figure 6B:
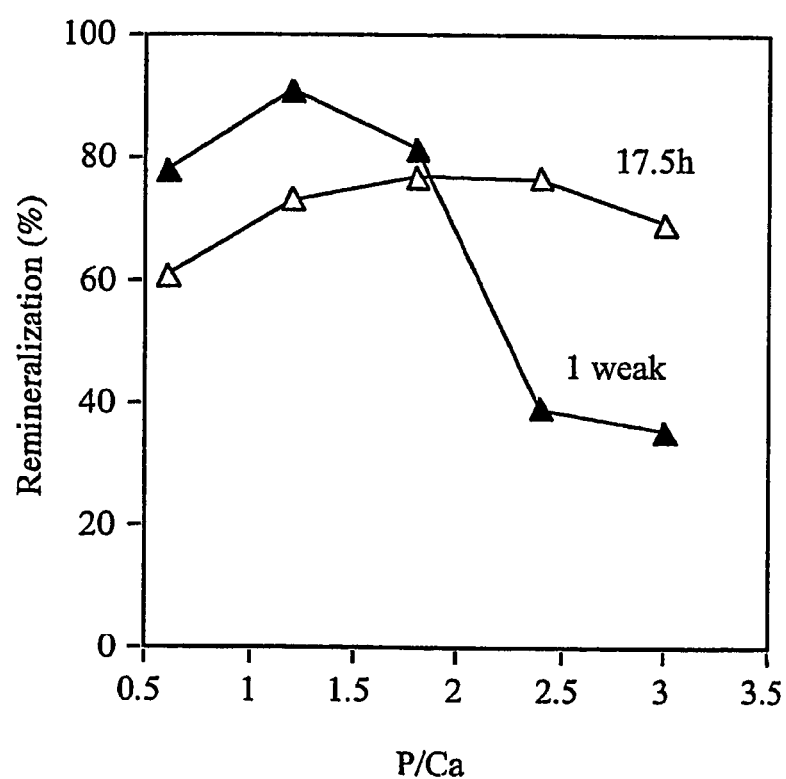
FIG. 6B is a graph showing the influence of changes in P/Ca concentration ratio on remineralization in the presence of a phosphorylated oligosaccharide sodium salt.
Figure 6C:
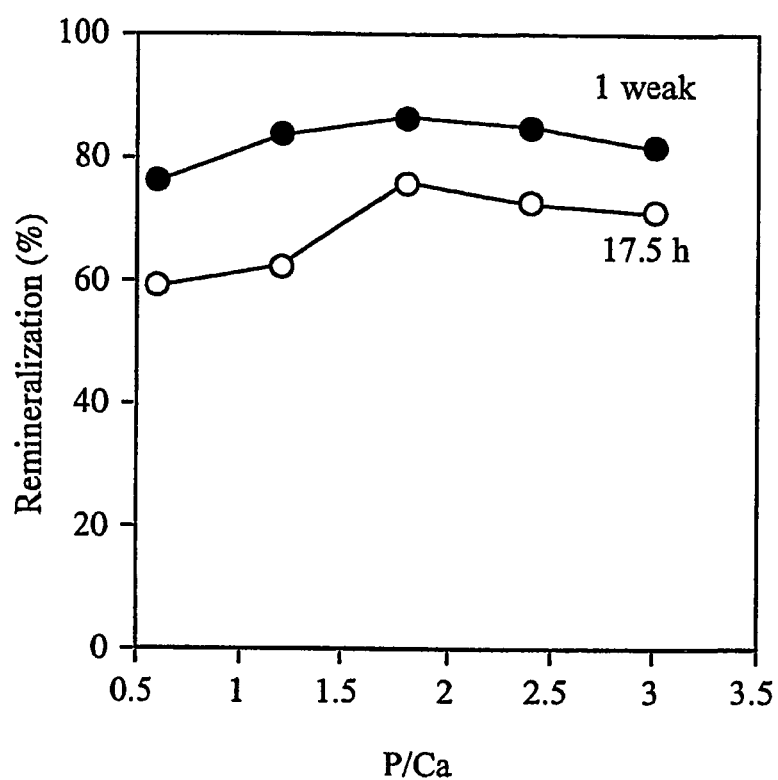
FIG. 6C is a graph showing the influence of changes in P/Ca concentration ratio on remineralization in the presence of a phosphorylated oligosaccharide calcium salt.

The results are shown in FIGS. 6A to 6C (the vertical axis indicates the remineralization rate (%) and the horizontal axis indicates P/Ca). FIG. 6A indicates the results of a control without phosphorylated oligosaccharides. Squares represent 17.5 hour treatment and filled diamonds represent one week treatment. FIG. 6B shows the results of a phosphorylated oligosaccharide sodium salt. Triangles represent 17.5 hour treatment and filled triangles represent one week treatment. FIG. 6C shows the results of a phosphorylated oligosaccharide calcium salt. Circles represent 17.5 hour treatment and filled circles represent one week treatment. As shown in FIGS. 6A to 6C, when Ca was fixed to 1.5 mM and the phosphorus concentration was varied to change the P/Ca ratio, both the phosphorylated oligosaccharide sodium salt and the phosphorylated oligosaccharide calcium salt were considered to cause relatively effectively remineralization. According to the results, the calcium salt was considered to be more stable even at a high concentration of phosphorus.

Example 5

Figure 7A:
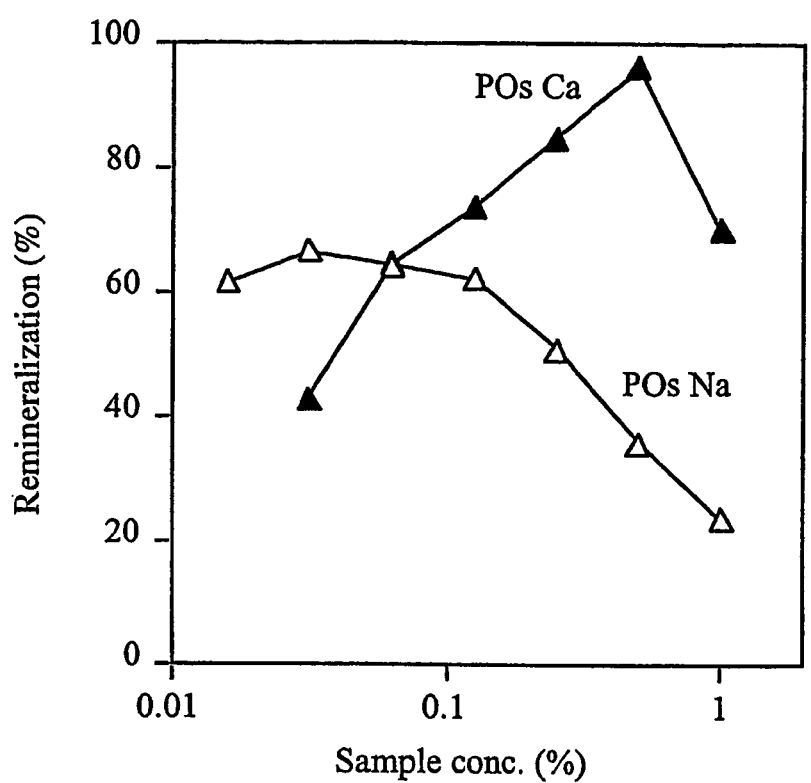
FIG. 7A is a graph showing the remineralization effects of a phosphorylated oligosaccharide calcium salt and a phosphorylated oligosaccharide sodium salt in Example 5.
Figure 7B:
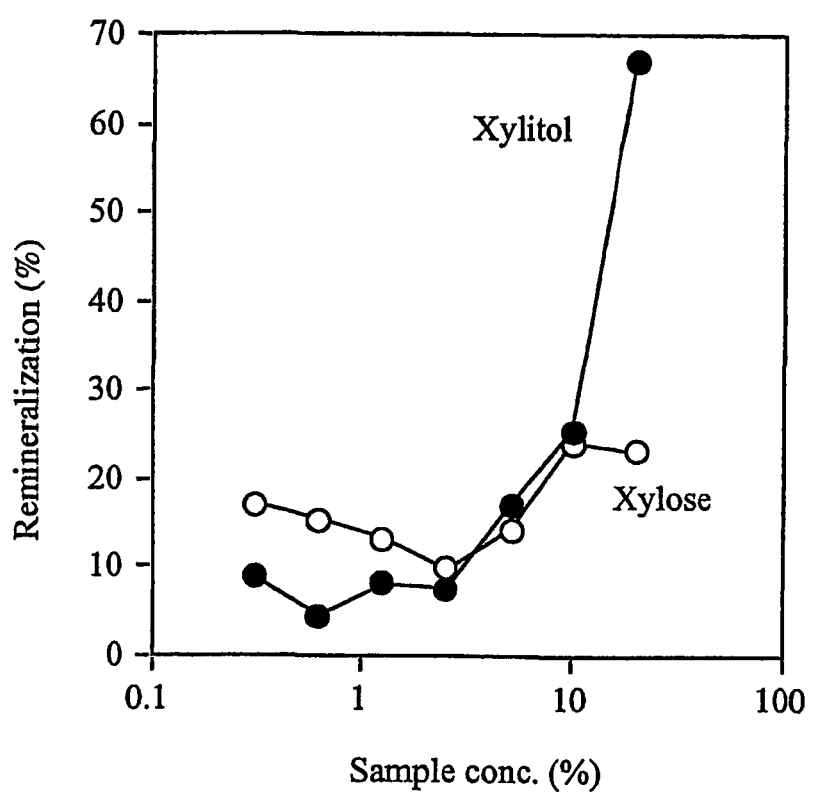
FIG. 7B is a graph showing the remineralization effects of xylitol and xylose.
Figure 7C:
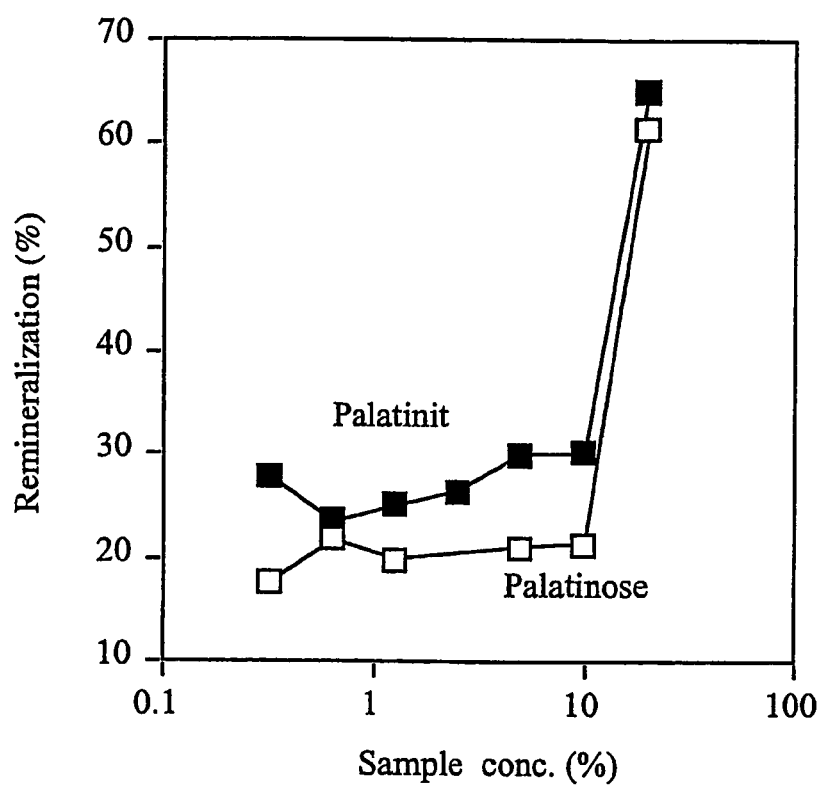
FIG. 7C is a graph showing the remineralization effects of palatinit and palatinose.

Example 5 shows comparison of phosphorylated oligosaccharides with other anti-dental caries agents in the remineralization effect. As anti-dental caries agents, xylose, xylitol, palatinose, and palatinit were used. The simple system of Example 3 was used to examine the remineralization effect. Incubatoin at 37° C. for 8 days was conducted in the simple system. The results are shown in FIGS. 7A to 7C (the vertical axis indicates the remineralization rate (%) and the horizontal axis indicate the sample concentration (%)). FIG. 7A shows the results of a phosphorylated oligosaccharide salt where filled triangles represent a calcium salt and open triangles represent a sodium salt. FIG. 7B shows the results of xylitol where filled circles represent xylitol and open circles represent xylose. FIG. 7C shows the results of palatinit where filled squares represent palatinit and open squares represent palatinose. According to FIGS. 7A to 7C, the phosphorylated oligosaccharides of a concentration of as low as about 0.1% exhibited a high remineralization effect, while the other anti-dental caries agents (xylitol, palatinose, and palatinit) exhibited a remineralization effect at a concentration of 20% as previously reported (Japanese Laid-Open Publication No. 2000-128752, Japanese Laid-Open Publication No. 2000-247852, etc.). In the case of xylose, the remineralization percentage was low at any concentration.

Example 6

In Example 6, the effect of phosphorylated oligosaccharides to inhibit demineralization was examined.

A demineralization solution having the following composition was prepared: 6.0 mM calcium chloride solution; 3.6 mM potassium dihydrogenphosphate; 2% lactate solution; and 5 mg/ml hydroxyapatite solution, pH 5.0. 125 µl of the demineralization solution and 125 µl of phosphorylated oligosaccharide sodium salt solutions having final concentrations of 0.2% and 2% were mixed and stirred, followed by incubation at 37° C. for 2 days. Thereafter, the mixtures were centrifuged at 12,000 rpm for 3 minutes. The calcium concentration of the resultant supernatant was measured by OCPC method. The added calcium concentration and the calcium concentration after the treatment were compared with each other. If the difference between the added calcium concentration and the calcium concentration after the treatment in the presence of the test sample was small as compared to a control (without a test sample), the test sample was recognized to have the effect of inhibiting demineralization. Comparing a control (5 mM) without phosphorylated oligosaccharides, both the 0.2% and 2% phosphorylated oligosaccharide sodium salt solutions had a small difference (3 mM and 2 mM). Therefore, the phosphorylated oligosaccharide sodium salt was considered to have the effect of inhibiting demineralization.

Example 7

Example 7 shows a synergistic effect of phosphorylated oligosaccharides with fluorine with respect to the remineralization effect.

Compositions described in Table 4 below were used to examine the remineralization effect in the presence or absence of phosphorylated oligosaccharides.

TABLE 4

| No. | POs Na | Ca (mM) | P (mM) | F (ppm) |
|---|---|---|---|---|
| 1 | 0.20% | 3.0 | 1.8 | 0 |
| 2 | 0.20% | 3.0 | 1.8 | 3.91 |
| 3 | 0.20% | 3.0 | 1.8 | 7.81 |
| 4 | 0.20% | 3.0 | 1.8 | 15.63 |
| 5 | 0.20% | 3.0 | 1.8 | 31.25 |
| 6 | 0.20% | 3.0 | 1.8 | 62.50 |
| 7 | 0.20% | 3.0 | 1.8 | 125.00 |
| 8 | 0.20% | 3.0 | 1.8 | 250.00 |
| 9 | 0.20% | 3.0 | 1.8 | 500.00 |
| 10 | 0.20% | 3.0 | 1.8 | 1000.00 |

The simple system of Example 4 was used to examine the remineralization effect. Incubation at 37° C. for 5 days was conducted in the simple system. Thereafter, the amount of soluble calcium was measured by OCPC method. By thin layer chromatography (TLC), phosphorylated oligosaccharides were qualitatively confirmed. Conditions for TLC analysis are the following: silica gel plate (manufactured by Merck); ethanol/deionized water/acetic acid (=70/30/2); development one time at room temperature; 5 µl of a sample added; 1 µl of 1% phosphorylated oligosaccharides and 1 µl of 1% maltotriose as markers.

Figure 8:
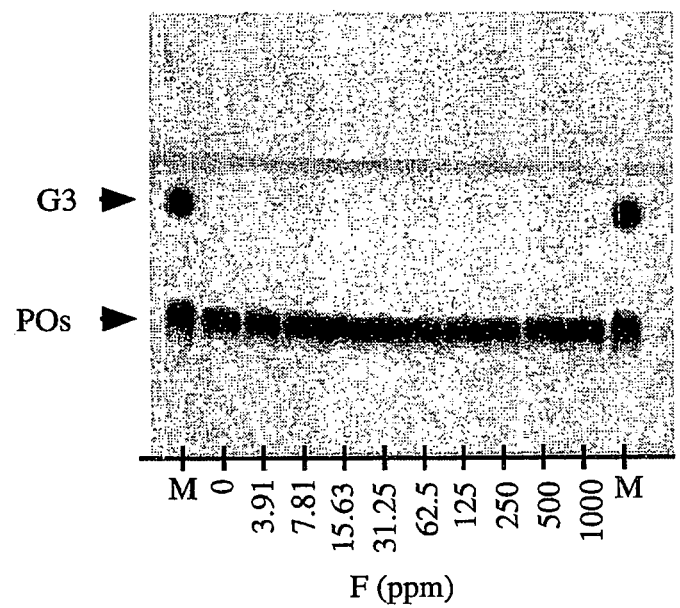
FIG. 8 is a photograph showing the results of TLC analysis in Example 7.
Figure 9:
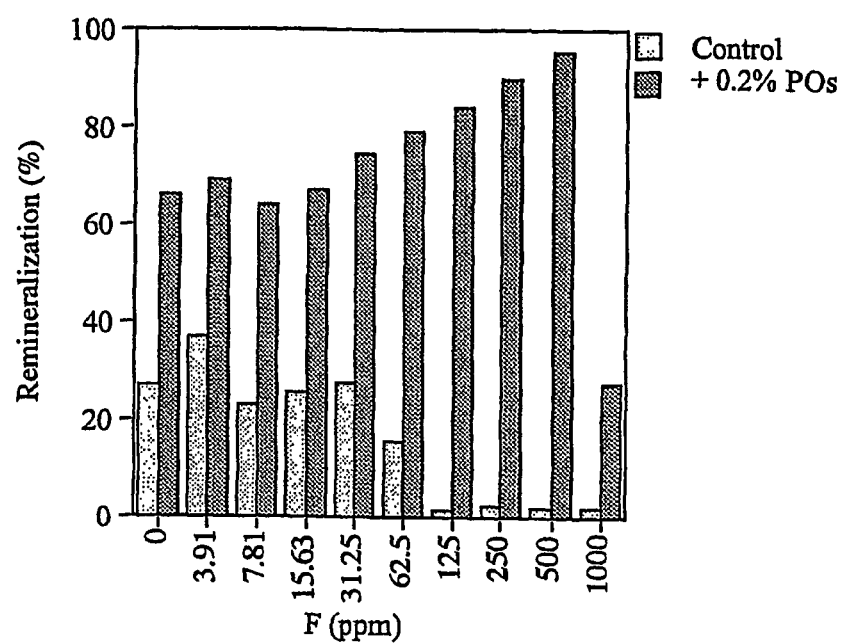
FIG. 9 is a graph showing the synergistic action of phosphorylated oligosaccharides and fluorine on remineralization in Example 7.

The results of the TLC analysis are shown in Table 8. In FIG. 8, each lane indicates fluorine having various concentrations (ppm), upper spots represent maltotriose, and lower spots represent phosphorylated oligosaccharides. FIG. 9 shows a synergistic action of phosphorylated oligosaccharides with fluorine with respect to remineralization (the vertical axis indicates the remineralization rate (%) and the horizontal axis indicates the fluorine concentration (ppm); in each value, a bar to the left indicates a control without phosphorylated oligosaccharides and a bar to the right belongs to a group of 0.2% phosphorylated oligosaccharides). Fluorine is halogen elements which are highly reactive. The effect of fluorine on phosphorylated oligosaccharides and the quantification of calcium was examined. Under the conditions of the experiment, it seemed that the influence of the addition of fluorine was trivial (FIG. 8). The addition of fluorine alters the balance of the concentration ratio of Ca to P so that the insolubility is reduced. Therefore, the remineralization rate was reduced due to an increase in the fluorine concentration. However, when 0.2% phosphorylated oligosaccharide sodium salt was added, the remineralization effect tended to be increased, so that a significant synergistic effect could be confirmed (FIG. 9).

Example 8

Example 8 shows the mixture phosphorylated oligosaccharides with a chewing gum and the elution of the phosphorylated oligosaccharides to the human oral cavity.

Sheet gums (plate-like gums) containing phosphorylated oligosaccharide calcium salts shown in Table 5 (the calcium content was 3.2%) were prepared (a sheet gum had a weight of about 3.2 g).

TABLE 5

| | addition (%) |
|---|---|
| Gum Base | 25.2 |
| POs Ca | 22.7 |
| Xylitol | 50.4 |
| Glycerol | 0.7 |
| Mint Oil | 1.0 |
| Total | 100.0 |

3.2 g/slab gum

The amount of the calcium salt eluted into the oral cavity over time when the gum was chewed, was analyzed by thin layer chromatography (TLC). Conditions for TLC were the following: the development plate was a silica gel plate; the development eluent was ethanol/deionized water/acetic acid=70/30/2; the development temperature was room temperature, and development was done one time; the amount of a spot sample was 3 µl; detection was conducted by spraying a detection solution (sulfate/ethanol=1:1) to the plate, followed by processing at 130° C. for 3 minutes, whereby spots developed color.

Figure 10:
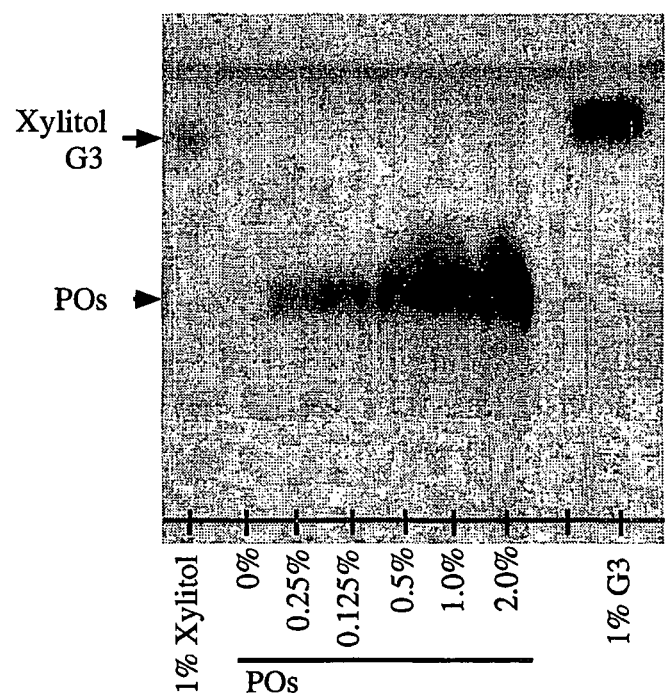
FIG. 10 is a photograph showing the results of TLC analysis of phosphorylated oligosaccharides having a standard solution concentration in Example 8.
Figure 11:
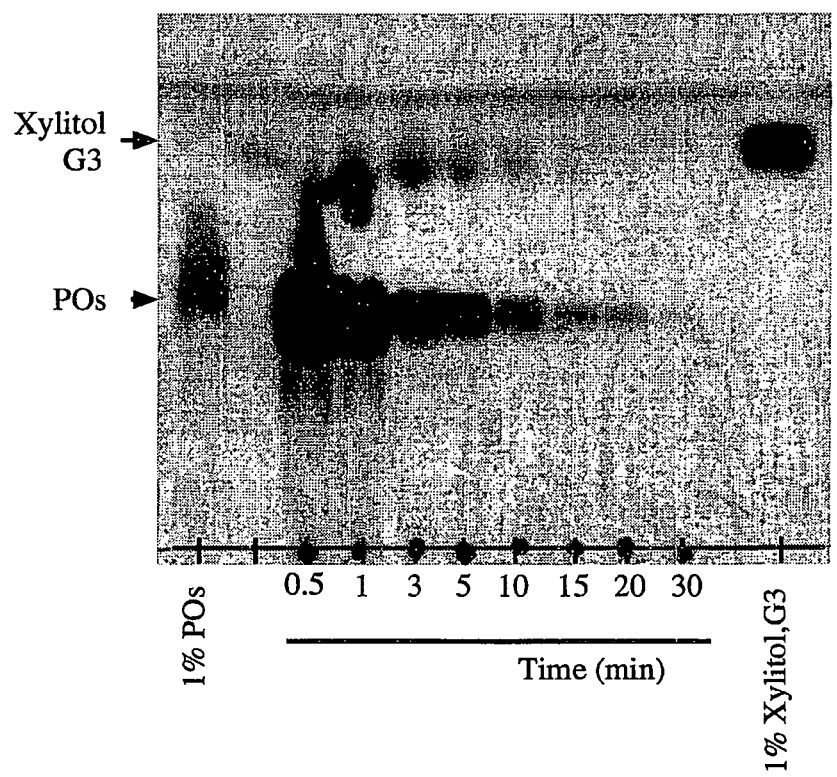
FIG. 11 is a photograph showing the results of TLC analysis indicating the amount of elution over time when eating a phosphorylated oligosaccharide containing gum in Example 8.

FIG. 10 shows the results of the TLC analysis of phosphorylated oligosaccharides having a standard solution concentration. Each lane shows elution of phosphorylated oligosaccharides having various concentrations (indicating 1% xylitol as a control to the left and 1% maltotriose (G3) to the right). Lower spots represent phosphorylated oligosaccharides, while upper spots represent xylitol and maltotriose. FIG. 11 shows the elution amount over time when a gum containing phosphorylated oligosaccharides was chewed. Each lane indicates the elution over a mastication time (indicating 1% phosphorylated oligosaccharides as a control to the left and 1% xylitol and maltotriose (G3) to the right). Lower spots represent phosphorylated oligosaccharides and upper spots represent xylitol and maltotriose. The phosphorylated oligosaccharides are not hydrolysed with saliva amylase. According to these figures, it will be understood that about 10 minutes after the beginning of mastication, a relatively high concentration of phosphorylated oligosaccharides were present in the oral cavity, and 20 minutes after, the phosphorylated oligosaccharides remained at an about 0.25% concentration.

Example 9

Example 9 shows the effect of phosphorylated oligosaccharides on fermentation of sucrose.

S. mutans strain 8148 was incubated in 1,000 ml of brain heart infusion medium (manufactured by DIFCO Corporation) at 37° C. for 14 hours. Thereafter, the bacteria were collected by centrifugation at 6,000 rpm for 20 minutes. The bacteria was washed with phosphate buffered saline (PBS, pH 7.2), and suspended in the same PBS to 40% (v/v). To measure the pH, a reaction mixture (250 µl) was made of 125 µl of 40% bacterial cell suspension, 62.5 µl of 80 mM sucrose, and 62.5 µl of an aqueous solution containing various oligosaccharides (5% phosphorylated oligosaccharide sodium salt and phosphorylated oligosaccharide calcium salt). The pH of the reaction mixture was continuously measured with a pH meter (manufactured by Toa Denpa) while being incubated at 37° C.

When 0.684% sucrose or 0.684% glucose was added to the 20% bacterial cell suspension containing S. mutans 8158 strain, the pH of the reaction liquid was below 5.0 within 5 minutes, and was reduced to 4.0 after 10 minutes. When 5% phosphorylated oligosaccharides (PO-1 and PO-2) were concurrently present, the pH reduction was clearly suppressed in either case (data not shown). When 5% phosphorylated oligosaccharide sodium salt or phosphorylated oligosaccharide calcium salt was added, the pH reduction due to fermentation of 0.684% sucrose was efficiently suppressed (data not shown).

Example 10

In Example 10, the sugar alcohol of phosphorylated oligosaccharides was prepared.

10 g of each of a PO-1 fraction containing phosphorylated oligosaccharides having one phosphate group per molecule and a PO-2 fraction containing phosphorylated oligosaccharides having two phosphate groups was dissolved in 100 ml of distilled water. The solution was adjusted to weak alkaline solution (about pH 8) with 1 N sodium hydroxide solution. To 100 ml of the resultant solution, 30 ml of 3% sodium boron hydroxide solution was added. The mixture was allowed to stand at 40° C. for one hour so that phosphorylated oligosaccharides were reduced. Thus, hydrogen was added to the reducing terminals of phosphorylated oligosaccharides. The hydrogen-added solution was adjusted to pH 7.5 with 1 N hydrochloric acid solution. After the reaction was terminated, the solution was subjected to dialysis using a 0.22 µm membrane. The resultant solution was desalted using an electrodialyzer (Micro acilyser) G3, AC210-400 membrane: manufactured by Asahi Kasei Corporation), and was then subjected to ion exchange using strong cation exchange resin (Dowex 50 w 20-50 MESH, H-Form: manufactured by Nisshin Kasei), thereby obtaining a saccharide solution of pH 2.7. The resultant solution was neutralized with 1 N sodium hydroxide solution or calcium hydroxide solution, followed by lyophilization, thereby preparing a phosphorylated oligosaccharide sodium or calcium salt.

Example 11

In Example 11, chondroitin sulfate oligosaccharides (unsaturated disaccharide (dimer)) were prepared.

4.8 g of sodium chondroitin sulfate (C type; manufactured by Katayama Kagaku) was dissolved in 500 ml of distilled water (pH 6.0). 15 U chondroitinase ACII (derived from Arthrobacter aurescens, manufactured by Seikagaku Kogyo) was added to the resultant solution and allowed to react at 37° C. for 23 hours. The reaction was terminated in a boiling bath, followed by desalting as described in Example 10. Thus, a chondroitin sulfate oligosaccharide sodium or calcium salt was prepared.

Example 12

In Example 12, the remineralization effect of various substances were examined.

The simple remineralization test system of Example 4 was used. As samples, substances shown in Table 6 below were used. All of the substances were prepared to a final concentration of 0.1%.

TABLE 6

| No. | Sample |
|---|---|
| 1 | POs Na |
| 2 | PO-2 Na |
| 3 | POsH Na |
| 4 | G3 |
| 5 | PO-2H Na |
| 6 | Glc-6-P |
| 7 | Ser-P |
| 8 | Chondroitin Sulfate C |
| 9 | Oligogalacturonic acid |
| 10 | Dimer Na |
| 11 | D.W. |

In the above-described Table 6, No. 1 POs Na indicates a phosphorylated oligosaccharide (PO-1 fraction) sodium salt, No. 2 PO-2 Na indicates a phosphorylated oligosaccharide (PO-2 fraction) sodium salt, No. 3 POsH Na indicates a phosphorylated oligosaccharide (PO-1 fraction) sugar alcohol sodium salt, No. 4 PO-2H Na indicates a phosphorylated oligosaccharide (PO-2 fraction) sugar alcohol sodium salt, No. 5 G3 indicates maltotriose (glucose tertiary saccharide), No. 6 Glc-6-P indicates glucose-6-phosphate, No. 7 Ser-P indicates phosphoserine, No. 8 indicates chondroitin sulfate C, No. 9 indicates oligogalacturonic acid, No. 10 indicates an unsaturated disaccharide of chondroitin sulfate (in Table 6 and FIG. 12, Dimer Na), and No. 11 D. W. indicates deionized water.

Figure 12:
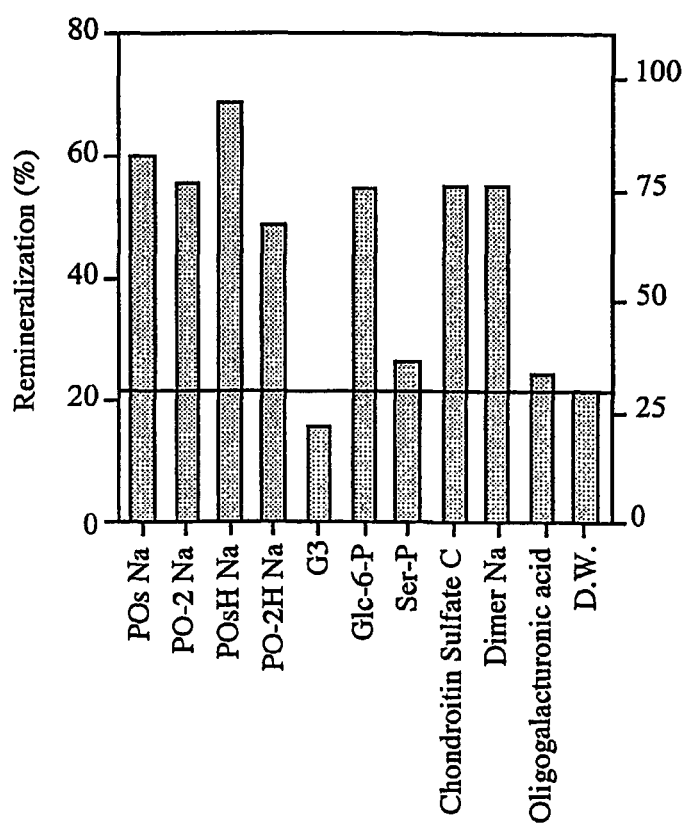
FIG. 12 is a graph showing the remineralization effect of various substances in Example 12.

The results are shown in FIG. 12 (the vertical axis indicates the remineralization rate (%) and the horizontal axis indicates the sample substances). In the figure, the substances which had a remineralization proportion higher than that of the deionized water were judged to have the remineralization effect. The phosphorylated oligosaccharide alcohol sodium salt, the glucose-6-phosphate, the chondroitin sulfate C sodium salt, and the chondroitin sulfate unsaturated disaccharide sodium salt exhibited the remineralization effect which is as good as or better than that of the phosphorylated oligosaccharide sodium salt.

Example 13

In Example 13, the remineralization effect of various substances was examined.

The simple remineralization test system of Example 4 was used. As samples, substances shown in Table 7 were used.

TABLE 7

| No. | Sample | Final (%) |
|---|---|---|
| 1 | POs Na | 0.2 |
| 2 |  | 2.0 |

TABLE 7-continued

| No. | Sample | Final (%) |
|---|---|---|
| 3 | Palatinose | 2.0 |
| 4 | | 20 |
| 5 | Xylitol | 2.0 |
| 6 | | 20 |
| 7 | Treharose | 2.0 |
| 8 | | 20 |
| 9 | Sorbitol | 2.0 |
| 10 | | 20 |
| 11 | G3 | 2.0 |
| 12 | D.W. | |
| 13 | Oganic acid | 0.2 |
| 14 | | 1.4 |
| 15 | Dextran sulfate | 0.2 |

In Table 7, No. 1 POs Na indicates a phosphorylated oligosaccharide (PO-1 fraction) sodium salt (final concentration of 0.2%), No. 2 POs Na indicates a phosphorylated oligosaccharide (PO-1 fraction) sodium salt (final concentration of 2.0%), No. 3 Indicates palatinose (final concentration of 2.0%), No. 4 indicates palatinose (final concentration of 20%), No. 5 indicates xylitol (Wako 244-0052) (final concentration of 2.0%), No. 6 indicates xylitol (Wako 244-0052) (final concentration of 20%), No. 7 indicates trehalose (Wako 02252) (final concentration of 2%), No. 8 indicates trehalose (Wako 02252) (final concentration of 20%), No. 9 indicates sorbitol (Katayama 28-4770)(final concentration of 2%), No. 10 indicates sorbitol (Katayama 28-4770) (final concentration of 20%), No. 11 G3 indicates maltotriose (final concentration of 2%), No. 12 D.W. indicates deionized water (control), No. 13 indicates organic acid (tartaric acid) (final concentration of 0.2%), No. 14 indicates organic acid (tartaric acid) (final concentration of 1.4%), and No. 15 indicates dextran sulfate (final concentration of 0.2%).

Figure 13:
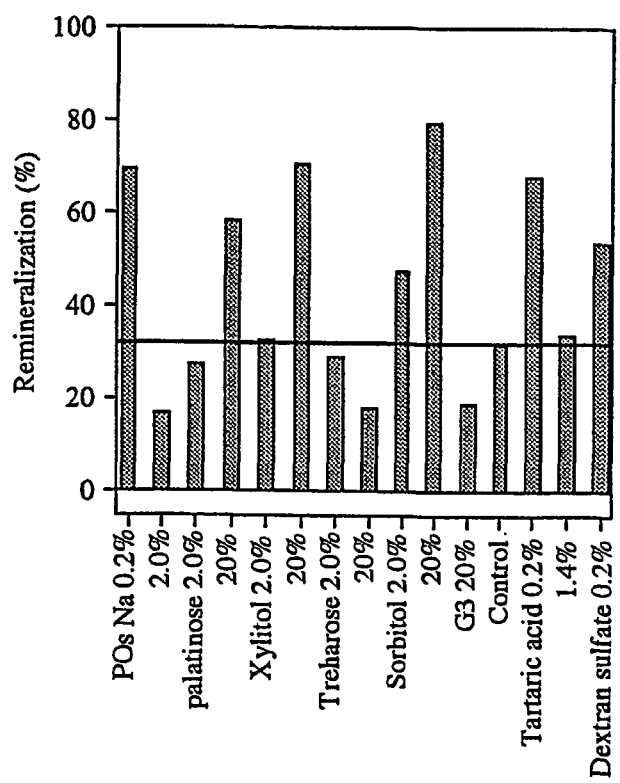
FIG. 13 is a graph showing the remineralization effect of various substances in Example 13.

The results are shown in FIG. 13 (the vertical axis indicates the remineralization rate (%) and the horizontal axis indicates sample substances). In the 20% addition group including xylitol, palatinose, and sorbitol, the remineralization effect as previously reported (as above) was confirmed. Further, similar to chondroitin sulfate, dermatan sulfate was confirmed to have the remineralization effect. The organic acid was also effective similar to phosphorylated oligosaccharides.

Example 14

In Example 14, the effect of preventing dental caries was examined in an artificial oral device.

Figure 14:
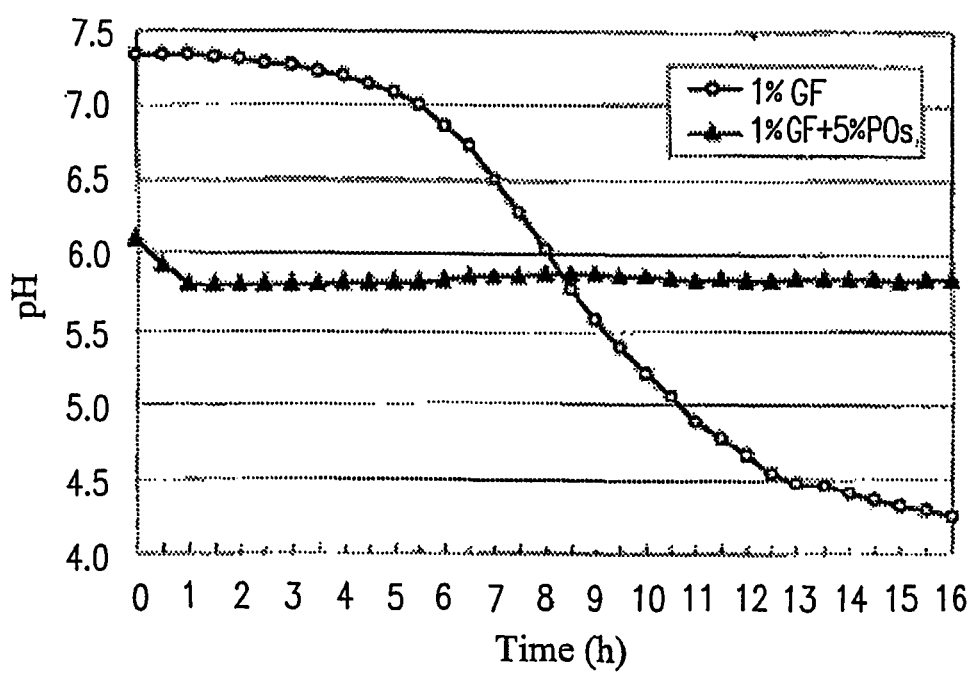
FIG. 14 is a graph showing pH changes in an artificial oral device in Example 14.

*S. sobrinus* strain 6715 culture (preincubated in brain heart infusion medium (manufactured by DIFCO Corporation)), heart infusion liquid medium (manufactured by DIFCO Corporation), and a sample solution (each solution was cooled during the testing), are each supplied to a bovine tooth (about 5×5 mm) held in constant temperature bath (37° C.) at a rate of 6 ml/hour/tube. The pH of the tooth surface was measured over time. The results are shown in FIG. 14 (the vertical axis indicates a change in pH and the horizontal axis indicates the time lapse; circles represent addition of only 1% sugar (GF) and filled triangles represent addition of 1% GF+5% phosphorylated oligosaccharides calcium salt(POs Ca)). After 16 hours, dental plaque was scraped off the tooth, and the turbidity was measured at 500 nm. Further, the amount of water insoluble glucan (WIG) formed was measured by a phenol-sulfuric acid method. The hardness of the tooth was measured by a hardness meter. The difference between this hardness and the hardness of an untreated tooth was obtained (ΔH). The results are shown in Table 8.

TABLE 8

| | | WIG (µg/mm$^2$) | Turbidity (OD$_{500}$/mm$^2$) | ΔH |
|---|---|---|---|---|
| 1% GF | Electrode | 7.2 | 0.057 | — |
| | Enamel | 10.8 ± 2.0 | 0.070 ± 0.012 | 240 ± 16.4 |
| 1% GF + 5% POsCa | Electrode | 0.3 | 0.004 | — |
| | Enamel | 0.4 ± 0.3 | 0.016 ± 0.007 | 19 ± 10.4 |

It was clear that in the case of 1% GF (sugar), organic acid was generated, and after about 10 hours, pH was 5.6 or less, and the organic acid was held within plaque. Plaque was sufficiently formed, and the tooth suffered from demineralization and became brittle. In contrast, in the case of the solution containing 1% GF and 5% phosphorylated oligosaccharides, no plaque was formed and the pH was not reduced. That is, dental caries bacteria were prevented from colonizing the tooth, so that plaque formation was blocked and demineralization of the tooth was suppressed. Therefore, the hardness of the tooth was not changed. According to this result, it was clearly found that phosphorylated oligosaccharides have the effect of preventing dental caries. This phenomenon is considered to similarly occur in the human oral cavity.

Example 15

In Example 15, phosphorylated oligosaccharides were prepared from various starches.

Starches used in this example were from rice, starch (brand name Better Friend™: manufactured by Shimada Kagaku) and tapioca starch (Sanwa Cornstarch Co., Ltd.).

100 g of starch powder was added into 800 to 1000 ml of water. To the resultant solution, 50 µl of 5000 U/ml starch liquefying α-amylase (BLA) derived from a bacterium, *B. lichenformis* (available from Fukutamirase, from Hankyu Industries, 1%) was added. The solution was gelatinized at 50° C. for 48 hours in water bath. Further, 50 µl of 5000 U/ml BLA (Fukutamirase, from Hankyu Industries, 1%), 50 µl of 200 U/ml pullulanase (Promozyme: manufactured Novo Nordisk), and 50 µl of glucoamylase (416 U/ml) (available from Toyobo) were added to the gelatinized starch, followed by incubation at 50° C. for 48 hours. The resultant mixture was centrifuged at 8,000 rpm for 20 minutes. The supernatant was applied to an anion exchange resin (Chitopearl BCW 2501; produced by Fuji Spinning Co., Ltd.) equilibrated with 10 mM acetate buffer (pH 4.5). The column was thoroughly washed with the same buffer to remove neutral saccharides, followed by elution with the same buffer containing 0.5 M sodium chloride. Each eluted fraction was condensed using an evaporator, followed by desalting and lyophilization. Thus, phosphorylated oligosaccharides were obtained.

The thus-obtained phosphorylated oligosaccharides were applied again to an anion exchange resin column (Chitopearl BCW2501) equilibrated with 20 mM acetate buffer (pH 4.5). The column was thoroughly washed with the same buffer to remove neutral saccharides. The column was subjected to elution first with the same buffer containing 0.15 M sodium chloride and next with the same buffer containing 0.5 M sodium chloride, thereby collecting fractions. The collected fractions were desalted and lyophilized. The analysis of these fractions in accordance with the above-mentioned method for determining the structure indicated that in phosphorylated saccharides obtained from the 0.15 M sodium chloride-eluted fraction (PO-1 fraction), one phosphate group was linked to glucan having 3 to 5 glucoses with α-1,4 linkages; and in phosphorylated saccharide obtained from the 0.5 M sodium chloride-eluted fraction (PO-2 fraction), two or more phosphate groups were bound to glucan having 2 to 8 glucoses with α-1,4 linkages. The structural analysis of phosphorylated oligosaccharides was conducted as described in Example 1.

Example 16

Example 16 shows that a chewing gum containing phosphorylated oligosaccharides had the effect of promoting enamel remineralization in early dental caries.

Two tablet gums (about 1.5 g/tablet): sugarless gums containing 2.5% (mean content) of POs Ca derived potato starch (containing 45% of xylitol) and sugarless gums containing no POs Ca (containing 47.5% of xylitol), were produced by a commonly used method. All experimental reagents were guaranteed reagents. The content of each substance is a proportion with respect to the total weight of a gum.

As a tooth material, the crown enamel of a bovine tooth was used. A diamond saw (manufactured by LUXO) was used to cut the enamel into blocks (7×7×3 mm) having a standardized-size side. These enamel blocks (6 samples) were embedded in an autopolymer resin (UNIFAST Trad, manufactured by GC), which were shaped into plates having a size of 15×50 mm and a thickness of 7 mm. Thereafter, the surface of the plates were abraded with wet abrasive sandpaper (grit 800) to expose flat and fresh enamel. On the other hand, the dentin side of the tooth was previously embedded in an impression compound (manufactured by GC). Each of the thus-prepared enamel block embedded plates was immersed in 100 ml of 0.1 M lactic acid gel (6 wt % carboxymethylcellulose, pH 5.0) at 37° C. for 4 weeks, whereby dental caries artificially occurred.

17 healthy subjects participated in a test in which the subjects masticate two grains of POs Ca containing gum or POs Ca-free gum (3.0 g) for 20 minutes. In the test, the subjects were not informed of the type of the gum. Saliva was collected into a 10 ml plastic test tube using a plastic funnel from the subjects during a period of time after the beginning of gum mastication to one minute later, 1 minute later to 3 minutes later, 3 minutes later to 6 minutes later, 6 minutes later to 10 minutes later, and 10 minutes later to 20 minutes later. The amount and pH of the saliva were measured immediately after the collection. Thereafter, the saliva supernatant was diluted with distilled water by 10 fold, followed by filtration with a 0.45 μm filter (manufactured by Millipore). The filtrate was subjected to quantification with respect to the Ca and inorganic P contents using an OCPC method (calcium C test Wako; manufactured by Wake Pure Chemicals) and a molybdic acid method.

12 healthy subjects participated in a test in which the subjects masticate two tablets of POs Ca containing gum or POs Ca-free gum (3.0 g) for 20 minutes. In the test, the subjects were not informed of the type of the gum. Saliva was collected into a 50 ml plastic test tube using a plastic funnel from the subjects during the first half 10 minutes of the 20-min mastication (saliva A) and during the second half 10 minutes (saliva B). The amount and pH of the saliva were measured immediately after the collection. Immediately after the measurement, 7 ml of the saliva was poured into a plastic vessel (10×30×60 mm) in which one enamel block embedded plate with artificial dental caries was placed in advance. This amount was such that the enamel block embedded plate was sufficiently immersed in the saliva. After the plate was immersed in saliva A for 10 minutes, the plate was immersed in saliva B for 10 minutes. Thereafter, the plate was removed, and the plate surface was thoroughly washed with distilled water. This immersion operation was conducted at 37° C., and repeated consecutively four times a day. The enamel block embedded plate was daily preserved in cool at a humidity of 100% after the operation. The test was conducted in four consecutive days using human saliva daily collected. As to the saliva used in the test, a portion of the supernatant was used and diluted by 10 fold with distilled water, followed by filtration of a 0.45 μm filter (manufactured by Millipore). The Ca and inorganic P of the filtrate was daily measured by the above-described method.

After the immersion in the human saliva, each tooth enamel was cut using a hard tissue cutter (Isomet, Buhler, USA) into sections having a thickness of about 500 μm. Each section was abraded with wet abrasive sandpaper (grit 800) to about 200 μm thick. Each section was microradiographed (PW-1830, Philips, The Netherlands). Conditions for the microradiography were that the tube voltage was 25 kV; the tube current was 25 mA; and the distance between the tube and the subject was 370 mm. Thereafter, the lesion depth (Ld, μm) and the mineral loss value ΔZ (vol %, μm) were measured by Inaba et al.'s image quantification method (Eur. J. Oral. Sci. 105:74-84, 1997).

Figure 15:
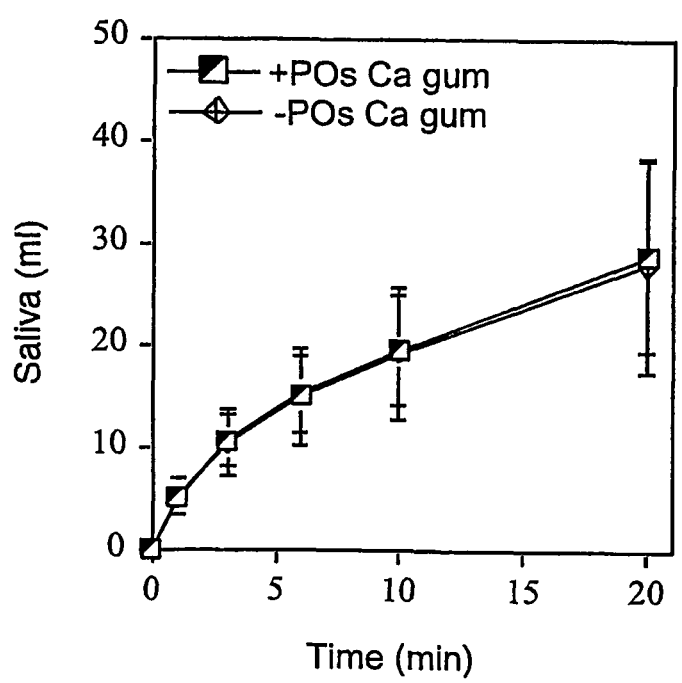
FIG. 15 is a graph showing the amount of saliva when masticating a POs Ca containing gum or a POs Ca-free gum in Example 16.
Figure 16:
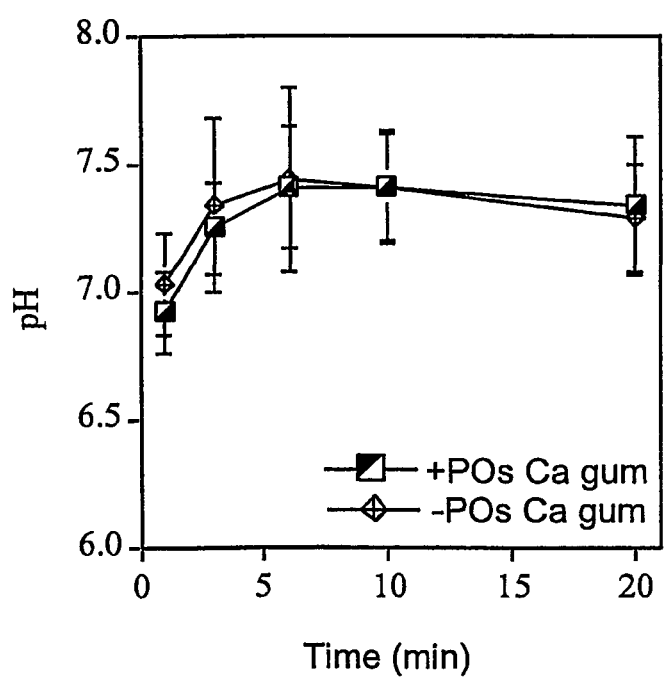
FIG. 16 is a graph showing the pH of saliva when masticating a POs Ca containing gum or a POs Ca-free gum in Example 16.
Figure 17:
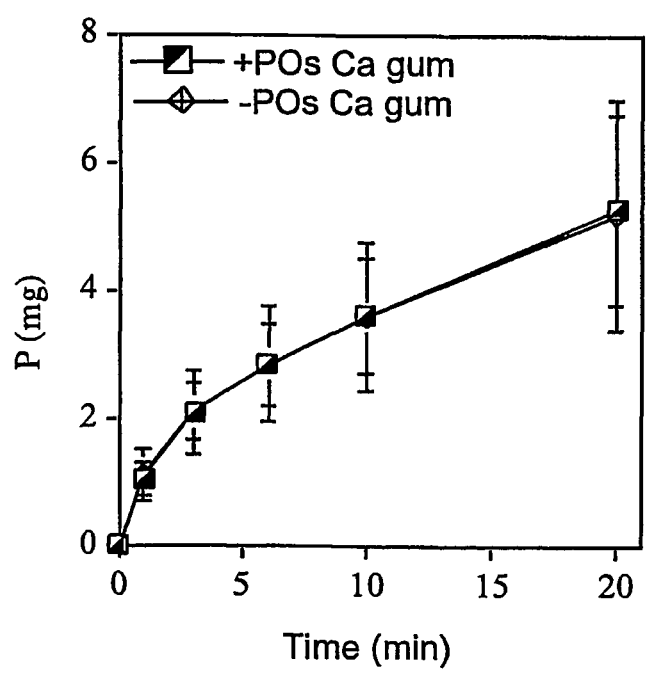
FIG. 17 is a graph showing the P content of saliva when masticating a POs Ca containing gum or a POs Ca-free gum in Example 16.

17 healthy subjects masticated 2 grains (3.0 g) of POs Ca containing gum or POs Ca-free gum for 20 minutes. In this case, the amount of saliva (FIG. 15; the horizontal axis indicates a gum mastication time and the vertical axis indicates the saliva amount (ml)), the pH of saliva (FIG. 16; the horizontal axis indicates a gum mastication time and the vertical axis indicates the pH), the Ca content of saliva (FIG. 18; the horizontal axis indicates a gum mastication time and the vertical axis indicates the calcium amount (mg)), and the P content of saliva (FIG. 17; the horizontal axis indicates a gum mastication time and the vertical axis indicates the phosphorus amount (mg)), were measured over time where the values are represented by integrated values from the start. Moreover, a change in the Ca/P ratio of saliva (FIG. 19; the horizontal axis indicates a gum mastication time and the vertical axis indicates the Ca/P ratio) were calculated. In each of figures, POs Ca containing gum (+POs Ca gum) and POs Ca-free gum (−POs Ca gum) are indicated by squares and diamonds, respectively.

Figure 18:
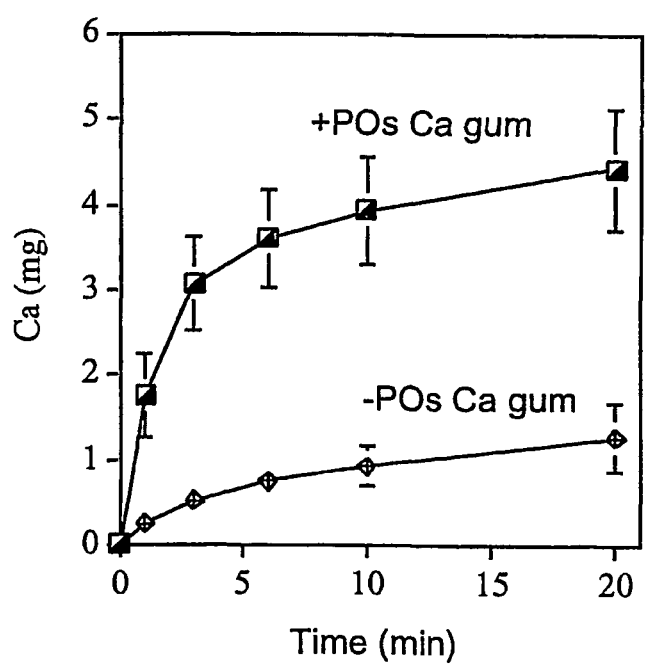
FIG. 18 is a graph showing the Ca content of saliva when masticating a POs Ca containing gum or a POs Ca-free gum in Example 16.
Figure 19:
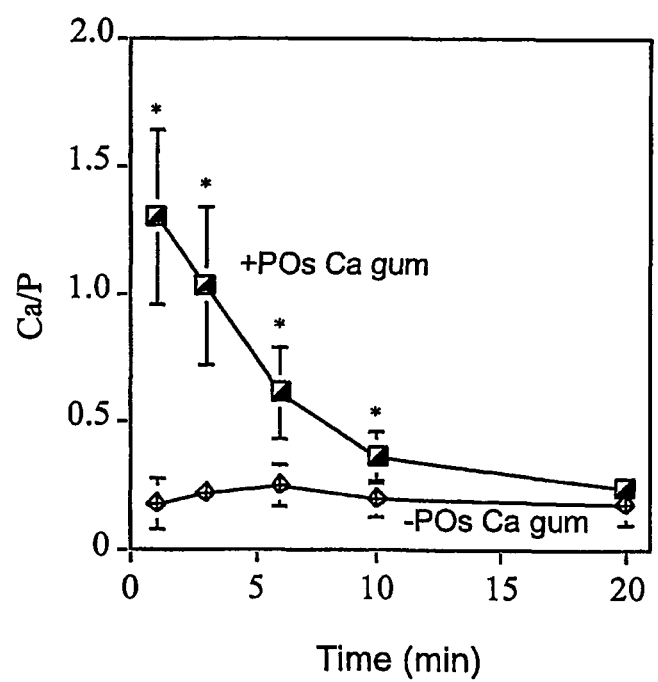
FIG. 19 is a graph showing changes in Ca/P ratio when masticating a POs Ca containing gum or a POs Ca-free gum in Example 16.

As a result, the amount of secreted saliva (FIG. 15), pH changes (FIG. 16), and changes in the P content (FIG. 17) did not vary among gum types to a statistically significant level. In the 20-minute gum mastication, about 30 ml of saliva was secreted, and the pH of saliva was increased from 7.0 at the beginning of the gum mastication to about 7.5 after 5 minutes. The P content of saliva secreted by the gum mastication was about 5 mg, which is sufficient for remineralization as compared to the Ca content. In contrast, it was clearly found that the amount of Ca dissolved in saliva at the time point 20 minutes after the beginning of mastication in the case of the POs Ca containing gum was about four times as much as that in the case of the POs Ca-free gum (FIG. 18). Since a certain amount of P is inherently present in saliva (FIG. 16), the Ca/P ratio was also significantly high in the case of the POs Ca containing gum ($p<0.001$) (FIG. 19). In the above-described analysis results, there was no significant difference found between the male and female subjects.

Table 9 shows the results of analysis of saliva A and saliva B collected from the 12 healthy subjects who masticated two grains (3.0 g) of POs Ca containing gum or POs Ca-free gum for 20 minutes.

TABLE 9

Comparison of salivary volumes, pH and mineral content

|  | Gum spacies | A saliva | B saliva |
|---|---|---|---|
| Saliva (ml) | +POs-Ca | 20.34 ± 4.13 | 9.35 ± 3.24 |
|  | −POs-Ca | 20.74 ± 4.43 | 9.65 ± 3.35 |
| Ca (mM) | +POs-Ca | 6.29 ± 2.44** | 1.72 ± 0.53* |
|  | −POS-Ca | 1.69 ± 0.41 | 1.51 ± 0.42 |
| P (mM) | +POs-Ca | 5.62 ± 1.41 | 6.22 ± 1.31 |
|  | −POs-Ca | 6.15 ± 1.35 | 6.49 ± 1.15 |
| Ca/P | +POs-Ca | 1.12 ± 0.31** | 0.28 ± 0.08 |
|  | −POs-Ca | 0.28 ± 0.08 | 0.23 ± 0.06 |

Mean ± SD,
*$p < 0.05$,
**$p < 0.001$,
n = 12

In either gum, the amount of saliva A was about two times as much as that of saliva B. In saliva A, there was a significant difference in the Ca content between the POs Ca-free gum and the POs Ca containing gum. However, in saliva B, such a difference was small. As to the P amount, there was no difference recognized between the gums and between saliva A and B. Therefore, in saliva A, the Ca/P ratio when masticating the POs Ca containing gum was about 4 times as high as that when masticating the POs Ca-free gum.

Figure 20:
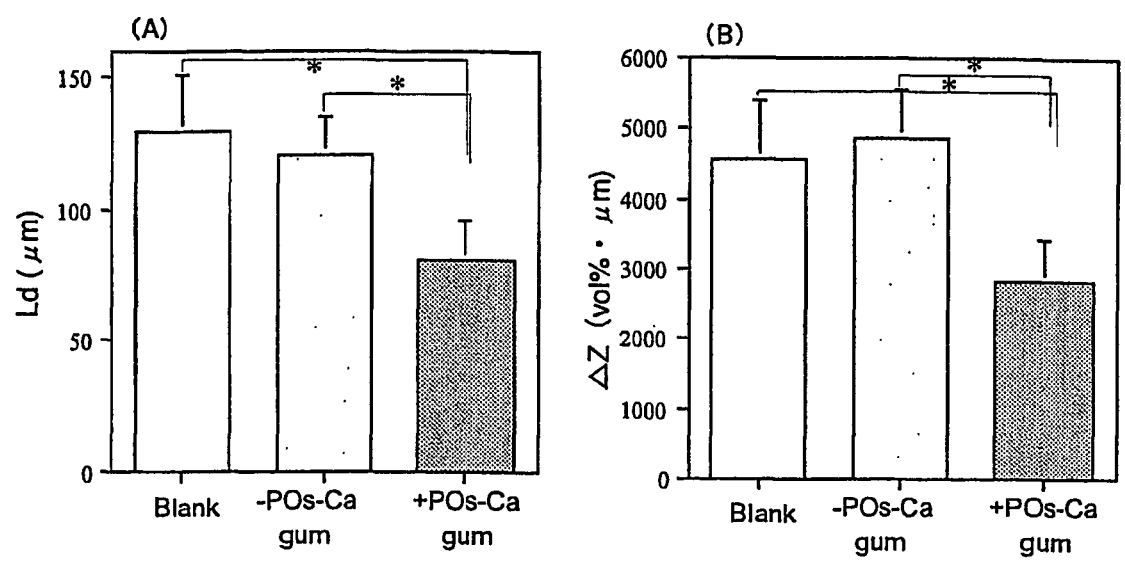
FIG. 20A is a graph showing lesion depth in each treated tooth in Example 16.
FIG. 20B is a graph showing a mineral loss value in each treated tooth in Example 16.

Next, the results of evaluating the remineralization promoting effect on the treated teeth of the 12 subjects are shown as lesion depth and mineral loss value in FIG. 20A (the vertical axis indicates the lesion depth (Ld, μm)) and FIG. 20B (the vertical axis indicates the mineral loss value ΔZ (vol %, μm)). In either figure, the horizontal axis indicates blank, the POs Ca containing gum, and the POs Ca-free gum in this order. The restoration of the demineralized tooth enamel was observed in terms of both the lesion depth (Ld) and the mineral loss value (ΔZ) in the case of the POs Ca containing gum more significantly than in the case of the POs Ca-free gum. That is, in the POs Ca containing gum mastication group, promotion of remineralization was obtained ($p<0.001$).

Example 17

Example 17 shows the remineralization promoting effect of a chewing gum containing phosphorylated oligosaccharides on enamel in the human oral cavity.

Similar to Example 13, two tablet gum (about 1.5 g/tablet), i.e., a POs Ca containing gum and a non-POs Ca containing sugarless gum, were prepared. All experimental reagents used were guaranteed reagents.

Enamel disks (5 mm in diameter; 1.5 mm in thickness) were prepared from the enamel portions of the crown parts of bovine incisors. The head surfaces of the buccal surfaces were polished with a wet abrasive sandpaper (grit 800) to expose a fresh and flat plane of enamel. The thus-prepared enamel disks were immersed in 100 ml of 0.1 M lactic acid solution (pH 5.0) at 37° C. for 3 days to generate artificial dental caries. After the demineralization, three enamel disks were attached at the palatal region of upper right molars in a removable palatal plate.

12 healthy subjects (6 males and 6 female; mean age=21 years old) masticated two pieces at a time (3.0 g) of a POs Ca containing gum, a POs Ca-free gum, or a sucrose gum (containing 62% of sucrose) (one grain; about 1.5 g) for 20 minutes. In this test, each subject chewed one of the gums 4 times a day. A person in charge of this test as well as the subjects were not informed of the type of a gum which the subjects were chewing. For each gum, the test was conducted for two straight weeks. There was a one-week interval between each test. The palatal plate was attached for 20 minutes each during and after mastication of a gum. During the test period, the subjects did not use a fluorine agent and the detached palatal plate was stored in 100% humidity, avoiding drying.

Figure 21:
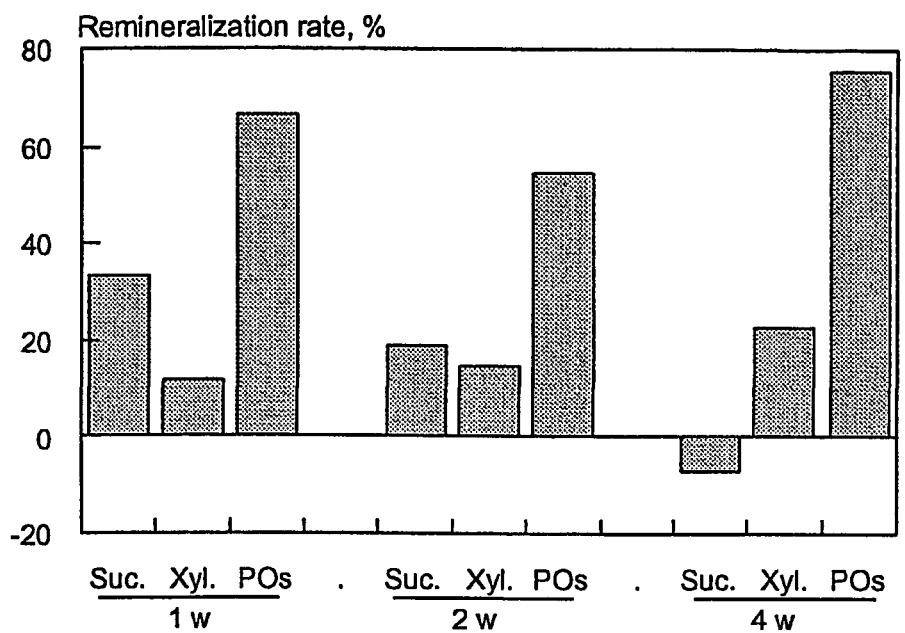
FIG. 21 is a graph showing a remineralization rate in Example 17.

The test tooth attached was removed from the palatal plate of each subject after 1, 2 and 4 weeks. A section having a thickness of about 200 μm was cut from each enamel. Each section was microradiographed (PW-1830, Philips, The Netherlands). The microradiography conditions were the following: the tube voltage was 25 kV; the tube current was 25 mA; and the distance between the tube and the subject was 370 mm. Thereafter, the lesion depth (ld, μm) was measured by Inaba et al.'s image quantification method (Eur. J. Oral. Sci. 105:74-84, 1997). The ld value was defined on the mineral distribution profile as a distance from the head surface of the tooth to the location of a lesion at which the mineral content reaches 95% level of the mineral content of the sound tissue. The remineralization rate was calculated as the reduction rate of the ld value with respect to the initial ld value after demineralization was calculated as the remineralization rate. The results of remineralization are shown in FIG. 21. In FIG. 21, the horizontal axis indicates the sucrose gum group (Suc), the POs Ca-free gum group (Xyl), and the POs Ca containing gum group (POs) in the order of week 1, week 2, and week 4. The vertical axis indicates the remineralization rate (%).

The remineralization rates in the POs Ca containing gum group (POs) were 67%, 54% and 76% at week 1, week 2 and week 4, respectively. The remineralization rates in the POs Ca-free gum group (Xyl) were 12 to 23%, which are lower than those of the POs Ca containing gum group. The sucrose gum group (Suc) showed positive remineralization rates by week 2, but finally reached to a negative value by week 4, indicating demineralization.

The human intra oral evaluation showed the higher remineralization promoting effect in the case of the POs Ca containing gum than the POs Ca-free gum and the sucrose gum. Specifically, all 12 subjects ate each kind of gum for two weeks for each and a significant result was obtained in the case of the POs Ca containing gum. Therefore, it was confirmed by the human intra oral evaluation that the addition of POs Ca to a gum leads to a high level of remineralization promoting effect. At the same time, it was also confirmed in the oral cavities that by taking a POs Ca containing gum product on a substantially daily basis, remineralization of early dental caries was enhanced, thereby preventing dental caries very effectively.

Example 18

In Example 18, the components of saliva when taking a candy containing phosphorylated oligosaccharides were analyzed.

Candies containing the following ingredients in Table 10 were prepared.

TABLE 10

| Candy | (% by weight) |
|---|---|
| Palatinit | 95 |
| POs-Ca | 2.94 |
| flavour | 2.06 |

Figure 22:
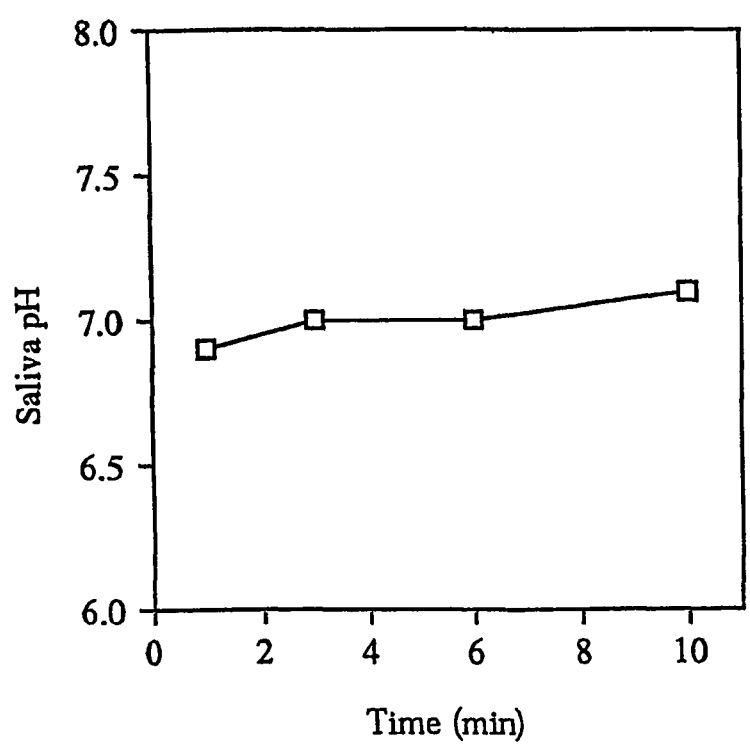
FIG. 22 is a graph showing the pH of saliva secreted when eating a POs Ca containing candy in Example 18.
Figure 23:
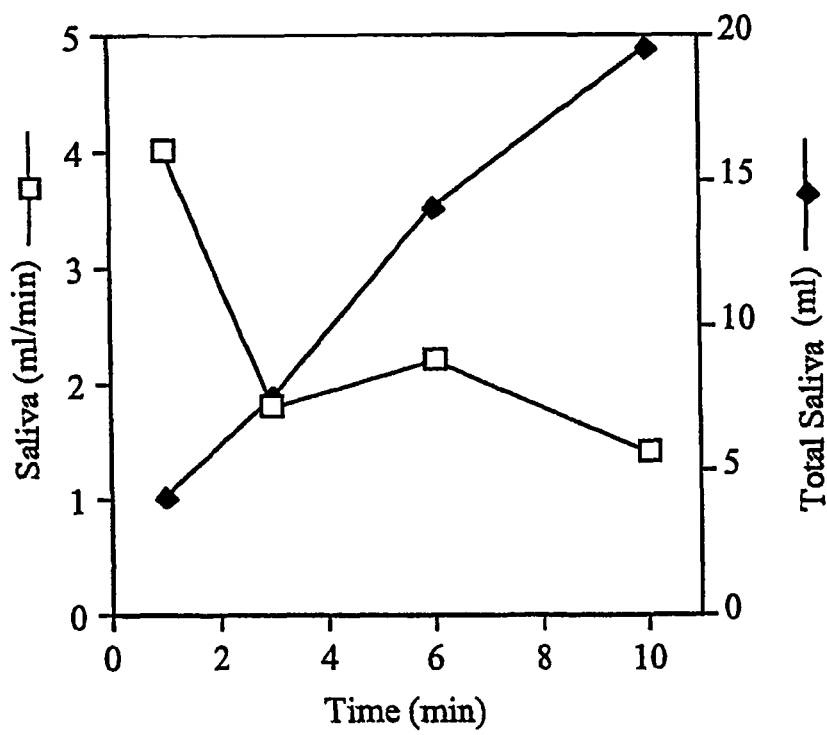
FIG. 23 is a graph showing the amount of saliva secreted when eating a POs Ca containing candy in Example 18.

4 healthy adult subjects ate a candy (4.7 g) and secreted saliva was collected. The candies were present in the oral cavities for about 10 minutes after being taken into the mouth. Saliva was collected at the following four time periods: (i) 0 to 1 minutes; (ii) 1 to 3 minutes; (iii) 3 to 6 minutes; and (iv) 6 to 10 minutes. The secreted saliva was collected through a funnel into a 15 ml test tube. Immediately after the collection, the secreted saliva was stirred, and the pH and amount of the saliva were measured. The results are shown in FIGS. 22 and 23. In FIG. 22, the horizontal axis indicates the intake time (minute) and the vertical axis indicates pH. The pH of saliva in the oral cavity was constantly 7. In FIG. 23, the horizontal axis indicates the intake time (min) and the vertical axis indicates the amount of saliva (ml/min). The amount of secreted saliva is substantially constant over the intake time.

Figure 24:
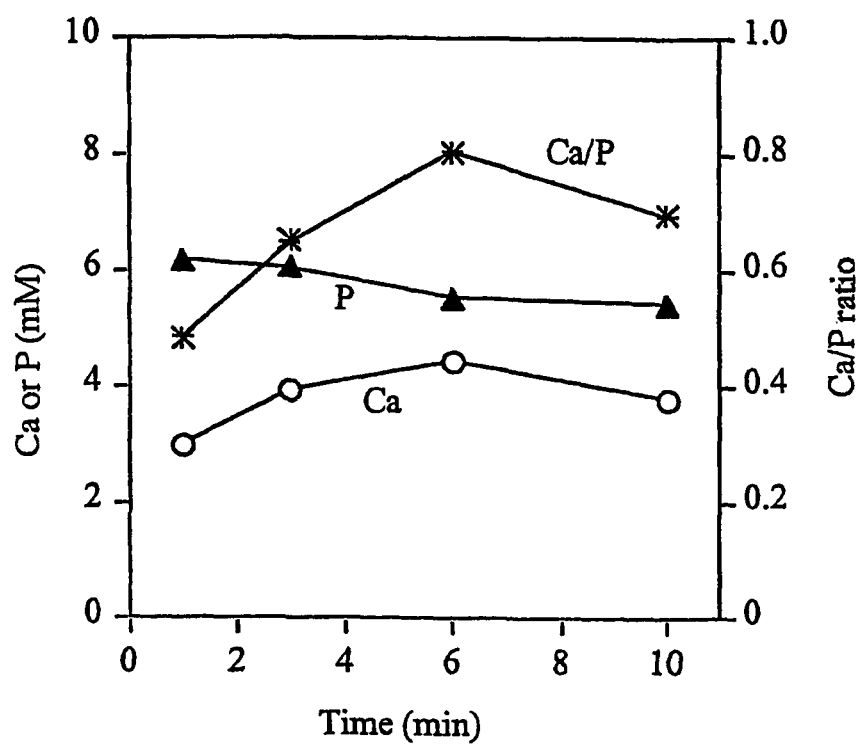
FIG. 24 is a graph showing the Ca and P contents of saliva secreted when eating a POs Ca containing candy in Example 18.
Figure 25:
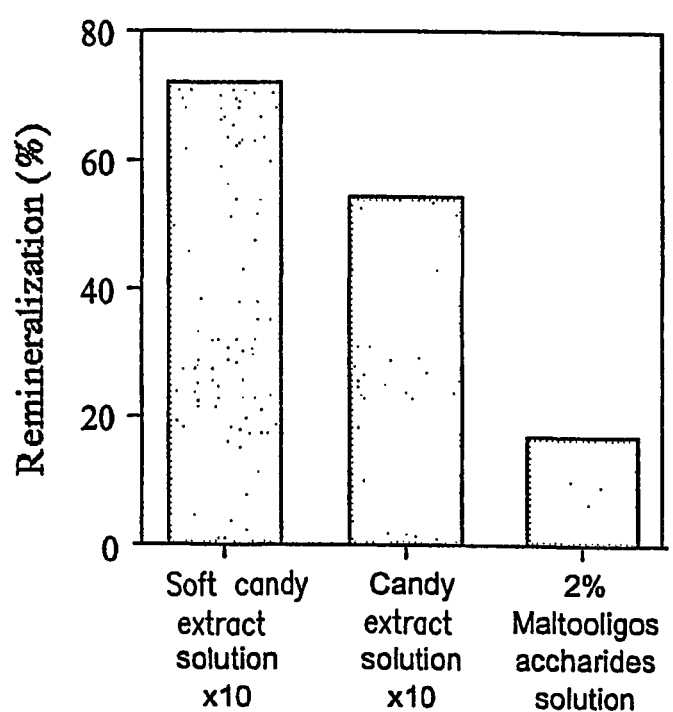
FIG. 25 is a graph showing the results of a remineralization test employing POs Ca containing candies and POs Ca containing soft candies.

Thereafter, 1800 μl of saliva was put into four centrifugal tubes. 200 μl of 1N HCl solution was added to each tube. The mixture was thoroughly mixed, followed by centrifugation at 10,000×g for 3 minutes, and subjected to 0.5 μm membrane. 10 μl of the resultant supernatant was measured by the OCPC method to determine the calcium content. 50 μl of the supernatant was measured by the molybdenum method to determine the phosphorus content. The calcium and phosphorus contents are shown in FIG. 24. In FIG. 24, the horizontal axis indicates the intake time (min), the left vertical axis indicates the calcium or phosphorus content (mM), and the right vertical axis indicates the Ca/P ratio. Both the calcium and phosphorus contents were substantially constant over the intake time (remaining about 0.6).

Example 19

In Example 19, candies and soft candies containing phosphorylated oligosaccharides were prepared to examine the remineralization promoting effect.

Candies (4.7 g/each) containing ingredients and soft candies (4.0 g/each) shown in Table 11 were prepared in accordance with a commonly used method.

TABLE 11

| | (% by weight) |
|---|---|
| Candy | |
| Palatinit | 95 |
| POs-Ca | 2.94 |
| flavour | 2.06 |
| Soft Candy | |
| Palatinit | 47.5 |
| Xylitol | 47.5 |
| POs-Ca | 2.94 |
| flavour | 2.06 |

10 ml of distilled water was added to each of the above-described candies and soft candies, and dissolved in boiling bath. The pH of the resultant extraction solution was measured by a micro pH meter. Thereafter, the extraction solution was subjected to centrifugation at 10,000×g for 3 minutes and subjected to 0.5 μm membrane. 10 μl of the resultant supernatant solution was measured by the OCPC method to determine the calcium concentration. 50 μl of the resultant supernatant solution was measured by vanadmolybdic acid method to determine the inorganic phosphorus concentration. The results are shown in Table 12.

TABLE 12

Mineral content of Ca and P in extract of soft candy and candy

| Products | Ca (mM) | P (mM) | Ca/P |
|---|---|---|---|
| Soft candy | 3.88 | 1.82 | 2.13 |
| Candy | 5.18 | 2.14 | 2.42 |

Further, based on the analysis result of Table 12, the 2- and 10-fold diluted extraction solutions were adjusted to have the calcium and phosphorus contents shown in Table 13. Thereafter, the remineralization promoting effect on hydroxyapatite was evaluated.

TABLE 13

Evaluation system for promoted remineralization

| 3.0 mM | $CaCl_2$ soln. |
|---|---|
| 1.8 mM | $KH_2PO_4$ soln. |
| 20 mM | HEPES buffer (pH7.0) |
| | (0.5 mg/ml Hydroxyapatite) |

The results are shown in FIG. 24. In FIG. 24, the horizontal axis indicates the intake time (min), the left vertical axis indicates the calcium or phosphorus content (mM), and the right vertical axis indicates the Ca/P ratio.

In either the candies or the soft candies, the 10-fold diluted solution showed a high level of remineralization promoting effect.

Example 20

A dentifrice having a composition shown in Table 14 was prepared by a commonly used method.

TABLE 14

| component | % by weight |
|---|---|
| silica | 15.00 |
| carboxymethylcellulose | 1.50 |
| polyethyleneglycol | 3.00 |
| sorbitol | 10.00 |
| xylitol | 10.00 |
| sodium laurylsulfate | 1.50 |
| preservative | 0.10 |
| flavour | 1.00 |
| saccharine | trace |
| sodium fluoride | 0.15 |
| POs Ca | 4.00 |
| disodium hydrogenphosphate | 3.75 |
| water | remaining |
| | 100.00 |

With this composition, a satisfactory anti-dental caries function could be achieved.

Example 21

A dentifrice having a composition shown in Table 15 was prepared by a commonly used method.

TABLE 15

| component | % by weight |
| --- | --- |
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| saccharine | 0.10 |
| sodium fluoride | 0.20 |
| POs Ca | 4.00 |
| cetylpyridinium chloride | 0.25 |
| water | remaining |
| | 100.00 |

With this composition, a satisfactory anti-dental caries function could be achieved.

Example 22

A dentifrice having a composition shown in Table 16 was prepared by a commonly used method.

TABLE 16

| component | % by weight |
| --- | --- |
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| sodium pyrophosphate | 0.50 |
| sodium fluoride | 0.20 |
| POs Ca | 4.00 |
| dextranase | 0.20 |
| water | remaining |
| | 100.00 |

With this composition, a satisfactory anti-dental caries function could be achieved.

Example 23

A dentifrice having a composition shown in Table 17 was prepared by a commonly used method.

TABLE 17

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| POs Na | 4.00 |
| sucralose ™ | 0.20 |
| water | remaining |
| | 100.00 |

With this composition, a satisfactory anti-dental caries function could be achieved.

Example 24

A dentifrice having a composition shown in Table 18 was prepared by a commonly used method.

TABLE 18

| component | % by weight |
| --- | --- |
| silica | 16.00 |
| carboxymethylcellulose | 1.50 |
| sodium polyacrylate | 2.00 |
| Pluronic | 1.00 |
| xylitol | 20.00 |
| sodium laurylsulfate | 1.50 |
| titanium dioxide | 0.50 |
| flavour | 1.00 |
| Triclosan | 0.50 |
| para-oxybenzoate ester | 0.10 |
| POs Ca | 5.00 |
| sodium monofluorophosphate | 0.80 |
| stevia extract | 1.50 |
| water | remaining |
| | 100.00 |

With this composition, a satisfactory anti-dental caries function could be achieved.

Example 25

A dentifrice having a composition shown in Table 19 was prepared by a commonly used method.

TABLE 19

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| POs Na | 4.00 |
| stevia | 0.20 |
| water | remaining |
| | 100.00 |

With this composition, a satisfactory anti-dental caries function could be achieved.

Example 26

A dentifrice having a composition shown in Table 20 was prepared by a commonly used method.

TABLE 20

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| zinc chloride | 0.20 |
| POs Na | 4.00 |
| enzyme-treated stevia | 0.20 |
| water | remaining |
| | 100.00 |

With this composition, a satisfactory anti-dental caries function could be achieved.

Example 27

A dentifrice having a composition shown in Table 21 was prepared by a commonly used method. POs Zn was prepared in the same manner as that in Example 2, except that 1 N zinc hydroxide solution was used for neutralization.

TABLE 21

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| POs Zn | 1.00 |
| water | remaining |
| | 100.00 |

With this composition, a satisfactory anti-dental caries function could be achieved.

Example 28

A dentifrice having a composition shown in Table 22 was prepared by a commonly used method.

TABLE 22

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| sodium tripolyphosphate | 2.00 |
| POs Ca | 4.00 |
| water | remaining |
| | 100.00 |

With this composition, a satisfactory anti-dental caries function could be achieved.

Example 29

A mouthwash having a composition shown in Table 23 was prepared by a commonly used method.

TABLE 23

| component | % by weight |
| --- | --- |
| ethylalcohol | 10.00 |
| sodium laurylsulfate | 1.50 |
| glycerin | 10.00 |
| menthol | 1.00 |
| xylitol | 17.00 |
| POs Ca | 5.00 |
| cetylpyridinium chloride | 0.25 |
| water | remaining |
| | 100.00 |

With this composition, a satisfactory anti-dental caries function could be achieved.

Example 30

A mouthwash having a composition shown in Table 24 was prepared by a commonly used method.

TABLE 24

| component | % by weight |
| --- | --- |
| ethylalcohol | 10.00 |
| sodium laurylsulfate | 1.50 |
| glycerin | 10.00 |
| menthol | 1.00 |
| xylitol | 17.00 |
| POs Ca | 5.00 |
| disodium hydrogenphosphate | 3.75 |
| water | remaining |
| | 100.00 |

With this composition, a satisfactory anti-dental caries function could be achieved.

Example 31

A mouthwash having a composition shown in Table 25 was prepared by a commonly used method.

TABLE 25

| component | % by weight |
| --- | --- |
| ethylalcohol | 10.00 |
| sodium laurylsulfate | 1.50 |
| glycerin | 10.00 |
| menthol | 1.00 |
| xylitol | 17.00 |
| POs Ca | 5.00 |
| sodium fluoride | 0.20 |
| water | remaining |
| | 100.00 |

With this composition, a satisfactory anti-dental caries function could be achieved.

Example 32

A mouthwash having a composition shown in Table 26 was prepared by a commonly used method.

TABLE 26

| component | % by weight |
| --- | --- |
| ethylalcohol | 10.00 |
| sodium laurylsulfate | 1.50 |
| glycerin | 10.00 |
| menthol | 1.00 |
| xylitol | 17.00 |
| POs Na | 5.00 |
| α-calcium tertiary phosphate | 4.00 |
| disodium hydrogenphosphate | 3.75 |
| water | remaining |
| | 100.00 |

With this composition, a satisfactory anti-dental caries function could be achieved.

Example 33

A mouthwash having a composition shown in Table 27 was prepared by a commonly used method. POs Zn was prepared in the same manner as that in Example 2, except that 1 N zinc hydroxide solution was used for neutralization.

TABLE 27

| component | % by weight |
| --- | --- |
| ethylalcohol | 10.00 |
| sodium laurylsulfate | 1.50 |
| glycerin | 10.00 |
| menthol | 1.00 |
| xylitol | 17.00 |
| POs Zn | 5.00 |
| cetylpyridinium chloride | 0.25 |
| α-calcium tertiary phosphate | 4.00 |
| water | remaining |
| | 100.00 |

With this composition, a satisfactory anti-dental caries function could be achieved.

Example 34

An oral ointment having a composition shown in Table 28 was prepared by a commonly used method.

TABLE 28

| component | % by weight |
| --- | --- |
| liquid paraffin | 25.00 |
| sodium fragdecin | 1.00 |
| white petrolatum | 25.00 |
| silicone oil | 4.00 |
| carboxymethylcellulose | 25.00 |
| pectin | 10.00 |
| flavour | 1.05 |
| sodium fluoride | 0.20 |
| POs Ca | 5.00 |
| disodium hydrogenphosphate | 3.75 |
| | 100.00 |

With this composition, a satisfactory anti-dental caries function could be achieved.

Example 35

An oral ointment having a composition shown in Table 29 was prepared by a commonly used method.

TABLE 29

| component | % by weight |
| --- | --- |
| liquid paraffin | 25.00 |
| sodium fragdecin | 1.00 |
| white petrolatum | 25.00 |
| silicone oil | 4.00 |
| carboxymethylcellulose | 25.00 |
| xylitol | 10.00 |
| flavour | 1.05 |
| sodium fluoride | 0.20 |
| POs Ca | 5.00 |
| disodium hydrogenphosphate | 3.75 |
| | 100.00 |

With this composition, a satisfactory anti-dental caries function could be achieved.

Example 36

A dentifrice having a composition shown in Table 30 was prepared by a commonly used method.

TABLE 30

| component | % by weight |
| --- | --- |
| silica | 15.00 |
| carboxymethylcellulose | 1.50 |
| polyethyleneglycol | 3.00 |
| sorbitol | 10.00 |
| xylitol | 10.00 |
| sodium laurylsulfate | 1.50 |
| preservative | 0.10 |
| flavour | 1.00 |
| saccharine | trace |
| sodium fluoride | 0.15 |
| chondroitin sulfate | 4.00 |
| disodium hydrogenphosphate | 3.75 |
| water | remaining |
| | 100.00 |

With this composition, a satisfactory anti-dental caries function could be achieved.

Example 37

A dentifrice having a composition shown in Table 31 was prepared by a commonly used method.

TABLE 31

| component | % by weight |
| --- | --- |
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| saccharine | 0.10 |
| sodium fluoride | 0.20 |
| chondroitin sulfate | 4.00 |
| cetylpyridinium chloride | 0.25 |
| water | remaining |
| | 100.00 |

With this composition, a satisfactory anti-dental caries function could be achieved.

Example 38

A dentifrice having a composition shown in Table 32 was prepared by a commonly used method.

TABLE 32

| component | % by weight |
| --- | --- |
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| sodium pyrophosphate | 0.50 |
| sodium fluoride | 0.20 |
| chondroitin sulfate | 4.00 |
| dextranase | 0.20 |
| water | remaining |
| | 100.00 |

With this composition, a satisfactory anti-dental caries function could be achieved.

Example 39

A dentifrice having a composition shown in Table 33 was prepared by a commonly used method.

TABLE 33

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| chondroitin sulfate | 4.00 |
| sucralose ™ | 0.20 |
| water | remaining |
| | 100.00 |

With this composition, a satisfactory anti-dental caries function could be achieved.

Example 40

A dentifrice having a composition shown in Table 34 was prepared by a commonly used method.

TABLE 34

| component | % by weight |
| --- | --- |
| silica | 16.00 |
| carboxymethylcellulose | 1.50 |
| sodium polyacrylate | 2.00 |
| Pluronic | 1.00 |
| xylitol | 20.00 |
| sodium laurylsulfate | 1.50 |
| titanium dioxide | 0.50 |
| flavour | 1.00 |
| Triclosan | 0.50 |
| para-oxybenzoate ester | 0.10 |
| chondroitin sulfate | 5.00 |

TABLE 34-continued

| component | % by weight |
| --- | --- |
| sodium monofluorophosphate | 0.80 |
| stevia extract | 1.50 |
| water | remaining |
| | 100.00 |

With this composition, a satisfactory anti-dental caries function could be achieved.

Example 41

A dentifrice having a composition shown in Table 35 was prepared by a commonly used method.

TABLE 35

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| chondroitin sulfate | 4.00 |
| stevia | 0.20 |
| water | remaining |
| | 100.00 |

With this composition, a satisfactory anti-dental caries function could be achieved.

Example 42

A dentifrice having a composition shown in Table 36 was prepared by a commonly used method.

TABLE 36

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| zinc chloride | 0.20 |
| chondroitin sulfate | 4.00 |
| enzyme-treated stevia | 0.20 |
| water | remaining |
| | 100.00 |

With this composition, a satisfactory anti-dental caries function could be achieved.

Example 43

A dentifrice having a composition shown in Table 37 was prepared by a commonly used method.

TABLE 37

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| chondroitin sulfate | 1.00 |
| water | remaining |
| | 100.00 |

With this composition, a satisfactory anti-dental caries function could be achieved.

Example 44

A dentifrice having a composition shown in Table 38 was prepared by a commonly used method.

TABLE 38

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| sodium tripolyphosphate | 2.00 |
| chondroitin sulfate | 4.00 |
| water | remaining |
| | 100.00 |

With this composition, a satisfactory anti-dental caries function could be achieved.

Example 45

A mouthwash having a composition shown in Table 39 was prepared by a commonly used method.

TABLE 39

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| chondroitin sulfate | 5.00 |
| cetylpyridinium chloride | 0.25 |
| water | remaining |
| | 100.00 |

With this composition, a satisfactory anti-dental caries function could be achieved.

Example 46

A mouthwash having a composition shown in Table 40 was prepared by a commonly used method.

TABLE 40

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| chondroitin sulfate | 5.00 |
| disodium hydrogenphosphate | 3.75 |
| water | remaining |
| | 100.00 |

With this composition, a satisfactory anti-dental caries function could be achieved.

Example 47

A mouthwash having a composition shown in Table 41 was prepared by a commonly used method.

TABLE 41

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| chondroitin sulfate | 5.00 |
| sodium fluoride | 0.20 |
| water | remaining |
| | 100.00 |

With this composition, a satisfactory anti-dental caries function could be achieved.

Example 48

A mouthwash having a composition shown in Table 42 was prepared by a commonly used method.

TABLE 42

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| chondroitin sulfate | 5.00 |
| α-calcium tertiary phosphate | 4.00 |
| disodium hydrogenphosphate | 3.75 |
| water | remaining |
| | 100.00 |

With this composition, a satisfactory anti-dental caries function could be achieved.

Example 49

A mouthwash having a composition shown in Table 43 was prepared by a commonly used method.

TABLE 43

| component | % by weight |
| --- | --- |
| ethylalcohol | 10.00 |
| sodium laurylsulfate | 1.50 |
| glycerin | 10.00 |
| menthol | 1.00 |
| xylitol | 17.00 |
| chondroitin sulfate | 5.00 |
| cetylpyridinium chloride | 0.25 |
| α-calcium tertiary phosphate | 4.00 |
| water | remaining |
| | 100.00 |

With this composition, a satisfactory anti-dental caries function could be achieved.

Example 50

An oral ointment having a composition shown in Table 44 was prepared by a commonly used method.

TABLE 44

| component | % by weight |
| --- | --- |
| liquid paraffin | 25.00 |
| sodium fragdecin | 1.00 |
| white petrolatum | 25.00 |
| silicone oil | 4.00 |
| carboxymethylcellulose | 25.00 |
| pectin | 10.00 |
| flavour | 1.05 |
| sodium fluoride | 0.20 |
| chondroitin sulfate | 5.00 |
| disodium hydrogenphosphate | 3.75 |
| | 100.00 |

With this composition, a satisfactory anti-dental caries function could be achieved.

Example 51

An oral ointment having a composition shown in Table 45 was prepared by a commonly used method.

TABLE 45

| component | % by weight |
| --- | --- |
| liquid paraffin | 25.00 |
| sodium fragdecin | 1.00 |
| white petrolatum | 25.00 |
| silicone oil | 4.00 |
| carboxymethylcellulose | 25.00 |
| xylitol | 10.00 |
| flavour | 1.05 |
| sodium fluoride | 0.20 |
| chondroitin sulfate | 5.00 |
| disodium hydrogenphosphate | 3.75 |
| | 100.00 |

With this composition, a satisfactory anti-dental caries function could be achieved.

Example 52

A dentifrice having a composition shown in Table 46 was prepared by a commonly used method.

TABLE 46

| component | % by weight |
| --- | --- |
| silica | 15.00 |
| carboxymethylcellulose | 1.50 |
| polyethyleneglycol | 3.00 |
| sorbitol | 10.00 |
| xylitol | 10.00 |
| sodium laurylsulfate | 1.50 |
| preservative | 0.10 |
| flavour | 1.00 |
| saccharine | trace |
| sodium fluoride | 0.15 |
| chondroitin sulfatedimer | 4.00 |
| disodiumhydrogenphosphate | 3.75 |
| water | remaining |
| | 100.00 |

With this composition, a satisfactory anti-dental caries function could be achieved.

Example 53

A dentifrice having a composition shown in Table 47 was prepared by a commonly used method.

TABLE 47

| component | % by weight |
| --- | --- |
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| saccharine | 0.10 |
| sodium fluoride | 0.20 |
| chondroitin sulfate dimer | 4.00 |
| cetylpyridinium chloride | 0.25 |
| water | remaining |
| | 100.00 |

With this composition, a satisfactory anti-dental caries function could be achieved.

Example 54

A dentifrice having a composition shown in Table 48 was prepared by a commonly used method.

TABLE 48

| component | % by weight |
| --- | --- |
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| sodium pyrophosphate | 0.50 |
| sodium fluoride | 0.20 |
| chondroitin sulfate dimer | 4.00 |
| dextranase | 0.20 |
| water | remaining |
| | 100.00 |

With this composition, a satisfactory anti-dental caries function could be achieved.

Example 55

A dentifrice having a composition shown in Table 49 was prepared by a commonly used method.

TABLE 49

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| chondroitin sulfate dimer | 4.00 |
| sucralose ™ | 0.20 |
| water | remaining |
|  | 100.00 |

With this composition, a satisfactory anti-dental caries function could be achieved.

Example 56

A dentifrice having a composition shown in Table 50 was prepared by a commonly used method.

TABLE 50

| component | % by weight |
|---|---|
| silica | 16.00 |
| carboxymethylcellulose | 1.50 |
| sodium polyacrylate | 2.00 |
| Pluronic | 1.00 |
| xylitol | 20.00 |
| sodium laurylsulfate | 1.50 |
| titanium dioxide | 0.50 |
| flavour | 1.00 |
| Triclosan | 0.50 |
| para-oxybenzoate ester | 0.10 |
| chondroitin sulfate dimer | 5.00 |
| sodium monofluorophosphate | 0.80 |
| stevia extract | 1.50 |
| water | remaining |
|  | 100.00 |

With this composition, a satisfactory anti-dental caries function could be achieved.

Example 57

A dentifrice having a composition shown in Table 51 was prepared by a commonly used method.

TABLE 51

| component | % by weight |
|---|---|
| silica | 15.00 |
| carboxymethylcellulose | 1.50 |
| polyethyleneglycol | 3.00 |

TABLE 51-continued

| component | % by weight |
|---|---|
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| chondroitin sulfate dimer | 4.00 |
| stevia | 0.20 |
| water | remaining |
|  | 100.00 |

With this composition, a satisfactory anti-dental caries function could be achieved.

Example 58

A dentifrice having a composition shown in Table 52 was prepared by a commonly used method.

TABLE 52

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| zinc chloride | 0.20 |
| chondroitin sulfate dimer | 4.00 |
| enzyme-treated stevia | 0.20 |
| water | remaining |
|  | 100.00 |

With this composition, a satisfactory anti-dental caries function could be achieved.

Example 59

A dentifrice having a composition shown in Table 53 was prepared by a commonly used method.

TABLE 53

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| chondroitin sulfate dimer | 1.00 |
| water | remaining |
|  | 100.00 |

With this composition, a satisfactory anti-dental caries function could be achieved.

Example 60

A dentifrice having a composition shown in Table 54 was prepared by a commonly used method.

TABLE 54

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| sodium tripolyphosphate | 2.00 |
| chondroitin sulfate dimer | 4.00 |
| water | remaining |
| | 100.00 |

With this composition, a satisfactory anti-dental caries function could be achieved.

Example 61

A mouthwash having a composition shown in Table 55 was prepared by a commonly used method.

TABLE 55

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| chondroitin sulfate dimer | 5.00 |
| cetylpyridinium chloride | 0.25 |
| water | remaining |
| | 100.00 |

With this composition, a satisfactory anti-dental caries function could be achieved.

Example 62

A mouthwash having a composition shown in Table 56 was prepared by a commonly used method.

TABLE 56

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| chondroitin sulfate dimer | 5.00 |
| disodium hydrogenphosphate | 3.75 |
| water | remaining |
| | 100.00 |

With this composition, a satisfactory anti-dental caries function could be achieved.

Example 63

A mouthwash having a composition shown in Table 57 was prepared by a commonly used method.

TABLE 57

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| chondroitin sulfate dimer | 5.00 |
| sodium fluoride | 0.20 |
| water | remaining |
| | 100.00 |

With this composition, a satisfactory anti-dental caries function could be achieved.

Example 64

A mouthwash having a composition shown in Table 58 was prepared by a commonly used method.

TABLE 58

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| chondroitin sulfate dimer | 5.00 |
| α-calcium tertiary phosphate | 4.00 |
| disodium hydrogenphosphate | 3.75 |
| water | remaining |
| | 100.00 |

With this composition, a satisfactory anti-dental caries function could be achieved.

Example 65

A mouthwash having a composition shown in Table 59 was prepared by a commonly used method.

TABLE 59

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| chondroitin sulfate dimer | 5.00 |
| cetylpyridinium chloride | 0.25 |
| α-calcium tertiary phosphate | 4.00 |
| water | remaining |
| | 100.00 |

With this composition, a satisfactory anti-dental caries function could be achieved.

Example 66

An oral ointment having a composition shown in Table 60 was prepared by a commonly used method.

TABLE 60

| component | % by weight |
|---|---|
| liquid paraffin | 25.00 |
| sodium fragdecin | 1.00 |
| white petrolatum | 25.00 |
| silicone oil | 4.00 |
| carboxymethylcellulose | 25.00 |
| pectin | 10.00 |
| flavour | 1.05 |
| sodium fluoride | 0.20 |
| chondroitin sulfate dimer | 5.00 |
| disodium hydrogenphosphate | 3.75 |
| | 100.00 |

With this composition, a satisfactory anti-dental caries function could be achieved.

Example 67

An oral ointment having a composition shown in Table 61 was prepared by a commonly used method.

TABLE 61

| component | % by weight |
|---|---|
| liquid paraffin | 25.00 |
| sodium fragdecin | 1.00 |
| white petrolatum | 25.00 |
| silicone oil | 4.00 |
| carboxymethylcellulose | 25.00 |
| xylitol | 10.00 |
| flavour | 1.05 |
| sodium fluoride | 0.20 |
| chondroitin sulfate dimer | 5.00 |
| disodium hydrogenphosphate | 3.75 |
| | 100.00 |

With this composition, a satisfactory anti-dental caries function could be achieved.

Example 68

A dentifrice having a composition shown in Table 62 was prepared by a commonly used method.

TABLE 62

| component | % by weight |
|---|---|
| silica | 15.00 |
| carboxymethylcellulose | 1.50 |
| polyethyleneglycol | 3.00 |
| sorbitol | 10.00 |
| xylitol | 10.00 |
| sodium laurylsulfate | 1.50 |
| preservative | 0.10 |
| flavour | 1.00 |
| saccharine | trace |
| sodium fluoride | 0.15 |
| glucose-6-phosphate | 4.00 |
| disodium hydrogenphosphate | 3.75 |
| water | remaining |
| | 100.00 |

With this composition, a satisfactory anti-dental caries function could be achieved.

Example 69

A dentifrice having a composition shown in Table 63 was prepared by a commonly used method.

TABLE 63

| component | % by weight |
|---|---|
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| saccharine | 0.10 |
| sodium fluoride | 0.20 |
| glucose-6-phosphate | 4.00 |
| cetylpyridinium chloride | 0.25 |
| water | remaining |
| | 100.00 |

With this composition, a satisfactory anti-dental caries function could be achieved.

Example 70

A dentifrice having a composition shown in Table 64 was prepared by a commonly used method.

TABLE 64

| component | % by weight |
|---|---|
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| sodium pyrophosphate | 0.50 |
| sodium fluoride | 0.20 |
| glucose-6-phosphate | 4.00 |
| dextranase | 0.20 |
| water | remaining |
| | 100.00 |

With this composition, a satisfactory anti-dental caries function could be achieved.

Example 71

A dentifrice having a composition shown in Table 65 as prepared by a commonly used method.

TABLE 65

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| glucose-6-phosphate | 4.00 |
| sucralose ™ | 0.20 |
| water | remaining |
| | 100.00 |

With this composition, a satisfactory anti-dental caries function could be achieved.

Example 72

A dentifrice having a composition shown in Table 66 was prepared by a commonly used method.

TABLE 66

| component | % by weight |
|---|---|
| silica | 16.00 |
| carboxymethylcellulose | 1.50 |
| sodium polyacrylate | 2.00 |
| Pluronic | 1.00 |
| xylitol | 20.00 |
| sodium laurylsulfate | 1.50 |
| titanium dioxide | 0.50 |
| flavour | 1.00 |
| Triclosan | 0.50 |
| para-oxybenzoate ester | 0.10 |
| glucose-6-phosphate | 5.00 |
| sodium monofluorophosphate | 0.80 |
| stevia extract | 1.50 |
| water | remaining |
| | 100.00 |

With this composition, a satisfactory anti-dental caries function could be achieved.

Example 73

A dentifrice having a composition shown in Table 67 was prepared by a commonly used method.

TABLE 67

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| glucose-6-phosphate | 4.00 |
| stevia | 0.20 |
| water | remaining |
| | 100.00 |

With this composition, a satisfactory anti-dental caries function could be achieved.

Example 74

A dentifrice having a composition shown in Table 68 was prepared by a commonly used method.

TABLE 68

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| zinc chloride | 0.20 |
| glucose-6-phosphate | 4.00 |
| enzyme-treated stevia | 0.20 |
| water | remaining |
| | 100.00 |

With this composition, a satisfactory anti-dental caries function could be achieved.

Example 75

A dentifrice having a composition shown in Table 69 was prepared by a commonly used method.

TABLE 69

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| glucose-6-phosphate | 1.00 |
| water | remaining |
| | 100.00 |

With this composition, a satisfactory anti-dental caries function could be achieved.

Example 76

A dentifrice having a composition shown in Table 70 was prepared by a commonly used method.

TABLE 70

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| sodium tripolyphosphate | 2.00 |
| glucose-6-phosphate | 4.00 |
| water | remaining |
| | 100.00 |

With this composition, a satisfactory anti-dental caries function could be achieved.

Example 77

A mouthwash having a composition shown in Table 71 was prepared by a commonly used method.

TABLE 71

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| glucose-6-phosphate | 5.00 |
| cetylpyridinium chloride | 0.25 |
| water | remaining |
|  | 100.00 |

With this composition, a satisfactory anti-dental caries function could be achieved.

Example 78

A mouthwash having a composition shown in Table 72 was prepared by a commonly used method.

TABLE 72

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| glucose-6-phosphate | 5.00 |
| disodium hydrogenphosphate | 3.75 |
| water | remaining |
|  | 100.00 |

With this composition, a satisfactory anti-dental caries function could be achieved.

Example 79

A mouthwash having a composition shown in Table 73 was prepared by a commonly used method.

TABLE 73

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| glucose-6-phosphate | 5.00 |
| sodium fluoride | 0.20 |
| water | remaining |
|  | 100.00 |

With this composition, a satisfactory anti-dental caries function could be achieved.

Example 80

A mouthwash having a composition shown in Table 74 was prepared by a commonly used method.

TABLE 74

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| glucose-6-phosphate | 5.00 |
| α-calcium tertiary phosphate | 4.00 |
| disodium hydrogenphosphate | 3.75 |
| water | remaining |
|  | 100.00 |

With this composition, a satisfactory anti-dental caries function could be achieved.

Example 81

A mouthwash having a composition shown in Table 75 was prepared by a commonly used method.

TABLE 75

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| glucose-6-phosphate | 5.00 |
| cetylpyridinium chloride | 0.25 |
| α-calcium tertiary phosphate | 4.00 |
| water | remaining |
|  | 100.00 |

With this composition, a satisfactory anti-dental caries function could be achieved.

Example 82

An oral ointment having a composition shown in Table 76 was prepared by a commonly used method.

TABLE 76

| component | % by weight |
|---|---|
| liquid paraffin | 25.00 |
| sodium fragdecin | 1.00 |
| white petrolatum | 25.00 |
| silicone oil | 4.00 |
| carboxymethylcellulose | 25.00 |
| pectin | 10.00 |
| flavour | 1.05 |
| sodium fluoride | 0.20 |
| glucose-6-phosphate | 5.00 |
| disodium hydrogenphosphate | 3.75 |
|  | 100.00 |

With this composition, a satisfactory anti-dental caries function could be achieved.

Example 83

An oral ointment having a composition shown in Table 77 was prepared by a commonly used method.

TABLE 77

| component | % by weight |
| --- | --- |
| liquid paraffin | 25.00 |
| sodium fragdecin | 1.00 |
| white petrolatum | 25.00 |
| silicone oil | 4.00 |
| carboxymethylcellulose | 25.00 |
| xylitol | 10.00 |
| flavour | 1.05 |
| sodium fluoride | 0.20 |
| glucose-6-phosphate | 5.00 |
| disodium hydrogenphosphate | 3.75 |
| | 100.00 |

With this composition, a satisfactory anti-dental caries function could be achieved.

Example 84

A dentifrice having a composition shown in Table 78 was prepared by a commonly used method.

TABLE 78

| component | % by weight |
| --- | --- |
| silica | 15.00 |
| carboxymethylcellulose | 1.50 |
| polyethyleneglycol | 3.00 |
| sorbitol | 10.00 |
| xylitol | 10.00 |
| sodium laurylsulfate | 1.50 |
| preservative | 0.10 |
| flavour | 1.00 |
| saccharine | trace |
| sodium fluoride | 0.15 |
| oligogalacturonic acid | 4.00 |
| disodium hydrogenphosphate | 3.75 |
| water | remaining |
| | 100.00 |

With this composition, a satisfactory anti-dental caries function could be achieved.

Example 85

A dentifrice having a composition shown in Table 79 was prepared by a commonly used method.

TABLE 79

| component | % by weight |
| --- | --- |
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| saccharine | 0.10 |
| sodium fluoride | 0.20 |
| oligogalacturonic acid | 4.00 |
| cetylpyridinium chloride | 0.25 |
| water | remaining |
| | 100.00 |

With this composition, a satisfactory anti-dental caries function could be achieved.

Example 86

A dentifrice having a composition shown in Table 80 was prepared by a commonly used method.

TABLE 80

| component | % by weight |
| --- | --- |
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| sodium pyrophosphate | 0.50 |
| sodium fluoride | 0.20 |
| oligogalacturonic acid | 4.00 |
| dextranase | 0.20 |
| water | remaining |
| | 100.00 |

With this composition, a satisfactory anti-dental caries function could be achieved.

Example 87

A dentifrice having a composition shown in Table 81 was prepared by a commonly used method.

TABLE 81

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| oligogalacturonic acid | 4.00 |
| sucralose ™ | 0.20 |
| water | remaining |
| | 100.00 |

With this composition, a satisfactory anti-dental caries function could be achieved.

Example 88

A dentifrice having a composition shown in Table 82 was prepared by a commonly used method.

TABLE 82

| component | % by weight |
| --- | --- |
| silica | 16.00 |
| carboxymethylcellulose | 1.50 |
| sodium polyacrylate | 2.00 |
| Pluronic | 1.00 |
| xylitol | 20.00 |
| sodium laurylsulfate | 1.50 |
| titanium dioxide | 0.50 |
| flavour | 1.00 |
| Triclosan | 0.50 |
| para-oxybenzoate ester | 0.10 |
| oligogalacturonic acid | 5.00 |

TABLE 82-continued

| component | % by weight |
|---|---|
| sodium monofluorophosphate | 0.80 |
| stevia extract | 1.50 |
| water | remaining |
| | 100.00 |

With this composition, a satisfactory anti-dental caries function could be achieved.

Example 89

A dentifrice having a composition shown in Table 83 was prepared by a commonly used method.

TABLE 83

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| oligogalacturonic acid | 4.00 |
| stevia | 0.20 |
| water | remaining |
| | 100.00 |

With this composition, a satisfactory anti-dental caries function could be achieved.

Example 90

A dentifrice having a composition shown in Table 84 was prepared by a commonly used method.

TABLE 84

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| zinc chloride | 0.20 |
| oligogalacturonic acid | 4.00 |
| enzyme-treated stevia | 0.20 |
| water | remaining |
| | 100.00 |

With this composition, a satisfactory anti-dental caries function could be achieved.

Example 91

A dentifrice having a composition shown in Table 85 was prepared by a commonly used method.

TABLE 85

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| oligogalacturonic acid | 1.00 |
| water | remaining |
| | 100.00 |

With this composition, a satisfactory anti-dental caries function could be achieved.

Example 92

A dentifrice having a composition shown in Table 86 was prepared by a commonly used method.

TABLE 86

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| sodium tripolyphosphate | 2.00 |
| oligogalacturonic acid | 4.00 |
| water | remaining |
| | 100.00 |

With this composition, a satisfactory anti-dental caries function could be achieved.

Example 93

A mouthwash having a composition shown in Table 87 was prepared by a commonly used method.

TABLE 87

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| oligogalacturonic acid | 5.00 |
| cetylpyridinium chloride | 0.25 |
| water | remaining |
| | 100.00 |

With this composition, a satisfactory anti-dental caries function could be achieved.

Example 94

A mouthwash having a composition shown in Table 88 was prepared by a commonly used method.

TABLE 88

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| oligogalacturonic acid | 5.00 |
| disodium hydrogenphosphate | 3.75 |
| water | remaining |
| | 100.00 |

With this composition, a satisfactory anti-dental caries function could be achieved.

Example 95

A mouthwash having a composition shown in Table 89 was prepared by a commonly used method.

TABLE 89

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| oligogalacturonic acid | 5.00 |
| sodium fluoride | 0.20 |
| water | remaining |
| | 100.00 |

With this composition, a satisfactory anti-dental caries function could be achieved.

Example 96

A mouthwash having a composition shown in Table 90 was prepared by a commonly used method.

TABLE 90

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| oligogalacturonic acid | 5.00 |
| α-calcium tertiary phosphate | 4.00 |
| disodium hydrogenphosphate | 3.75 |
| water | remaining |
| | 100.00 |

With this composition, a satisfactory anti-dental caries function could be achieved.

Example 97

A mouthwash having a composition shown in Table 91 was prepared by a commonly used method.

TABLE 91

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| oligogalacturonic acid | 5.00 |
| cetylpyridinium chloride | 0.25 |
| α-calcium tertiary phosphate | 4.00 |
| water | remaining |
| | 100.00 |

With this composition, a satisfactory anti-dental caries function could be achieved.

Example 98

An oral ointment having a composition shown in Table 92 was prepared by a commonly used method.

TABLE 92

| component | % by weight |
|---|---|
| liquid paraffin | 25.00 |
| sodium fragdecin | 1.00 |
| white petrolatum | 25.00 |
| silicone oil | 4.00 |
| carboxymethylcellulose | 25.00 |
| pectin | 10.00 |
| flavour | 1.05 |
| sodium fluoride | 0.20 |
| oligogalacturonic acid | 5.00 |
| disodium hydrogenphosphate | 3.75 |
| | 100.00 |

With this composition, a satisfactory anti-dental caries function could be achieved.

Example 99

An oral ointment having a composition shown in Table 93 was prepared by a commonly used method.

TABLE 93

| component | % by weight |
|---|---|
| liquid paraffin | 25.00 |
| sodium fragdecin | 1.00 |
| white petrolatum | 25.00 |
| silicone oil | 4.00 |
| carboxymethylcellulose | 25.00 |
| xylitol | 10.00 |
| flavour | 1.05 |
| sodium fluoride | 0.20 |
| oligogalacturonic acid | 5.00 |
| disodium hydrogenphosphate | 3.75 |
| | 100.00 |

With this composition, a satisfactory anti-dental caries function could be achieved.

Example 100

A dentifrice having a composition shown in Table 94 was prepared by a commonly used method.

TABLE 94

| component | % by weight |
|---|---|
| silica | 15.00 |
| carboxymethylcellulose | 1.50 |
| polyethyleneglycol | 3.00 |
| sorbitol | 10.00 |
| xylitol | 10.00 |
| sodium laurylsulfate | 1.50 |
| preservative | 0.10 |
| flavour | 1.00 |
| saccharine | trace |
| sodium fluoride | 0.15 |
| tartaric acid | 4.00 |
| disodium hydrogenphosphate | 3.75 |
| water | remaining |
| | 100.00 |

With this composition, a satisfactory anti-dental caries function could be achieved.

Example 101

A dentifrice having a composition shown in Table 95 was prepared by a commonly used method.

TABLE 95

| component | % by weight |
|---|---|
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| saccharine | 0.10 |
| sodium fluoride | 0.20 |
| tartaric acid | 4.00 |
| cetylpyridinium chlorid | 0.25 |
| water | remaining |
| | 100.00 |

With this composition, a satisfactory anti-dental caries function could be achieved.

Example 102

A dentifrice having a composition shown in Table 96 was prepared by a commonly used method.

TABLE 96

| component | % by weight |
|---|---|
| silica | 15.00 |
| carboxymethylcellulose | 1.50 |
| polyethyleneglycol | 3.00 |
| xylitol | 20.00 |
| glycerin | 5.00 |
| sodium laurylsulfate | 1.50 |
| preservative | 0.10 |
| flavour | 1.00 |
| sodium pyrophosphate | 0.50 |
| sodium fluoride | 0.20 |
| tartaric acid | 4.00 |
| dextranase | 0.20 |
| water | remaining |
| | 100.00 |

With this composition, a satisfactory anti-dental caries function could be achieved.

Example 103

A dentifrice having a composition shown in Table 97 was prepared by a commonly used method.

TABLE 97

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| tartaric acid | 4.00 |
| sucralose ™ | 0.20 |
| water | remaining |
| | 100.00 |

With this composition, a satisfactory anti-dental caries function could be achieved.

Example 104

A dentifrice having a composition shown in Table 98 was prepared by a commonly used method.

TABLE 98

| component | % by weight |
|---|---|
| silica | 16.00 |
| carboxymethylcellulose | 1.50 |
| sodium polyacrylate | 2.00 |
| Pluronic | 1.00 |
| xylitol | 20.00 |
| sodium laurylsulfate | 1.50 |
| titanium dioxide | 0.50 |
| flavour | 1.00 |
| Triclosan | 0.50 |
| para-oxybenzoate ester | 0.10 |
| tartaric acid | 5.00 |
| sodium monofluorophosphate | 0.80 |
| stevia extract | 1.50 |
| water | remaining |
| | 100.00 |

With this composition, a satisfactory anti-dental caries function could be achieved.

Example 105

A dentifrice having a composition shown in Table 99 was prepared by a commonly used method.

TABLE 99

| component | % by weight |
|---|---|
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |

TABLE 99-continued

| component | % by weight |
| --- | --- |
| flavour | 1.00 |
| α-calcium tertiary phosphate | 4.00 |
| sodium fluoride | 0.20 |
| tartaric acid | 4.00 |
| stevia | 0.20 |
| water | remaining |
| | 100.00 |

With this composition, a satisfactory anti-dental caries function could be achieved.

Example 106

A dentifrice having a composition shown in Table 100 was prepared by a commonly used method.

TABLE 100

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| zinc chloride | 0.20 |
| tartaric acid | 4.00 |
| enzyme-treated stevia | 0.20 |
| water | remaining |
| | 100.00 |

With this composition, a satisfactory anti-dental caries function could be achieved.

Example 107

A dentifrice having a composition shown in Table 101 was prepared by a commonly used method.

TABLE 101

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| α-calcium tertiary phosphate | 4.00 |
| sodium fluoride | 0.20 |
| tartaric acid | 1.00 |
| water | remaining |
| | 100.00 |

With this composition, a satisfactory anti-dental caries function could be achieved.

Example 108

A dentifrice having a composition shown in Table 102 was prepared by a commonly used method.

TABLE 102

| component | % by weight |
| --- | --- |
| silica | 15.00 |
| carboxymethylcellulose | 1.50 |
| polyethyleneglycol | 3.00 |
| xylitol | 20.00 |
| sodium laurylsulfate | 1.50 |
| preservative | 0.10 |
| flavour | 1.00 |
| sodium tripolyphosphate | 2.00 |
| tartaric acid | 4.00 |
| water | remaining |
| | 100.00 |

With this composition, a satisfactory anti-dental caries function could be achieved.

Example 109

A mouthwash having a composition shown in Table 103 was prepared by a commonly used method.

TABLE 103

| component | % by weight |
| --- | --- |
| ethylalcohol | 10.00 |
| sodium laurylsulfate | 1.50 |
| glycerin | 10.00 |
| menthol | 1.00 |
| xylitol | 17.00 |
| tartaric acid | 5.00 |
| cetylpyridinium chloride | 0.25 |
| water | remaining |
| | 100.00 |

With this composition, a satisfactory anti-dental caries function could be achieved.

Example 110

A mouthwash having a composition shown in Table 104 was prepared by a commonly used method.

TABLE 104

| component | % by weight |
| --- | --- |
| ethylalcohol | 10.00 |
| sodium laurylsulfate | 1.50 |
| glycerin | 10.00 |
| menthol | 1.00 |
| xylitol | 17.00 |
| tartaric acid | 5.00 |
| disodium hydrogenphosphate | 3.75 |
| water | remaining |
| | 100.00 |

With this composition, a satisfactory anti-dental caries function could be achieved.

Example 111

A mouthwash having a composition shown in Table 105 was prepared by a commonly used method.

TABLE 105

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| tartaric acid | 5.00 |
| sodium fluoride | 0.20 |
| water | remaining |
| | 100.00 |

With this composition, a satisfactory anti-dental caries function could be achieved.

Example 112

A mouthwash having a composition shown in Table 106 was prepared by a commonly used method.

TABLE 106

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| tartaric acid | 5.00 |
| α-calcium tertiary phosphate | 4.00 |
| disodium hydrogenphosphate | 3.75 |
| water | remaining |
| | 100.00 |

With this composition, a satisfactory anti-dental caries function could be achieved.

Example 113

A mouthwash having a composition shown in Table 107 was prepared by a commonly used method.

TABLE 107

| component | % by weight |
|---|---|
| ethylalcohol | 10.00 |
| sodium laurylsulfate | 1.50 |
| glycerin | 10.00 |
| menthol | 1.00 |
| xylitol | 17.00 |
| tartaric acid | 5.00 |
| cetylpyridinium chloride | 0.25 |
| α-calcium tertiary phosphate | 4.00 |
| water | remaining |
| | 100.00 |

With this composition, a satisfactory anti-dental caries function could be achieved.

Example 114

An oral ointment having a composition shown in Table 108 was prepared by a commonly used method.

TABLE 108

| component | % by weight |
|---|---|
| liquid paraffin | 25.00 |
| sodium fragdecin | 1.00 |
| white petrolatum | 25.00 |
| silicone oil | 4.00 |
| carboxymethylcellulose | 25.00 |
| pectin | 10.00 |
| flavour | 1.05 |
| sodium fluoride | 0.20 |
| tartaric acid | 5.00 |
| disodium hydrogenphosphate | 3.75 |
| | 100.00 |

With this composition, a satisfactory anti-dental caries function could be achieved.

Example 115

An oral ointment having a composition shown in Table 109 was prepared by a commonly used method.

TABLE 109

| component | % by weight |
|---|---|
| liquid paraffin | 25.00 |
| sodium fragdecin | 1.00 |
| white petrolatum | 25.00 |
| silicone oil | 4.00 |
| carboxymethylcellulose | 25.00 |
| xylitol | 10.00 |
| flavour | 1.05 |
| sodium fluoride | 0.20 |
| tartaric acid | 5.00 |
| disodium hydrogenphosphate | 3.75 |
| | 100.00 |

With this composition, a satisfactory anti-dental caries function could be achieved.

Example 116

An artificial saliva having a composition shown in Table 110 was prepared by a commonly used method.

TABLE 110

| | (mg) |
|---|---|
| Sodium chloride | 42.2 |
| Potassium chloride | 60 |
| Calcium chloride | 7.3 |
| Magnesium chroride | 2.6 |
| Potassium phosphate dibasic | 17.1 |
| POs Na | 20 |
| Total (ml) | 50 |

The artificial saliva has an excellent remineralization promoting effect and an ability to cause pH in the oral cavity to return to neutral.

Example 117

An artificial saliva having a composition shown in Table 111 was prepared by a commonly used method.

TABLE 111

|  | (mg) |
| --- | --- |
| Sodium chloride | 42.2 |
| Potassium chloride | 60 |
| POs Ca | 10 |
| Magnesium chroride | 2.6 |
| Potassium phosphate dibasic | 17.1 |
| Total (ml) | 50 |

The artificial saliva has an excellent remineralization promoting effect and an ability to cause pH in the oral cavity to return to neutral.

The artificial saliva can be similarly prepared by adding buffering agents other than POs Ca and POs Na.

INDUSTRIAL APPLICABILITY

As described above, the present invention provides dietary compositions and oral compositions which reduce the development of dental caries by remineralization of teeth or the like.

The invention claimed is:

1. A dietary composition which requires mastication having an anti-dental caries function, wherein the composition comprises:
   (i) a buffering agent having a pH buffering action in the oral cavity at a concentration in the range from 0.01% by weight to 20% by weight, and
   (ii) a calcium preparation,
   wherein the buffering agent is a phosphorylated oligosaccharide in the form of a sodium salt or a calcium salt,
   wherein the concentrations of the buffering agent and the calcium preparation in the composition are selected to provide a Ca/P ratio in the saliva after mastication that is substantially 1.0 to 1.67;
   wherein the phosphorylated oligosaccharide of the phosphorylated oligosaccharide in the form of a sodium salt or a calcium salt is a glucan consisting of 3 to 5 glucoses with $\alpha$-1,4 linkages, one phosphate group being linked to the glucan, or glucan consisting of 2 to 8 glucoses with $\alpha$-1,4 linkages, two phosphate groups being linked to the glucan; and
   wherein the calcium preparation is selected from the group consisting of calcium carbonate, calcium chloride, calcium lactate, calcium gluconate, whey calcium, organic acid calcium, colloidal calcium carbonate, casein phosphopeptide calcium, and calcium fluoride.

2. An oral composition having an anti-dental caries function, wherein the composition comprises:
   (i) a buffering agent having a pH buffering action in the oral cavity at a concentration in the range from 0.01% by weight to 20% by weight, and
   (ii) a calcium preparation,
   wherein the buffering agent is a phosphorylated oligosaccharide in the form of a sodium salt or a calcium salt,
   wherein the concentrations of the buffering agent and the calcium preparation in the composition are selected to provide a Ca/P ratio in the saliva of substantially 1.0 to 1.67;
   wherein the phosphorylated oligosaccharide of the phosphorylated oligosaccharide in the form of a sodium salt or a calcium salt is a glucan consisting of 3 to 5 glucoses with $\alpha$-1,4 linkages, one phosphate group being linked to the glucan, or glucan consisting of 2 to 8 glucoses with $\alpha$-1,4 linkages, two phosphate groups being linked to the glucan; and
   wherein the calcium preparation is selected from the group consisting of calcium carbonate, calcium chloride, calcium lactate, calcium gluconate, whey calcium, organic acid calcium, colloidal calcium carbonate, casein phosphopeptide calcium, and calcium fluoride,
   wherein the oral composition is in the form of a troche or lozenge.

3. A dietary composition having an anti-dental caries function, wherein the composition comprises:
   (i) a buffering agent having a pH buffering action in the oral cavity at a concentration in the range from 0.01% by weight to 20% by weight, and
   (ii) a calcium preparation,
   wherein the buffering agent is a phosphorylated oligosaccharide in the form of a sodium salt or a calcium salt;
   wherein the concentrations of the buffering agent and the calcium preparation in the composition are selected to provide a Ca/P ratio in the saliva of substantially 1.0 to 1.67;
   wherein the phosphorylated oligosaccharide of the phosphorylated oligosaccharide in the form of a sodium salt or a calcium salt is a glucan consisting of 3 to 5 glucoses with $\alpha$-1,4 linkages, one phosphate group being linked to the glucan, or glucan consisting of 2 to 8 glucoses with $\alpha$-1,4 linkages, two phosphate groups being linked to the glucan; and
   wherein the calcium preparation is selected from the group consisting of calcium carbonate, calcium chloride, calcium lactate, calcium gluconate, whey calcium, organic acid calcium, colloidal calcium carbonate, casein phosphopeptide calcium, and calcium fluoride, wherein the dietary composition is in the form of candy, soft candy or chewing gum.

4. A dietary composition according to claim 1, wherein the dietary composition is in the form of chewing gum.

5. A dietary composition according to claim 1, wherein the buffering agent is a phosphorylated oligosaccharide in the form of a calcium salt.

* * * * *